(12) United States Patent
Brand et al.

(10) Patent No.: US 10,065,965 B2
(45) Date of Patent: Sep. 4, 2018

(54) IMIDAZO[1,2-B][1,2,4]TRIAZINE DERIVATIVES AS ANTIPARASITIC AGENTS

(71) Applicants: GlaxoSmithKline Intellectual Property Development Limited, Brentford, Middlesex (GB); The University of Dundee, Dundee (GB)

(72) Inventors: Stephen Brand, Dundee (GB); Elisabet Viayna Gaza, Dundee (GB); Ian Gilbert, Dundee (GB); Eun Jung Ko, Dundee (GB); Maria Marco Martin, Madrid (ES); Timothy James Miles, Madrid (ES); Lars Henrik Sandberg, Dundee (GB); Michael George Thomas, Dundee (GB)

(73) Assignees: GlaxoSmithKline Intellectual Property Development Limited, Brentford, Middlesex (GB); The University of Dundee, Dundee (GB)

( * ) Notice: Subject to any disclaimer, the term of this patent is extended or adjusted under 35 U.S.C. 154(b) by 0 days.

(21) Appl. No.: 15/575,032

(22) PCT Filed: May 26, 2016

(86) PCT No.: PCT/EP2016/061887
§ 371 (c)(1),
(2) Date: Nov. 17, 2017

(87) PCT Pub. No.: WO2016/193111
PCT Pub. Date: Dec. 8, 2016

(65) Prior Publication Data
US 2018/0141949 A1    May 24, 2018

(30) Foreign Application Priority Data

May 29, 2015   (EP) .................................... 15382283

(51) Int. Cl.
C07D 487/04   (2006.01)
A61K 31/53    (2006.01)
A61P 33/02    (2006.01)
A61K 45/06    (2006.01)
A61K 31/5377  (2006.01)

(52) U.S. Cl.
CPC ............ C07D 487/04 (2013.01); A61K 31/53 (2013.01); A61K 31/5377 (2013.01); A61K 45/06 (2013.01); A61P 33/02 (2018.01)

(58) Field of Classification Search
CPC ....... C07D 487/04; A61P 33/02; A61K 31/53; A61K 31/5377; A61K 45/06
USPC ......................................................... 514/243
See application file for complete search history.

(56) References Cited

U.S. PATENT DOCUMENTS

2014/0275013 A1   9/2014 Chatterjee et al.
2014/0275119 A1   9/2014 Liang et al.

FOREIGN PATENT DOCUMENTS

WO    WO 2015/095477 A1    6/2015

*Primary Examiner* — Kristin Ann Vajda
(74) *Attorney, Agent, or Firm* — Nicole Ginanni; Andrea V. Lockenour

(57) ABSTRACT

A compound of Formula (I), or a salt thereof,

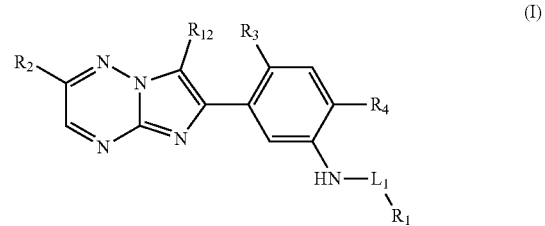

compositions comprising the compound, processes for its preparation and its use in therapy, for example in the treatment of parasitic diseases such as Chagas disease, Human African Trypanosomiasis (HAT) and leishmaniasis, particularly visceral leishmaniasis (VL).

14 Claims, No Drawings

IMIDAZO[1,2-B][1,2,4]TRIAZINE DERIVATIVES AS ANTIPARASITIC AGENTS

This application is a § 371 application of International Application No. PCT/EP2016/061887, filed 26 May 2016, which claims the benefit of EP EP15382283.8, filed 29 May 2015, the disclosures of which are incorporated herein in their entireties.

TECHNICAL FIELD OF THE INVENTION

This invention provides imidazotriazine compounds, salts thereof, compositions comprising them, processes for their preparation and their use in therapy, for example in the treatment or prevention of parasitic diseases such as Chagas disease, Human African Trypanosomiasis (HAT) and leishmaniasis, particularly visceral leishmaniasis (VL).

BACKGROUND OF THE INVENTION

Leishmaniasis

Leishmaniasis is caused in humans and animals by protozoan parasites from several *leishmania* species that are transmitted to hosts by the bites of infected female phlebotomine sandflies.

There are three main human forms of leishmaniasis—visceral (often known as kala-azar and the most serious form of the disease), cutaneous (the most common), and mucocutaneous (the most disfiguring). Most leishmaniases are zoonoses (diseases that can be transmitted from animals to humans) and the reservoir hosts include many species of mammals. Dogs are important reservoirs of *L. Infantum* responsible for visceral leishmaniasis.

Animals can also suffer from visceral, cutaneous and mucocutaneous forms of the disease.

It is estimated that 350 million people are at risk of the disease (most of them are children), with 1.3 million new cases and 20 000 to 30 000 deaths per year. (Leishmaniasis Worldwide and Global Estimates of Its Incidence. Alvar J. et al. (2012) PLoS ONE 7(5): e35671. doi:10.1371/journal.pone.0035671)

Current treatments have serious drawbacks in terms of efficacy, safety, drug resistance, stability, cost and the majority lack an oral dosing option (Structures, Targets and Recent Approaches in Anti-Leishmanial Drug Discovery and Development. Seifert K., Open Med Chem J. 2011; 5:31-39. doi: 10.2174/1874104501105010031). Geographical efficacy variation in the current treatments has started to be observed—for example, the efficacy of liposomal amphotericin B in East Africa is below what is seen in the Indian sub-continent for the same dosage ((a) Berman J D, Badaro R, Thakur C P, Wasunna K M, Behbehani K, et al. (1998) Efficacy and safety of liposomal amphotericin B (AmBisome) for visceral leishmaniasis in endemic developing countries. Bull World Health Organ 76: 25-32. (b) Eltahir A. G. Khalil, Teklu Weldegebreal, Brima M. Younis et al. Safety and Efficacy of Single Dose versus Multiple Doses of AmBisome® for Treatment of Visceral Leishmaniasis in Eastern Africa: A Randomised Trial. PLOS Neglected Tropical Diseases: published 16 Jan. 2014 (info:doi/10.1371/journal.pntd.0002613). Efficacy rates are also found to vary within Africa (Hailu A, Musa A, Wasunna M, Balasegaram M, Yifru S, et al. (2010) Geographical Variation in the Response of Visceral Leishmaniasis to Paromomycin in East Africa: A Multicentre, Open-Label, Randomized Trial. PLoS Negl Trop Dis 4(10): e709. doi:10.1371/journal.pntd.0000709).

As such there is a real unmet medical need for new oral drugs and combination therapy for the treatment and potential elimination of leishmaniasis in certain geographical areas, requiring the development of multiple new oral agents.

Chagas Disease

Chagas disease is an anthropozoonosis due to the flagellated protozoan parasite *Trypanosoma cruzi*. It is transmitted to humans and other mammals by infected faeces of a blood-sucking triatominae bug through the insect sting, another skin break or through mucous membranes, including conjunctiva or oral/digestive mucosa, occasionally causing outbreaks with contaminated food. Transmission through blood transfusion, pregnancy and delivery are also possible, and less frequently, through organ transplantation or laboratory accident.

Chagas disease is endemic throughout much of Mexico, Central America, and South America where an estimated 7-8 million people are infected. The triatomine bug thrives under poor housing conditions (for example, mud walls, thatched roofs), so in endemic countries, people living in rural areas are at greatest risk for acquiring infection. The recent migration of populations from countries endemic for the disease has increased the geographic distribution of Chagas disease, so that it is now becoming an important health issue in the USA and Canada and in many parts of Europe and the western Pacific. The most common destination for migrants from Latin America is the USA, where more than three hundred thousand individuals are infected with *T. cruzi*. Spain has the second highest number of infected immigrants, an estimated sixty-seven thousand patients. Approximately thirteen thousand die each year from the complications of Chagas-induced heart disease—a result of the chronic infection.

Chagas disease presents itself in 2 phases. The initial, acute phase lasts for about 2 months after infection. During the acute phase, a high number of parasites circulate in the blood. In most cases, symptoms are absent or mild, but can include fever, headache, enlarged lymph glands, pallor, muscle pain, difficulty in breathing, swelling and abdominal or chest pain. Manifestations of the acute disease resolve spontaneously in about 90% of infected individuals even if the infection is not treated with trypanocidal drugs. About 60-70% of these patients will never develop clinically apparent disease. These patients have the indeterminate form of chronic Chagas disease, which is characterised by positivity for antibodies against *T. cruzi* in serum, a normal 12-lead electrocardiogram (ECG), and normal radiological examination of the chest, oesophagus, and colon. The remaining 30-40% of patients will subsequently develop a determinate form of chronic disease. Up to 30% of patients with the determinate form may suffer from cardiac disorders and up to 10% from digestive (typically enlargement of the oesophagus or colon), neurological or mixed alterations or disorders. The infection can lead to sudden death or heart failure caused by progressive destruction of the heart muscle.

There is currently no vaccine for Chagas disease. Chemotherapy options are limited: benznidazole and nifurtimox are the only trypanocidal drugs available with proven efficacy against Chagas disease. Both medicines are almost 100% effective in curing the disease if given soon after infection at the onset of the acute phase. However, the efficacy of both diminishes the longer a person has been infected. Furthermore, benznidazole and nifurtimox are not consistently used in part because of their substantial side effects (peripheral neurotoxicity, digestive system irritation and serious dermatological conditions).

Newer, safer and more efficacious treatments for Chagas disease are urgently needed.

Human African Trypanosomiasis (HAT)

Human African Trypanosomiasis (HAT), Also Called African Sleeping Sickness, is a parasitic disease caused by the protozoa *Trypanosoma brucei* and transmitted by infected tse-tse flies (*Glossina* spp.), from mother to child during pregnancy and be mechanically transmitted through blood products.

Two forms of disease exist depending on the parasite sub-species:

*Trypanosoma brucei gambiense* (*T.b. gambiense*) occurring in west and central Africa, represents approximately 95% of the reported cases of sleeping sickness and causes a chronic infection. A person can be infected for months or even years without major signs or symptoms of the disease. When symptoms emerge, the patient is often already in stage 2 disease.

*Trypanosoma brucei rhodesiense* (*T.b. rhodesiense*) is found in eastern and southern Africa and represents approximately 5% of the reported cases. This sub-species of the parasite causes an acute infection. First signs and symptoms of stage 2 disease are observed a few months or weeks after infection.

The disease progresses through two distinct stages. Stage 1 is the initial haemolymphatic phase of infection and presents with non-specific symptoms including fever, rash, and fatigue. Untreated stage 1 HAT results in stage 2 disease or neurological phase, where parasites invade the central nervous system causing severe neurological symptoms and eventually death. Disturbance of the sleep cycle, which gives the disease its name, is an important feature of this second stage.

Currently four drugs are registered for the treatment of sleeping sickness. They showed different efficacy profiles depending on the *T. brucei* subspecies and the stage of the disease. The current standard treatment for stage 1 is intravenous or intramuscular pentamidine (for *T. b. gambiense*), or intravenous suramin (for *T. b. rhodesiense*). For stage 2, the front line treatment is intravenous melarsoprol, or intravenous melarsoprol in combination with oral nifurtimox, intravenous eflornithine only or eflornithine in combination with nifurtimox. All drugs suffer from undesirable and in some cases serious adverse effects.

Safer and more efficacious treatments for HAT are urgently needed.

WO 2014/151784 and US 2014/0275119 disclose certain imidazopyrimidine compounds useful for treating, preventing, inhibiting, ameliorating, or eradicating the pathology and/or symptomology of a disease caused by a parasite, such as Leishmaniasis, Human African Trypanosomiasis and Chagas disease.

WO 2014/151630 and US 2014/0275013 disclose certain compounds useful for treating, preventing, inhibiting, ameliorating, or eradicating the pathology and/or symptomology of a disease caused by a parasite, such as Leishmaniasis, Human African Trypanosomiasis and Chagas disease.

WO 2015/095477 and US 2015/175613A1 disclose certain triazolopyrimidine compounds useful for treating, preventing, inhibiting, ameliorating, or eradicating the pathology and/or symptomology of a disease caused by a parasite, such as Leishmaniasis, Human African Trypanosomiasis and Chagas disease.

SUMMARY OF THE INVENTION

The present invention provides a compound of Formula (I), or a salt thereof,
Wherein

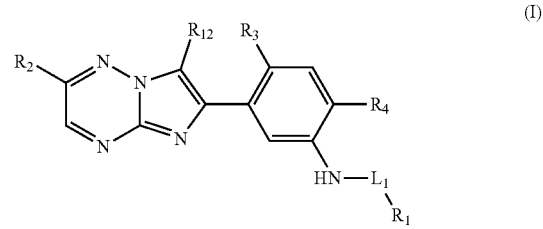

$R_1$ is selected from $C_1$-$C_6$alkyl, $C_3$-$C_7$cycloalkyl, $C_4$-$C_7$heterocycloalkyl, phenyl, $C_5$-$C_6$heteroaryl, $C_1$-$C_6$alkoxy, —$OC_3$-$C_7$cycloalkyl and $NR_{10a}R_{10b}$; wherein $C_3$-$C_7$cycloalkyl, $C_4$-$C_7$heterocycloalkyl, phenyl, $C_5$-$C_6$heteroaryl and —$OC_3$-$C_7$cycloalkyl are optionally substituted with one to three groups independently selected from hydroxy, methoxy, $C_1$-$C_3$alkyl and halo;

$L_1$ is a linker group selected from —C(O)— and —S(O)$_n$—, wherein n represents 1 to 2;

$R_3$ is selected from hydrogen, halo, methyl, methoxy and cyano;

$R_4$ is selected from hydrogen, halo, methyl, methoxy and cyano;

$R_{12}$ is selected from hydrogen, halo and methyl;

$R_2$ is selected from hydrogen, halo, Ar, Cy, X, $NR_{5a}R_{5b}$ and —C(O)—$R_{15}$;

Ar is selected from phenyl and $C_5$-$C_6$heteroaryl, each of which is optionally substituted with one to three groups independently selected from halo and -$L_2$-$R_7$;

$L_2$ is a linker group selected from a bond, —(CH$_2$)$_m$—, —O(CH$_2$)$_m$—, —$C_2$-$C_4$alkenyl- —$OC_2$-$C_4$alkenyl-, —(CH$_2$)$_p$—NH—(CH$_2$)$_q$—, and —(CH$_2$)$_p$C(O)—(CH$_2$)$_q$—; wherein m represents 1 to 4 and p and q independently represent 0 to 4;

$R_7$ is selected from hydrogen; hydroxy; $NR_{8a}R_{8b}$; $C_4$-$C_7$heterocycloalkyl optionally substituted with one or two $C_1$-$C_3$alkyl groups; $C_3$-$C_7$cycloalkyl; $C_1$-$C_6$alkoxy optionally substituted with one $NR_{14a}R_{14b}$ group; phenyl optionally substituted with one to three groups independently selected from halo, methoxy and methyl;

Cy is selected from $C_3$-$C_7$cycloalkyl, $C_4$-$C_7$heterocycloalkyl, $C_5$-$C_7$cycloalkenyl and $C_5$-$C_7$heterocycloalkenyl, each of which is optionally substituted with one to three groups independently selected from $C_1$-$C_3$alkyl, $C_4$-$C_7$heterocycloalkyl and $NR_{11a}R_{11b}$;

X is selected from $C_1$-$C_6$alkyl, $C_2$-$C_6$alkenyl, $C_1$-$C_6$alkoxy, each of which is optionally substituted with one to three groups independently selected from hydroxy, methoxy, halo, $NR_{13a}R_{13b}$ and $C_4$-$C_7$heterocycloalkyl, wherein $C_4$-$C_7$heterocycloalkyl is optionally substituted with one to three $C_1$-$C_3$alkyl groups;

$R_{5a}$ is selected from hydrogen; $C_1$-$C_6$alkyl optionally substituted with one group selected from Ar and Cy; —C(O)—$R_9$; —C(O)—$OR_9$ and —SO$_2$—$R_9$;

$R_{5b}$ is selected from hydrogen and $C_1$-$C_3$alkyl;

$R_{8a}$ and $R_{8b}$) are independently selected from hydrogen and $C_1$-$C_3$alkyl;

$R_9$ is selected from $C_1$-$C_6$alkyl, $C_3$-$C_7$cycloalkyl, $C_4$-$C_7$heterocycloalkyl, phenyl and $C_5$-$C_6$heteroaryl;

$R_{10a}$ and $R_{10b}$ are independently selected from hydrogen and $C_1$-$C_3$alkyl;

$R_{11a}$ and $R_{11b}$ are independently selected from hydrogen and $C_1$-$C_3$alkyl;

$R_{13a}$ and $R_{13b}$ are independently selected from hydrogen and $C_1$-$C_3$alkyl;

$R_{14a}$ and $R_{14b}$ are independently selected from hydrogen and $C_1$-$C_3$alkyl; and $R_{15}$ is selected from $C_1$-$C_6$alkyl, Ar and Cy.

The present invention is also directed to a compound of Formula (I), or a pharmaceutically acceptable salt thereof.

The present invention is also directed to a compound of Formula (I) which is

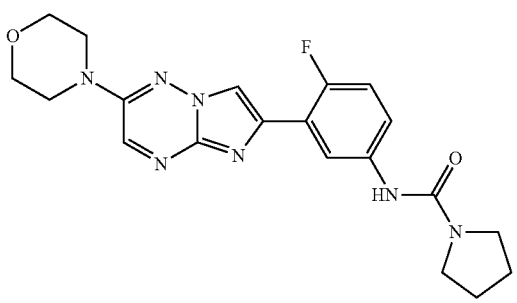 [SMILES: O=C(Nc1ccc(F)c(-c2cn3nc(N4CCOCC4)cnc3n2)c1)N1CCCC1]

The present invention is further directed to a pharmaceutical composition comprising (a) a compound of Formula (I), or a pharmaceutically acceptable salt thereof, and (b) a pharmaceutically acceptable excipient.

The present invention is also directed to a combination comprising (a) a compound of Formula (I), or a pharmaceutically acceptable salt thereof, and (b) at least one additional therapeutic agent.

The present invention is further directed to a compound of Formula (I), or a pharmaceutically acceptable salt thereof, for use in therapy.

The present invention is also directed to a compound of Formula (I), or a pharmaceutically acceptable salt thereof, for use in the treatment or prevention of a parasitic disease selected from Chagas disease, Human African Trypanosomiasis and leishmaniasis. In one embodiment, the leishmaniasis is visceral leishmaniasis. In another embodiment, the parasitic disease is Chagas disease.

The present invention is further directed to use of a compound of Formula (I), or a pharmaceutically acceptable salt thereof, in the manufacture of a medicament for the treatment or prevention of a parasitic disease selected from Chagas disease, Human African Trypanosomiasis and leishmaniasis. In one embodiment, the leishmaniasis is visceral leishmaniasis. In another embodiment, the parasitic disease is Chagas disease.

There is further provided a method of treatment or prevention of a parasitic disease selected from Chagas disease, Human African Trypanosomiasis and leishmaniasis, which method comprises administering to a mammal in need thereof, a therapeutically effective amount of a compound of Formula (I), or a pharmaceutically acceptable salt thereof. In one embodiment, the mammal is a human. In another embodiment, the leishmaniasis is visceral leishmaniasis. In a further embodiment, the parasitic disease is Chagas disease.

The present invention also provides a compound of Formula (IA), or a salt thereof, Wherein

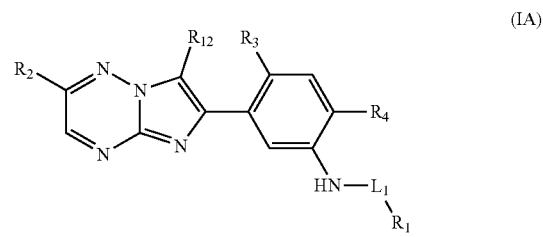

(IA)

$R_1$ is selected from $C_1$-$C_6$alkyl, $C_3$-$C_7$cycloalkyl, $C_4$-$C_7$heterocycloalkyl, phenyl, $C_5$-$C_6$heteroaryl, $C_1$-$C_6$alkoxy, —$OC_3$-$C_7$cycloalkyl and $NR_{10a}R_{10b}$; wherein $C_3$-$C_7$cycloalkyl, $C_4$-$C_7$heterocycloalkyl, phenyl, $C_5$-$C_6$heteroaryl and —$OC_3$-$C_7$cycloalkyl are optionally substituted with one to three groups selected from hydroxy, methoxy, $C_1$-$C_3$alkyl and halo;

$L_1$ is a linker group selected from —C(O)— and —S(O)$_n$—; wherein n represents 1 to 2;

$R_3$ is selected from hydrogen, halo, methyl, methoxy and cyano;

$R_4$ is selected from hydrogen, halo, methyl, methoxy and cyano;

$R_{12}$ is selected from hydrogen, halo and methyl;

$R_2$ is selected from hydrogen, halo, Ar, Cy, X and $NR_{5a}R_{5b}$;

Ar is selected from phenyl and $C_5$-$C_6$heteroaryl, each of which is optionally substituted with one to three groups independently selected from $NR_{6a}R_{6b}$ and -$L_2$-$R_7$;

$L_2$ is a linker group selected from a bond, —(CH$_2$)$_m$—, —O(CH$_2$)$_m$—, —$C_2$-$C_4$alkenyl- and —$OC_2$-$C_4$alkenyl-; wherein m represents 1 to 4;

$R_7$ is selected from hydrogen, $C_4$-$C_7$heterocycloalkyl, $C_3$-$C_7$cycloalkyl, $C_1$-$C_6$alkoxy, hydroxy and $NR_{8a}R_{8b}$;

Cy is selected from $C_3$-$C_7$cycloalkyl, $C_4$-$C_7$heterocycloalkyl, $C_5$-$C_7$cycloalkenyl and $C_5$-$C_7$heterocycloalkenyl, each of which is optionally substituted with one to three groups independently selected from $C_1$-$C_3$alkyl, $C_4$-$C_7$heterocycloalkyl and $NR_{11a}R_{11b}$;

X is selected from $C_1$-$C_6$alkyl, $C_2$-$C_6$alkenyl, $C_1$-$C_6$alkoxy, each of which is optionally substituted with one to three groups selected from hydroxy, methoxy and halo;

$R_{5a}$ is selected from hydrogen, $C_1$-$C_6$alkyl, —C(O)—$R_9$, —C(O)—O$R_9$ and —SO$_2$—$R_9$;

$R_{5b}$ is selected from hydrogen and $C_1$-$C_3$alkyl;

$R_{6a}$ and $R_{6b}$ are independently selected from hydrogen and $C_1$-$C_3$alkyl;

$R_{8a}$ and $R_{8b}$ are independently selected from hydrogen and $C_1$-$C_6$alkyl;

$R_9$ is selected from $C_1$-$C_6$alkyl, $C_3$-$C_7$cycloalkyl, $C_4$-$C_7$heterocycloalkyl, phenyl and $C_5$-$C_6$heteroaryl;

$R_{10a}$ and $R_{10b}$ are independently selected from hydrogen and $C_1$-$C_3$alkyl; and $R_{11a}$ and $R_{11b}$ are independently selected from hydrogen and $C_1$-$C_3$alkyl.

The present invention is also directed to a compound of Formula (IA), or a pharmaceutically acceptable salt thereof.

The present invention is also directed to a compound of Formula (IA) which is

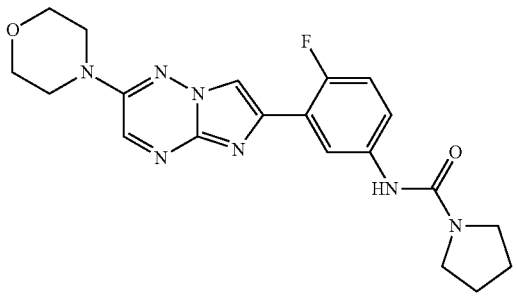 [SMILES: O=C(Nc1ccc(F)c(-c2cn3nc(N4CCOCC4)cnc3n2)c1)N1CCCC1]

The present invention also relates to pharmaceutical compositions comprising a compound of Formula (IA), or a pharmaceutically acceptable salt thereof. Accordingly, the present invention is further directed to a pharmaceutical composition comprising a compound of Formula (IA), or a pharmaceutically acceptable salt thereof.

The present invention is also directed to a combination comprising (a) a compound of Formula (IA), or a pharmaceutically acceptable salt thereof, and (b) at least one additional therapeutic agent.

The present invention is further directed to a compound of Formula (IA), or a pharmaceutically acceptable salt thereof, for use in therapy. According to another aspect, the invention relates to a compound of Formula (IA), or a pharmaceutically acceptable salt thereof, for use in therapy, which therapy is human or veterinary.

In another aspect, the invention relates to a compound of Formula (IA), or a pharmaceutically acceptable salt thereof, for use in the treatment of a parasitic disease, for example Chagas disease, Human African Trypanosomiasis or leishmaniasis, particularly visceral leishmaniasis. Accordingly, the present invention is also directed to a compound of Formula (IA), or a pharmaceutically acceptable salt thereof, for use in the treatment or prevention of a parasitic disease selected from Chagas disease, Human African Trypanosomiasis and leishmaniasis. In one embodiment, the leishmaniasis is visceral leishmaniasis. In another embodiment, the parasitic disease is Chagas disease.

In another aspect, the invention relates to the use of a compound of Formula (IA), or a pharmaceutically acceptable salt thereof, in the manufacture of a medicament for the treatment or prevention of a parasitic disease, for example Chagas disease, Human African Trypanosomiasis or leishmaniasis, particularly visceral leishmaniasis. Accordingly, the present invention is further directed to use of a compound of Formula (IA), or a pharmaceutically acceptable salt thereof, in the manufacture of a medicament for the treatment or prevention of a parasitic disease selected from Chagas disease, Human African Trypanosomiasis and leishmaniasis. In one embodiment, the leishmaniasis is visceral leishmaniasis. In another embodiment, the parasitic disease is Chagas disease.

Furthermore, the present invention also relates to a method of treatment or prevention of a parasitic disease, for example Chagas disease, Human African Trypanosomiasis or leishmaniasis, particularly visceral leishmaniasis, which method comprises administering to a mammal in need thereof, a therapeutically effective amount of a compound of Formula (IA), or a pharmaceutically acceptable salt thereof. In one aspect, the mammal is a human. Accordingly, there is provided a method of treatment or prevention of a parasitic disease selected from Chagas disease, Human African Trypanosomiasis and leishmaniasis, which method comprises administering to a mammal in need thereof, a therapeutically effective amount of a compound of Formula (IA), or a pharmaceutically acceptable salt thereof. In one embodiment, the mammal is a human. In another embodiment, the leishmaniasis is visceral leishmaniasis. In a further embodiment, the parasitic disease is Chagas disease.

DETAILED DESCRIPTION OF THE INVENTION

In a first aspect, the present invention is directed to a compound of Formula (I), or a salt thereof.

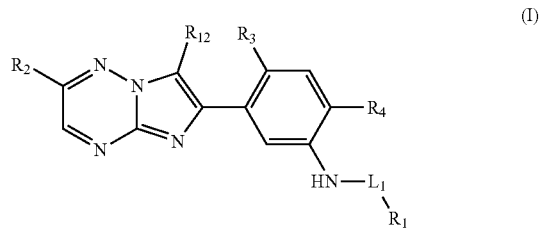

In a second aspect, the present invention is directed to a compound of Formula (I), or a pharmaceutically acceptable salt thereof.

It is to be understood that reference herein to "a compound of the invention" means a compound of Formula (I).

Since a compound of the invention is intended for use in pharmaceutical compositions it will readily be understood that it is provided in substantially pure form, for example at least 60% pure, more suitably at least 75% pure and preferably at least 85%, especially at least 98% pure (% are on a weight for weight basis). Impure preparations of the compound of the invention may be used for preparing the more pure forms used in the pharmaceutical compositions; these less pure preparations of the compounds should contain at least 1%, more suitably at least 5% and preferably from 10 to 59% of a compound of the invention or pharmaceutically acceptable salt thereof.

In one aspect, the invention relates to a compound of Formula (I) which is in the form of a free base. In a further aspect, the invention relates to a pharmaceutically acceptable salt of a compound of Formula (I).

Salts of the compounds of Formula (I) include pharmaceutically acceptable salts and salts which may not be pharmaceutically acceptable but may be useful in the preparation of compounds of Formula (I) and pharmaceutically acceptable salts thereof. Salts may be derived from certain inorganic or organic acids or bases.

Examples of salts are pharmaceutically acceptable salts. Pharmaceutically acceptable salts include acid addition salts. For a review on suitable salts see Berge et al., *J. Pharm. Sci.*, 66:1-19 (1977).

Examples of pharmaceutically acceptable acid addition salts of a compound of Formula (I) include inorganic acids such as, for example, hydrochloric acid, hydrobromic acid, orthophosphoric acid, nitric acid, phosphoric acid, or sulfuric acid, or with organic acids such as, for example, methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesuphonic, hexanoic acid or acetylsalicylic acid.

In one aspect of the invention, a compound of Formula (I) is in the form of a hydrochloric acid, hydrobromic acid, orthophosphoric acid, nitric acid, phosphoric acid, or sulfuric acid salt.

Examples of pharmaceutically acceptable inorganic base addition salts of a compound of Formula (I) include salts of ammonium, calcium, copper, ferric, ferrous, lithium, magnesium, manganic, manganous, potassium, sodium, zinc and the like.

A salt of a compound of Formula (I) can exist in all possible stoichiometric and non-stoichiometric forms.

Salts may be formed using techniques well-known in the art, for example by precipitation from solution followed by filtration, or by evaporation of the solvent.

Salts may be prepared in situ during the final isolation and purification of the compound, or by separately reacting the purified compound in its free base form with a suitable acid or base, respectively. The salt may precipitate from solution and be collected by filtration or may be recovered by evaporation of the solvent.

Typically, a pharmaceutically acceptable acid addition salt can be formed by reaction of a compound of Formula (I) with a suitable acid (such as hydrobromic, hydrochloric, sulfuric, maleic, p-toluenesulphonic, methanesulphonic, naphthalenesulphonic or succinic acids), optionally in a suitable solvent such as an organic solvent, to give the salt which is usually isolated for example by crystallisation and filtration.

The compound of Formula (I) may also be prepared as the N-oxide.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Accordingly, compounds of Formula (I) may exist as solvates. As used herein, the term solvate encompasses solvates of both a free base compound as well as any salt thereof.

Certain compounds of the invention contain chiral atoms and hence can exist in one or more (at least one) stereoisomeric forms. The present invention encompasses all of the stereoisomers of the compounds of the invention, including optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode. Unless otherwise specified (for example when the absolute stereochemistry is shown), for compounds of the invention which possess at least one stereocentre, and which can therefore form enantiomers, the compound can contain a mixture of enantiomers, for example a 1:1 mixture of enantiomers, i.e. a racemic mixture of enantiomers. This mixture of enantiomers may be separated using conventional techniques such as chiral HPLC. For an isomer of compound of the invention for which the absolute stereochemistry is stated or which is otherwise described as a single enantiomer, said isomer of a compound of the invention has, in one embodiment, at least 80% e.e. In another embodiment, said isomer of a compound of the invention has at least 90% e.e., for example at least 95% e.e. In another embodiment said isomer of compound of the invention corresponds to at least 98% e.e, for example at least 99% e.e.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest. In one aspect of the invention, a compound of Formula (I) is crystalline.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

Compounds of Formula (I) may exist in the form of isotopic variations. An isotopic variation of a compound of Formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$, $^{18}F$ and $^{36}Cl$, respectively. Certain isotopic variations of a compound of Formula (I) or a salt or solvate thereof, for example, those in which a radioactive isotope such as $^{3}H$ or $^{14}C$ is incorporated, are useful in drug and/or substrate tissue distribution studies. Tritium, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of a compound of Formula (I), or a pharmaceutically salt thereof, can generally be prepared by conventional procedures such as by the illustrative methods or by the preparations described in the Examples hereafter using appropriate isotopic variations of suitable reagents.

It will be appreciated from the foregoing, that compounds of Formula (I) and salts thereof may exist as solvates, hydrates, isomers and polymorphic forms.

It will be appreciated by those skilled in the art that certain derivatives of the compounds of Formula (I), whilst not necessarily possessing pharmacological activity as such, may be administered and thereafter metabolised in the body to form compounds of Formula (I) which compounds are pharmacologically active. Such derivatives are herein referred to as "prodrugs". Accordingly, a compound of Formula (I) may exist in the form of a prodrug. Examples of suitable derivatives are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1.

Terms and Definitions

As used herein for Formula (IA), the term "$C_1$-$C_6$alkyl" means a straight or branched chain saturated hydrocarbon group (alkyl) containing at least one, and at most six, carbon atoms. Examples of $C_1$-$C_6$alkyl include, but are not limited to, methyl, ethyl, n-propyl, isopropyl, n-butyl, isobutyl, tert-butyl, pentyl, neopentyl, or hexyls.

As used herein for Formula (IA), the term "$C_1$-$C_3$alkyl" means a straight or branched alkyl containing at least one, and at most three, carbon atoms. Examples of $C_1$-$C_3$alkyl include methyl, ethyl, n-propyl and isopropyl.

As used herein for Formula (IA), the term "$C_2$-$C_6$alkenyl" means a straight or branched chain unsaturated hydrocarbon group, containing at least two, and at most six, carbon atoms, wherein the hydrocarbon group has one or more positions of unsaturation each of which is present as a double bond. Examples of $C_2$-$C_6$alkenyl include, but are not limited to, ethenyl (—CH=CH—), propenyl (—CH$_2$—CH=CH—), isopropenyl, butenyl, pentenyl, hexenyl, 1-propenyl, 2-butenyl and 2-methyl-2-butenyl.

As used herein for Formula (IA), the term "—$C_2$-$C_4$alkenyl-" means a divalent radical (acting as a linker group) of $C_2$-$C_4$alkene, which is a straight or branched chain unsaturated hydrocarbon group containing at least two, and at most four, carbon atoms wherein the hydrocarbon group has one or more positions of unsaturation each of which is present as a double bond. Examples of —$C_2$-$C_4$alkenyl- include, but are not limited to, -ethenyl-, -propenyl- and -isopropenyl-.

As used herein for Formula (IA), the term "—$OC_2$-$C_4$alkenyl-" means a divalent radical (acting as a linker group) of O—$C_2$-$C_4$alkene, wherein $C_2$-$C_4$alkene is as defined herein, and wherein one of the radicals is on the oxygen atom and the other radical is on one of the carbon atoms. Examples of —$OC_2$-$C_4$alkenyl- include, but are not limited to, -Oethenyl-, -Opropenyl- or -Oisopropenyl-.

As used herein for Formula (IA), the term "$C_1$-$C_6$alkoxy" means a straight or branched $OC_1$-$C_6$alkyl group containing at least one, and at most six, carbon atoms. Examples of $C_1$-$C_6$alkoxy include, but are not limited to, methoxy, ethoxy, n-propoxy, isopropoxy, butoxy, isobutoxy, pentoxy and hexoxy.

As used herein for Formula (IA), the term "$C_3$-$C_7$cycloalkyl" means a non-aromatic, saturated carbocyclic ring containing at least three and at most seven carbon atoms. Examples of $C_3$-$C_7$cycloalkyl groups include cyclopropyl, cyclobutyl, cyclopentyl, cyclohexyl and cycloheptyl.

As used herein for Formula (IA), the term "$C_5$-$C_7$cycloalkenyl" means a non-aromatic, unsaturated carbocyclic ring containing at least five and at most seven carbon atoms. Examples of $C_4$-$C_7$cycloalkenyl groups include cyclopentenyl, cyclohexenyl and cycloheptenyl.

As used herein for Formula (IA), the term "—$OC_3$-$C_7$cycloalkyl" means a $C_3$-$C_7$cycloalkyl group, as defined herein, attached to an oxygen atom, the oxygen atom having a radical forming a point of attachment for the —$OC_3$-$C_7$cycloalkyl group. Examples of —$OC_3$-$C_7$cycloalkyl groups include cyclopropyloxy, cyclobutyloxy, cyclopentyloxy, cyclohexyloxy and cycloheptyloxy.

As used herein for Formula (IA), the term "$C_4$-$C_7$heterocycloalkyl" means a saturated ring containing at least four and at most seven atoms, which includes one or more, for example two, ring heteroatoms selected from nitrogen, oxygen and sulfur. Examples of $C_4$-$C_7$heterocycloalkyl groups include, but are not limited to, tetrahydrofuranyl tetrahydropyranyl, tetrahydrothiopyranyl, pyrrolidinyl, tetrahydrothiophenyl, piperidinyl, piperazinyl, morpholinyl, 1,4-dioxanyl, thiomorpholinyl, 1,4-oxathianyl, 1,4-dithianyl, dioxepanyl, azepanyl, oxepanyl and diazepanyl. The point of attachment to the rest of the molecule may be by any suitable carbon or nitrogen atom.

As used herein for Formula (IA), the term "$C_5$-$C_7$heterocycloalkenyl" means a non-aromatic unsaturated ring containing at least five and at most seven atoms, which includes one or more, for example two, ring heteroatoms selected from nitrogen, oxygen and sulfur. Examples of $C_5$-$C_7$heterocycloalkenyl groups include, but are not limited to, dihydropyranyl, dihydrofuranyl, dihydrothiophenyl, pyrrolinyl, azepinyl, oxepinyl, thiepiny, dioxepinyl, dihydropyrrolyl, dihydropyrazolyl, dihydroimidazolyl, dihydrooxazolyl, dihydrothiazolyl and dihydrothiopyranyl.

As used herein for Formula (IA), the term "$C_5$-$C_6$heteroaryl" refers to an aromatic ring comprising five or six heteroatoms selected from N, O and S. Examples of $C_5$-$C_6$heteroaryl groups include, but are not limited to, furanyl, thiophenyl, pyrrolyl, pyridyl, pyrimidyl, imidazolyl and isoxazolyl.

As used herein for Formula (IA), the term "halo" refers to fluoro, chloro, bromo or iodo.

As used herein for Formula (I), the term "$C_1$-$C_6$alkyl" means a straight or branched chain saturated hydrocarbon group (alkyl) containing at least one, and at most six, carbon atoms. Examples of $C_1$-$C_6$alkyl include, but are not limited to, methyl, ethyl, n-propyl, isopropyl, n-butyl, isobutyl, tert-butyl, pentyl, neopentyl, or hexyls.

As used herein for Formula (I), the term "$C_1$-$C_3$alkyl" means a straight or branched alkyl containing at least one, and at most three, carbon atoms. Examples of $C_1$-$C_3$alkyl include methyl, ethyl, n-propyl and isopropyl.

As used herein for Formula (I), the term "$C_2$-$C_6$alkenyl" means a straight or branched chain unsaturated hydrocarbon group, containing at least two, and at most six, carbon atoms, wherein the hydrocarbon group has one or more (at least one) positions of unsaturation each of which is present as a double bond. Examples of $C_2$-$C_6$alkenyl include, but are not limited to, ethenyl (CH=CH), propenyl (CH$_2$—CH=CH), isopropenyl, butenyl, pentenyl, hexenyl, 1-propenyl, 2-butenyl and 2-methyl-2-butenyl.

As used herein for Formula (I), the term "—$C_2$-$C_4$alkenyl-" means a divalent radical (acting as a linker group) of $C_2$-$C_4$alkene, which is a straight or branched chain unsaturated hydrocarbon group containing at least two, and at most four, carbon atoms wherein the hydrocarbon group has one or more (at least one) positions of unsaturation each of which is present as a double bond. Examples of —$C_2$-$C_4$alkenyl- include, but are not limited to, -ethenyl-, -propenyl- and -isopropenyl-.

As used herein for Formula (I), the term "—$OC_2$-$C_4$alkenyl-" means a divalent radical (acting as a linker group) of O—$C_2$-$C_4$alkene, wherein $C_2$-$C_4$alkene is as defined herein, and wherein one of the radicals is on the oxygen atom and the other radical is on one of the carbon atoms. Examples of —$OC_2$-$C_4$alkenyl- include, but are not limited to, -Oethenyl-, -Opropenyl- or -Oisopropenyl-.

As used herein for Formula (I), the term "$C_1$-$C_6$alkoxy" means a straight or branched $OC_1$-$C_6$alkyl group containing at least one, and at most six, carbon atoms. Examples of $C_1$-$C_6$alkoxy include, but are not limited to, methoxy, ethoxy, n-propoxy, isopropoxy, butoxy, isobutoxy, pentoxy and hexoxy.

As used herein for Formula (I), the term "$C_3$-$C_7$cycloalkyl" means a non-aromatic, saturated carbocyclic ring containing at least three and at most seven carbon atoms. Examples of $C_3$-$C_7$cycloalkyl groups include cyclopropyl, cyclobutyl, cyclopentyl, cyclohexyl and cycloheptyl.

As used herein for Formula (I), the term "$C_5$-$C_7$cycloalkenyl" means a non-aromatic, unsaturated carbocyclic ring containing at least five and at most seven carbon atoms. Examples of $C_4$-$C_7$cycloalkenyl groups include cyclopentenyl, cyclohexenyl and cycloheptenyl.

As used herein for Formula (I), the term "—$OC_3$-$C_7$cycloalkyl" means a $C_3$-$C_7$cycloalkyl group, as defined herein, attached to an oxygen atom, the oxygen atom having a radical forming a point of attachment for the —$OC_3$-$C_7$cycloalkyl group. Examples of —$OC_3$-$C_7$cycloalkyl groups include cyclopropyloxy, cyclobutyloxy, cyclopentyloxy, cyclohexyloxy and cycloheptyloxy.

As used herein for Formula (I), the term "$C_4$-$C_7$heterocycloalkyl" means a saturated ring containing at least four and at most seven ring atoms, wherein at least one of the ring atoms is a heteroatom selected from nitrogen, oxygen and sulfur. Examples of $C_4$-$C_7$heterocycloalkyl groups include, but are not limited to, tetrahydrofuranyl tetrahydropyranyl, tetrahydrothiopyranyl, pyrrolidinyl, tetrahydrothiophenyl, piperidinyl, piperazinyl, morpholinyl, 1,4-dioxanyl, thiomorpholinyl, 1,4-oxathianyl, 1,4-dithianyl, dioxepanyl, azepanyl, oxepanyl and diazepanyl. The point of attachment to the rest of the molecule may be by any suitable carbon or nitrogen atom.

As used herein for Formula (I), the term "$C_5$-$C_7$heterocycloalkenyl" means a non-aromatic unsaturated ring containing at least five and at most seven ring atoms, wherein at least one of the ring atoms is a heteroatom selected from nitrogen, oxygen and sulfur. Examples of $C_5$-$C_7$heterocycloalkenyl groups include, but are not limited to, dihydropyranyl, dihydrofuranyl, dihydrothiophenyl, pyrrolinyl, azepinyl, oxepinyl, thiepiny, dioxepinyl, dihydropyrrolyl, dihydropyrazolyl, dihydroimidazolyl, dihydrooxazolyl, dihydrothiazolyl and dihydrothiopyranyl.

As used herein for Formula (I), the term "$C_5$-$C_6$heteroaryl" refers to an aromatic ring comprising five or six ring atoms, wherein at least one of the ring atoms is a heteroatom selected from nitrogen, oxygen and sulfur. Examples of $C_5$-$C_6$heteroaryl groups include, but are not limited to, furanyl, thiophenyl, pyrrolyl, pyridyl, pyrimidyl, imidazolyl and isoxazolyl.

As used herein for Formula (I), the term "halo" refers to fluoro, chloro, bromo or iodo.

As used herein, the term "unsaturated" means having one or more (at least one) double bonds.

In respect of Formula (IA), in one aspect of the invention, $R_1$ is $C_4$-$C_6$heterocycloalkyl. In another aspect, $R_1$ is pyrrolidinyl.

In respect of Formula (IA), in one aspect of the invention, $L_1$ is selected from —C(O)— and —S(O)$_n$—; wherein n represents 2. In another aspect, $L_1$ is —C(O)—.

In respect of Formula (IA), in one aspect of the invention, $R_3$ is hydrogen or halo. In another aspect, $R_3$ is halo. In another aspect, $R_3$ is fluoro or chloro. In a further aspect, $R_3$ is fluoro.

In respect of Formula (IA), in one aspect of the invention, $R_4$ is hydrogen.

In respect of Formula (IA), in one aspect of the invention, $R_{12}$ is selected from hydrogen and methyl. In another aspect, $R_{12}$ is hydrogen.

In respect of Formula (IA), in one aspect of the invention, $R_2$ is hydrogen.

In respect of Formula (IA), in one aspect of the invention, $R_2$ is halo. In another aspect, $R_2$ is fluoro or chloro.

In respect of Formula (IA), in one aspect of the invention, $R_2$ is $NR_{5a}R_{5b}$.

In respect of Formula (IA), in one aspect of the invention, $R_2$ is Ar.

In respect of Formula (IA), in one aspect of the invention, Ar is selected from phenyl and $C_5$-$C_6$heteroaryl, each of which is optionally substituted with one group selected from $NR_{6a}R_{6b}$ and -$L_2$-$R_7$.

In respect of Formula (IA), in one aspect of the invention, Ar is selected from phenyl and $C_5$-$C_6$heteroaryl, each of which is optionally substituted with one group which is $NR_{6a}R_{6b}$.

In respect of Formula (IA), in one aspect of the invention, Ar is selected from phenyl and $C_5$-$C_6$heteroaryl, each of which is optionally substituted with one group which is -$L_2$-$R_7$.

In respect of Formula (IA), in one aspect of the invention, Ar is optionally substituted phenyl. In another aspect, Ar is unsubstituted phenyl.

In respect of Formula (IA), in one aspect of the invention, Ar is optionally substituted $C_5$-$C_6$heteroaryl. In one aspect, Ar is optionally substituted pyridyl. In another aspect, Ar is optionally substituted 2-pyridyl. In another aspect, Ar is optionally substituted 3-pyridyl. In another aspect, Ar is optionally substituted 4-pyridyl. In one aspect of the invention, Ar is unsubstituted $C_5$-$C_6$heteroaryl.

In respect of Formula (IA), in one aspect of the invention, $L_2$ is selected from a bond, —(CH$_2$)$_n$— and —O(CH$_2$)$_n$—, wherein n represents 1 to 4. In another aspect, $L_2$ is a bond. In another aspect, $L_2$ is —(CH$_2$)$_n$—. In a further aspect, $L_2$ is $C_2$-$C_4$alkenyl-. In one aspect, n represents 1 to 3.

In respect of Formula (IA), in one aspect of the invention, $R_7$ is selected from hydrogen, $C_4$-$C_7$heterocycloalkyl, and $C_1$-$C_6$alkoxy. In another aspect, $R_7$ is hydrogen. In another aspect, $R_7$ is $C_4$-$C_7$heterocycloalkyl, for example morpholinyl. In another aspect, $R_7$ is $C_1$-$C_6$alkoxy, for example methoxy.

In respect of Formula (IA), in one aspect of the invention, $R_2$ is Cy.

In one aspect of the invention, Cy is selected from $C_4$-$C_7$heterocycloalkyl and $C_5$-$C_7$heterocycloalkenyl, each of which is optionally substituted with one to three $C_1$-$C_3$alkyl groups.

In respect of Formula (IA), in one aspect of the invention, Cy is selected from $C_4$-$C_7$heterocycloalkyl, and $C_5$-$C_7$heterocycloalkenyl, each of which is optionally substituted with one or two $C_1$-$C_3$alkyl groups, for example with one or two methyl groups.

In respect of Formula (IA), in one aspect of the invention, Cy is optionally substituted $C_4$-$C_7$heterocycloalkyl. In another aspect, Cy is unsubstituted $C_4$-$C_7$heterocycloalkyl. In one aspect, Cy is morpholinyl.

In respect of Formula (IA), in one aspect of the invention, Cy is optionally substituted $C_5$-$C_7$heterocycloalkenyl. In another aspect, Cy is unsubstituted $C_4$-$C_7$heterocycloalkenyl.

In respect of Formula (IA), in one aspect of the invention, $R_2$ is X.

In respect of Formula (IA), in one aspect of the invention, X is selected from $C_1$-$C_6$alkyl and $C_2$-$C_6$alkenyl, each of which is optionally substituted with one to three groups selected from hydroxy, methoxy and halo. In another aspect, X is selected from $C_1$-$C_6$alkyl and $C_2$-$C_6$alkenyl, each of which is optionally substituted with one group selected from hydroxy, methoxy and halo.

In respect of Formula (IA), in one aspect of the invention, X is optionally substituted $C_1$-$C_6$alkyl. In another aspect, X is $C_1$-$C_6$alkyl substituted with one hydroxy group. In another aspect, X is unsubstituted $C_1$-$C_6$alkyl.

In respect of Formula (IA), in one aspect of the invention, X is optionally substituted $C_2$-$C_6$alkenyl. In another aspect, X is $C_2$-$C_6$alkenyl substituted with one hydroxy group. In another aspect, X is unsubstituted $C_2$-$C_6$alkenyl.

In respect of Formula (IA), in one aspect of the invention, $R_{5a}$ is selected from hydrogen and $C_1$-$C_6$alkyl.

In respect of Formula (IA), in one aspect of the invention, $R_{5b}$ is hydrogen.

In respect of Formula (IA), in one aspect of the invention, $R_{6a}$ and $R_{6b}$ are independently selected from $C_1$-$C_3$alkyl. In another aspect, $R_{6a}$ and $R_{6b}$ are both methyl.

In respect of Formula (IA), in one aspect of the invention, $R_{8a}$ and $R_{8b}$ are independently selected from $C_1$-$C_6$alkyl.

In respect of Formula (IA), in one aspect of the invention, $R_9$ is $C_1$-$C_6$alkyl.

In respect of Formula (IA), in one aspect of the invention, $R_{10a}$ and $R_{10b}$ are independently selected from hydrogen and methyl.

In respect of Formula (IA), in one aspect of the invention, $R_{11a}$ and $R_{11b}$ are independently selected from hydrogen and methyl.

In respect of Formula (I), in one embodiment of the invention, $R_1$ is selected from $C_4$-$C_6$heterocycloalkyl, $C_5$-$C_6$heteroaryl, and $C_1$-$C_6$alkoxy, wherein $C_4$-$C_6$heterocycloalkyl and $C_5$-$C_6$heteroaryl are optionally substituted with one to three groups independently selected from hydroxy, methoxy, $C_1$-$C_3$alkyl and halo.

In respect of Formula (I), in one embodiment of the invention, $R_1$ is $C_4$-$C_6$heterocycloalkyl optionally substituted with one to three groups independently selected from hydroxy, methoxy, $C_1$-$C_3$alkyl and halo. In another embodiment, $R_1$ is selected from pyrrolidinyl, isoxazolyl, pyrazolyl and azetidinyl, each of which is optionally substituted with one to three groups independently selected from hydroxy, methoxy, $C_1$-$C_3$alkyl and halo. In another embodiment, $R_1$ is selected from pyrrolidinyl, isoxazolyl, pyrazolyl and azetidinyl. In another embodiment, $R_1$ is pyrrolidinyl. In another embodiment, $R_1$ is $C_4$-$C_6$heterocycloalkyl optionally substituted with two methyl groups.

In respect of Formula (I), in one embodiment of the invention, $R_1$ is $C_5$-$C_6$heteroaryl, optionally substituted with one to three groups independently selected from hydroxy, methoxy, $C_1$-$C_3$alkyl and halo. In another embodiment, $R_1$ is furanyl, optionally substituted with one to three groups independently selected from hydroxy, methoxy, $C_1$-$C_3$alkyl and halo. In a further embodiment, R1 is furanyl.

In respect of Formula (I), in one embodiment of the invention, $R_1$ is $C_1$-$C_6$alkoxy. In another embodiment, $R_1$ is selected from ethoxy and ispopoxy.

In respect of Formula (I), in one embodiment of the invention, $L_1$ is selected from —C(O)— and —S(O)$_n$—, wherein n represents 2. In another embodiment, $L_1$ is —C(O)—. In a further embodiment, $L_1$ represents-S(O)$_n$—, wherein n represents 2.

In respect of Formula (I), in one embodiment of the invention, $L_1$-$R_1$ is

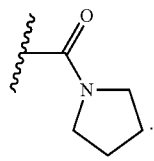

In respect of Formula (I), in one embodiment of the invention, $R_3$ is hydrogen, halo or cyano. In another embodiment of the invention, $R_3$ is hydrogen or halo. In another embodiment, $R_3$ is halo. In another embodiment, $R_3$ is fluoro or chloro. In a further embodiment, $R_3$ is fluoro.

In respect of Formula (I), in one embodiment of the invention, $R_4$ is hydrogen.

In respect of Formula (I), in one embodiment of the invention, $R_{12}$ is selected from hydrogen, fluoro and methyl. In another embodiment, $R_{12}$ is hydrogen. In another embodiment, $R_{12}$ is fluoro.

In respect of Formula (I), in one embodiment of the invention, $R_2$ is selected from hydrogen, Ar, Cy, X, $NR_{5a}R_{5b}$ and —C(O)—$R_{15}$.

In respect of Formula (I), in one embodiment of the invention, $R_2$ is hydrogen.

In respect of Formula (I), in one embodiment of the invention, $R_2$ is halo. In another embodiment, $R_2$ is fluoro or chloro.

In respect of Formula (I), in one embodiment of the invention, $R_2$ is $NR_{5a}R_{5b}$.

In respect of Formula (I), in one embodiment of the invention, $R_2$ is Ar.

In respect of Formula (I), in one embodiment of the invention, Ar is selected from phenyl and $C_5$-$C_6$heteroaryl, each of which is optionally substituted with one group which is -$L_2$-$R_7$.

In respect of Formula (I), in one embodiment of the invention, Ar is phenyl optionally substituted with one to three groups selected from halo and -$L_2$-$R_7$. In another embodiment of the invention, Ar is phenyl optionally substituted with one group which is -$L_2$-$R_7$. In another embodiment, Ar is phenyl.

In one embodiment of the invention, Ar is $C_5$-$C_6$heteroaryl optionally substituted with one to three groups selected from halo and -$L_2$-$R_7$. In another embodiment of the invention, Ar is $C_5$-$C_6$heteroaryl optionally substituted with one group which is -$L_2$-$R_7$. In one embodiment, Ar is pyridyl optionally substituted with one to three groups selected from halo and -$L_2$-$R_7$. In one embodiment, Ar is pyridyl optionally substituted with one group which is -$L_2$-$R_7$. In one embodiment, Ar is pyridyl. In another embodiment, Ar is optionally substituted 2-pyridyl. In another aspect, Ar is optionally substituted 3-pyridyl. In another embodiment, Ar is optionally substituted 4-pyridyl.

In one embodiment of the invention, $L_2$ is selected from a bond, —(CH$_2$)$_m$—, —O(CH$_2$)$_m$— and —(CH$_2$)$_p$—NH—(CH$_2$)$_q$—, wherein m represents 1 to 4 and p and q independently represent 0 to 4. In one embodiment, $L_2$ is a bond. In another embodiment, $L_2$ is —(CH$_2$)$_m$—. In a further embodiment, $L_2$ is —(CH$_2$)$_m$— and m represents 1 or 2. In one embodiment, $L_2$ is-O(CH$_2$)$_m$—. In another embodiment, $L_2$ is —O(CH$_2$)$_m$— and m represents 2. In a yet further embodiment, $L_2$ is —(CH$_2$)$_p$—NH—(CH$_2$)$_q$—. In another embodiment, $L_2$ is —(CH$_2$)$_p$—NH—(CH$_2$)$_q$— and p and q are both 1.

In respect of Formula (I), in one embodiment of the invention, $R_7$ is selected from hydrogen; hydroxy; $NR_{8a}R_{8b}$; $C_4$-$C_7$heterocycloalkyl optionally substituted with one $C_1$-$C_3$alkyl group; and $C_1$-$C_6$alkoxy optionally substituted with one $NR_{14a}R_{14b}$ group and phenyl optionally substituted with one to three groups independently selected from halo, methoxy and methyl.

In respect of Formula (I), in another embodiment, $R_7$ is hydrogen.

In one embodiment of the invention, $R_7$ is hydroxy.

In respect of Formula (I), in one embodiment of the invention, $R_7$ is $NR_{8a}R_{8b}$.

In another embodiment, $R_7$ is $C_4$-$C_7$heterocycloalkyl, optionally substituted with one or two $C_1$-$C_3$alkyl groups. In another embodiment, $R_7$ is morpholinyl or piperazinyl, optionally substituted with one or two $C_1$-$C_3$alkyl groups. In another embodiment, $R_7$ is morpholinyl or piperazinyl, substituted with one methyl group. In a further embodiment, $R_7$ is morpholinyl or piperazinyl.

In respect of Formula (I), in another embodiment, $R_7$ is $C_1$-$C_6$alkoxy, optionally substituted with one $NR_{14a}R_{14b}$ group. In another embodiment, $R_7$ methoxy optionally substituted with one $NR_{14a}R_{14b}$ group. In another embodiment, $R_7$ is methoxy.

In respect of Formula (I), in another embodiment, $R_7$ is phenyl optionally substituted with one to three groups independently selected from halo, methoxy and methyl. In another embodiment, $R_7$ is phenyl optionally substituted with one group which is methoxy.

In respect of Formula (I), in one embodiment of the invention, $R_2$ is Cy.

In respect of Formula (I), in one embodiment of the invention, Cy is selected from $C_4$-$C_7$heterocycloalkyl and $C_5$-$C_7$heterocycloalkenyl, each of which is optionally substituted with one to three groups independently selected from $C_1$-$C_3$alkyl, $C_4$-$C_7$heterocycloalkyl and $NR_{11a}R_{11b}$. In one embodiment of the invention, Cy is selected from $C_4$-$C_7$heterocycloalkyl and $C_5$-$C_7$heterocycloalkenyl, each of which is optionally substituted with one to three $C_1$-$C_3$alkyl groups. In one embodiment of the invention, Cy is selected from $C_4$-$C_7$heterocycloalkyl, and $C_5$-$C_7$heterocycloalkenyl, each of which is optionally substituted with one or two $C_1$-$C_3$alkyl groups, for example with one or two methyl groups.

In respect of Formula (I), in one embodiment of the invention, Cy is $C_4$-$C_7$heterocycloalkyl optionally substituted with one to three $C_1$-$C_3$alkyl groups. In another embodiment, Cy is $C_4$-$C_7$heterocycloalkyl. In another embodiment, Cy is morpholinyl, pyrrolidinyl, piperidinyl, tetrahydrofuranyl, oxazapenyl and tetrahydropyranyl, each of which is optionally substituted with one or two $C_1$-$C_3$alkyl groups. In another embodiment, Cy is morpholinyl, pyrrolidinyl, piperidinyl, tetrahydrofuranyl, oxazapenyl and tetrahydropyranyl, each of which is optionally substituted with one or two methyl groups. In another embodiment, Cy is morpholinyl, pyrrolidinyl, piperidinyl, tetrahydrofuranyl, oxazapenyl and tetrahydropyranyl. In one embodiment, Cy is morpholinyl.

In respect of Formula (I), in one embodiment of the invention, Cy is $C_5$-$C_7$heterocycloalkenyl optionally substituted with one to three $C_1$-$C_3$alkyl groups. In another embodiment, Cy is $C_4$-$C_7$heterocycloalkenyl. In another embodiment, Cy is dihydropyranyl optionally substituted with one to three $C_1$-$C_3$alkyl groups. In another embodiment, Cy is dihydropyranyl optionally substituted with one or two $C_1$-$C_3$alkyl groups. In another embodiment, Cy is dihydropyranyl.

In respect of Formula (I), in one embodiment of the invention, $R_2$ is X.

In respect of Formula (I), in one embodiment of the invention, X is selected from $C_1$-$C_6$alkyl and $C_2$-$C_6$alkenyl, each of which is optionally substituted with one to three groups independently selected from hydroxy, methoxy, halo, $NR_{13a}R_{13b}$ and $C_4$-$C_7$heterocycloalkyl, wherein $C_4$-$C_7$heterocycloalkyl is optionally substituted with one to three $C_1$-$C_3$alkyl groups. In another embodiment, X is selected from $C_1$-$C_6$alkyl and $C_2$-$C_6$alkenyl, each of which is optionally substituted with one group selected from hydroxy, methoxy and halo.

In respect of Formula (I), in one embodiment of the invention, X is $C_1$-$C_6$alkyl optionally substituted with one group selected from hydroxy, methoxy and halo. In another embodiment, X is $C_1$-$C_6$alkyl substituted with one hydroxy group. In another embodiment, X is $C_1$-$C_6$alkyl. In one embodiment, X is selected from n-propoxy, isopropoxy and isobutoxy, each of which is optionally substituted with one group selected from hydroxy, methoxy and halo. In another embodiment, X is selected from n-propoxy, isopropoxy and isobutoxy, each of which is optionally substituted with hydroxy. In one embodiment, X is selected from n-propoxy, isopropoxy and isobutoxy.

In respect of Formula (I), in one embodiment of the invention, X is $C_2$-$C_6$alkenyl optionally substituted with one group selected from hydroxy, methoxy and halo. In another embodiment, X is $C_2$-$C_6$alkenyl substituted with one hydroxy group. In another embodiment, X is $C_2$-$C_6$alkenyl. In another embodiment, X is isopropenyl or isobutenyl, each of which is optionally substituted with one group selected from hydroxy, methoxy and halo. In another embodiment, X is isopropenyl or isobutenyl, each of which is optionally substituted with hydroxy. In a further embodiment, X is isopropenyl or isobutenyl.

In respect of Formula (I), in one embodiment of the invention, $R_2$ is selected from morpholinyl, phenyl, pyrrolidin-1-yl, piperidin-1-yl, 2-methylmorpholinyl, (2S,6R)-2,6-dimethylmorpholinyl, isopropylamino, hydrogen, 1,4-oxazepan-4-yl, 3,6-dihydro-2H-pyran-4-yl, isopropyl, prop-1-en-2-yl, tetrahydro-2H-pyran-4-yl, 4-(2-morpholinoethyl)phenyl, (4-(morpholinomethyl)phenyl, 6-(dimethylamino)pyridin-3-yl, 3-(morpholinomethyl)phenyl, 2-(morpholinomethyl)phenyl, 4-(2-methoxyethoxy)phenyl, 1-hydroxyethyl, 3-hydroxypropyl, 2-morpholinopyridin-4-yl, 2-(2-methoxyethoxy)phenyl, 2-methoxyphenyl, pyridin-2-yl, isobutyl, 4-((dimethylamino)methyl)phenyl, 4-((methylamino)methyl)phenyl, 3-((dimethylamino)methyl)phenyl, 3-((methylamino)methyl)phenyl, 3-(((4-methoxybenzyl)amino)methyl)phenyl, acetyl, 2-methylprop-1-en-1-yl, tetrahydrofuran-2-carboxamido, (4-methoxybenzyl)amino, 4-hydroxyphenyl, isopropylcarbamate, methylcarbamate, piperazin-1-yl, 4-methylpiperazin-1-yl, cyclopropanecarboxamido, 4-((4-methylpiperazin-1-yl)methyl)phenyl and tetrahydrofuran-3-yl.

In respect of Formula (I), in one embodiment of the invention, $R_{5a}$ is selected from hydrogen and $C_1$-$C_6$alkyl. In another embodiment, $R_{5a}$ is $C_1$-$C_6$alkyl. In a further embodiment, $R_{5a}$ is selected from methyl and isopropyl.

In respect of Formula (I), in one embodiment of the invention, $R_{5b}$ is hydrogen.

In respect of Formula (I), in one embodiment of the invention, $R_{8a}$ and $R_{8b}$ are independently selected from hydrogen and methyl. In one embodiment, $R_{8a}$ is methyl and $R_{8b}$ is hydrogen. In another embodiment, $R_{8a}$ and $R_{8b}$ are both methyl.

In respect of Formula (I), in one embodiment of the invention, $R_9$ is selected from $C_1$-$C_6$alkyl and $C_3$-$C_7$cycloalkyl. In one embodiment, $R_9$ is $C_1$-$C_6$alkyl. In another embodiment, $R_9$ is selected from methyl and isopropyl. In one embodiment, $R_9$ is $C_3$-$C_7$cycloalkyl. In a further embodiment, $R_9$ is cyclopropyl.

In respect of Formula (I), in one embodiment of the invention, $R_{10a}$ and $R_{10b}$ are independently selected from hydrogen and methyl. In one embodiment, $R_{10a}$ and $R_{10b}$ are both methyl.

In respect of Formula (I), in one embodiment of the invention, $R_{11a}$ and $R_{11b}$ are independently selected from hydrogen and methyl.

In respect of Formula (I), in one embodiment of the invention, $R_{13a}$ and $R_{13b}$ are independently selected from hydrogen and methyl.

In respect of Formula (I), in one embodiment of the invention, $R_{14a}$ and $R_{14b}$ are independently selected from hydrogen and methyl.

In respect of Formula (I), in one embodiment of the invention, $R_{15a}$ is $C_1$-$C_6$alkyl. In another embodiment, $R_{15a}$ is methyl.

In one aspect of the invention, the compound of Formula (I) is selected from:

N-(4-fluoro-3-(2-morpholinoimidazo[1,2-b][1,2,4]triazin-6-yl)phenyl)pyrrolidine-1-carboxamide;
N-(4-fluoro-3-(2-phenylimidazo[1,2-b][1,2,4]triazin-6-yl)phenyl)pyrrolidine-1-carboxamide;
N-(4-fluoro-3-(2-(pyrrolidin-1-yl)imidazo[1,2-b][1,2,4]triazin-6-yl)phenyl)pyrrolidine-1-carboxamide;
N-(4-fluoro-3-(2-(piperidin-1-yl)imidazo[1,2-b][1,2,4]triazin-6-yl)phenyl)pyrrolidine-1-carboxamide;
(+,−)-N-(4-fluoro-3-(2-(2-methylmorpholino)imidazo[1,2-b][1,2,4]triazin-6-yl)phenyl)pyrrolidine-1-carboxamide;
N-(3-(2-((2S,6R)-2,6-dimethylmorpholino)imidazo[1,2-b][1,2,4]triazin-6-yl)-4-fluorophenyl)pyrrolidine-1-carboxamide;
N-(4-fluoro-3-(2-(isopropylamino)imidazo[1,2-b][1,2,4]triazin-6-yl)phenyl)pyrrolidine-1-carboxamide;
N-(4-fluoro-3-(imidazo[1,2-b][1,2,4]triazin-6-yl)phenyl)pyrrolidine-1-carboxamide;
N-(4-fluoro-3-(2-morpholinoimidazo[1,2-b][1,2,4]triazin-6-yl)phenyl)pyrrolidine-1-sulfonamide;
N-(3-(imidazo[1,2-b][1,2,4]triazin-6-yl)phenyl)furan-2-carboxamide;
N-(3-(2-(1,4-oxazepan-4-yl)imidazo[1,2-b][1,2,4]triazin-6-yl)-4-fluorophenyl)pyrrolidine-1-carboxamide;
N-(3-(2-(3,6-dihydro-2H-pyran-4-yl)imidazo[1,2-b][1,2,4]triazin-6-yl)-4-fluorophenyl)pyrrolidine-1-carboxamide;
N-(4-fluoro-3-(2-isopropylimidazo[1,2-b][1,2,4]triazin-6-yl)phenyl)pyrrolidine-1-carboxamide;
N-(4-fluoro-3-(2-(prop-1-en-2-yl)imidazo[1,2-b][1,2,4]triazin-6-yl)phenyl)pyrrolidine-1-carboxamide;
N-(4-fluoro-3-(2-(tetrahydro-2H-pyran-4-yl)imidazo[1,2-b][1,2,4]triazin-6-yl)phenyl)pyrrolidine-1-carboxamide;
N-(3-(2-(6-(dimethylamino)pyridin-3-yl)imidazo[1,2-b][1,2,4]triazin-6-yl)-4-fluorophenyl)pyrrolidine-1-carboxamide;
N-(4-fluoro-3-(2-(4-(2-morpholinoethoxy)phenyl)imidazo[1,2-b][1,2,4]triazin-6-yl)phenyl)pyrrolidine-1-carboxamide;
N-(4-fluoro-3-(2-(4-(morpholinomethyl)phenyl)imidazo[1,2-b][1,2,4]triazin-6-yl)phenyl)pyrrolidine-1-carboxamide;
N-(4-fluoro-3-(2-(3-(morpholinomethyl)phenyl)imidazo[1,2-b][1,2,4]triazin-6-yl)phenyl)pyrrolidine-1-carboxamide;
N-(4-fluoro-3-(2-(2-(morpholinomethyl)phenyl)imidazo[1,2-b][1,2,4]triazin-6-yl)phenyl)pyrrolidine-1-carboxamide;
N-(4-fluoro-3-(2-(4-(2-methoxyethoxy)phenyl)imidazo[1,2-b][1,2,4]triazin-6-yl)phenyl)pyrrolidine-1-carboxamide;
N-(4-fluoro-3-(2-(4-(2-morpholinoethyl)phenyl)imidazo[1,2-b][1,2,4]triazin-6-yl)phenyl)pyrrolidine-1-carboxamide;
(+,−)-N-(4-fluoro-3-(2-(tetrahydrofuran-3-yl)imidazo[1,2-b][1,2,4]triazin-6-yl)phenyl)pyrrolidine-1-carboxamide;
(+,−)-N-(4-fluoro-3-(2-(1-hydroxyethyl)imidazo[1,2-b][1,2,4]triazin-6-yl)phenyl)pyrrolidine-1-carboxamide;
N-(4-fluoro-3-(2-(3-hydroxypropyl)imidazo[1,2-b][1,2,4]triazin-6-yl)phenyl)pyrrolidine-1-carboxamide;
N-(4-fluoro-3-(2-(2-morpholinopyridin-4-yl)imidazo[1,2-b][1,2,4]triazin-6-yl)phenyl)pyrrolidine-1-carboxamide;
N-(4-fluoro-3-(3-methyl-6-morpholinoimidazo[1,2-a]pyrimidin-2-yl)phenyl)pyrrolidine-1-carboxamide;
N-(3-(3-methyl-6-morpholinoimidazo[1,2-a]pyrimidin-2-yl)phenyl)pyrrolidine-1-carboxamide;
N-(4-fluoro-3-(2-(2-(2-methoxyethoxy)phenyl)imidazo[1,2-b][1,2,4]triazin-6-yl)phenyl)pyrrolidine-1-carboxamide;
N-(4-fluoro-3-(2-(2-methoxyphenyl)imidazo[1,2-b][1,2,4]triazin-6-yl)phenyl)pyrrolidine-1-carboxamide;
N-(4-cyano-3-(2-morpholinoimidazo[1,2-b][1,2,4]triazin-6-yl)phenyl)pyrrolidine-1-carboxamide;
N-(4-fluoro-3-(2-morpholinoimidazo[1,2-b][1,2,4]triazin-6-yl)phenyl)-N',N'-dimethylsulfamide;
N-(4-fluoro-3-(2-morpholinoimidazo[1,2-b][1,2,4]triazin-6-yl)phenyl)cyclopentanesulfonamide;
N-(4-fluoro-3-(2-morpholinoimidazo[1,2-b][1,2,4]triazin-6-yl)phenyl)-1,3-dimethyl-1H-pyrazole-4-sulfonamide;
N-(4-fluoro-3-(2-(pyridin-2-yl)imidazo[1,2-b][1,2,4]triazin-6-yl)phenyl)pyrrolidine-1-carboxamide;
N-(4-fluoro-3-(2-isobutylimidazo[1,2-b][1,2,4]triazin-6-yl)phenyl)pyrrolidine-1-carboxamide;
N-(3-(2-(4-((dimethylamino)methyl)phenyl)imidazo[1,2-b][1,2,4]triazin-6-yl)-4-fluorophenyl)pyrrolidine-1-carboxamide;
N-(4-fluoro-3-(2-(4-((methylamino)methyl)phenyl)imidazo[1,2-b][1,2,4]triazin-6-yl)phenyl)pyrrolidine-1-carboxamide;
N-(4-fluoro-3-(2-(4-(2-morpholinoethyl)phenyl)imidazo[1,2-b][1,2,4]triazin-6-yl)phenyl)pyrrolidine-1-carboxamide
N-(4-fluoro-3-(7-fluoro-2-morpholinoimidazo[1,2-b][1,2,4]triazin-6-yl)phenyl)pyrrolidine-1-carboxamide;
N-(3-(2-(3-((dimethylamino)methyl)phenyl)imidazo[1,2-b][1,2,4]triazin-6-yl)-4-fluorophenyl)pyrrolidine-1-carboxamide;
N-(4-fluoro-3-(2-morpholinoimidazo[1,2-b][1,2,4]triazin-6-yl)phenyl)azetidine-1-carboxamide;
N-(4-chloro-3-(2-morpholinoimidazo[1,2-b][1,2,4]triazin-6-yl)phenyl)pyrrolidine-1-carboxamide;
N-(4-fluoro-3-(2-(3-((methylamino)methyl)phenyl)imidazo[1,2-b][1,2,4]triazin-6-yl)phenyl)pyrrolidine-1-carboxamide;
N-(4-fluoro-3-(2-(3-(((4-methoxybenzyl)amino)methyl)phenyl)imidazo[1,2-b][1,2,4]triazin-6-yl)phenyl)pyrrolidine-1-carboxamide;
N-(3-(2-acetylimidazo[1,2-b][1,2,4]triazin-6-yl)-4-fluorophenyl)pyrrolidine-1-carboxamide;
N-(4-fluoro-3-(2-(2-methylprop-1-en-1-yl)imidazo[1,2-b][1,2,4]triazin-6-yl)phenyl)pyrrolidine-1-carboxamide;
isopropyl(4-fluoro-3-(2-morpholinoimidazo[1,2-b][1,2,4]triazin-6-yl)phenyl)carbamate;
N-(4-fluoro-3-(2-(tetrahydrofuran-2-carboxamido)imidazo[1,2-b][1,2,4]triazin-6-yl)phenyl)pyrrolidine-1-carboxamide;
N-(4-fluoro-3-(2-((4-methoxybenzyl)amino)imidazo[1,2-b][1,2,4]triazin-6-yl)phenyl)pyrrolidine-1-carboxamide;

N-(4-fluoro-3-(2-(4-hydroxyphenyl)imidazo[1,2-b][1,2,4]triazin-6-yl)phenyl)pyrrolidine-1-carboxamide;

ethyl (4-fluoro-3-(2-morpholinoimidazo[1,2-b][1,2,4]triazin-6-yl)phenyl)carbamate N-(4-fluoro-3-(2-morpholinoimidazo[1,2-b][1,2,4]triazin-6-yl)phenyl)-3,5-dimethylisoxazole-4-sulfonamide;

isopropyl(6-(2-fluoro-5-(pyrrolidine-1-carboxamido)phenyl)imidazo[1,2-b][1,2,4]triazin-2-yl)carbamate;

methyl (6-(2-fluoro-5-(pyrrolidine-1-carboxamido)phenyl)imidazo[1,2-b][1,2,4]triazin-2-yl)carbamate;

N-(4-fluoro-3-(2-(piperazin-1-yl)imidazo[1,2-b][1,2,4]triazin-6-yl)phenyl)pyrrolidine-1-carboxamide;

N-(4-fluoro-3-(2-(4-methylpiperazin-1-yl)imidazo[1,2-b][1,2,4]triazin-6-yl)phenyl)pyrrolidine-1-carboxamide;

N-(3-(2-(cyclopropanecarboxamido)imidazo[1,2-b][1,2,4]triazin-6-yl)-4-fluorophenyl)pyrrolidine-1-carboxamide;

N-(4-fluoro-3-(2-(4-((4-methylpiperazin-1-yl)methyl)phenyl)imidazo[1,2-b][1,2,4]triazin-6-yl)phenyl)pyrrolidine-1-carboxamide;

or a salt thereof.

In another aspect of the invention, the compound of Formula (I) or Formula (IA) is selected from:

N-(4-fluoro-3-(2-morpholinoimidazo[1,2-b][1,2,4]triazin-6-yl)phenyl)pyrrolidine-1-carboxamide;

N-(4-fluoro-3-(2-phenylimidazo[1,2-b][1,2,4]triazin-6-yl)phenyl)pyrrolidine-1-carboxamide;

N-(4-fluoro-3-(2-(pyrrolidin-1-yl)imidazo[1,2-b][1,2,4]triazin-6-yl)phenyl)pyrrolidine-1-carboxamide;

N-(4-fluoro-3-(2-(piperidin-1-yl)imidazo[1,2-b][1,2,4]triazin-6-yl)phenyl)pyrrolidine-1-carboxamide;

(+,−)-N-(4-fluoro-3-(2-(2-methylmorpholino)imidazo[1,2-b][1,2,4]triazin-6-yl)phenyl)pyrrolidine-1-carboxamide;

N-(3-(2-((2S,6R)-2,6-dimethylmorpholino)imidazo[1,2-b][1,2,4]triazin-6-yl)-4-fluorophenyl)pyrrolidine-1-carboxamide;

N-(4-fluoro-3-(2-(isopropylamino)imidazo[1,2-b][1,2,4]triazin-6-yl)phenyl)pyrrolidine-1-carboxamide;

N-(4-fluoro-3-(imidazo[1,2-b][1,2,4]triazin-6-yl)phenyl)pyrrolidine-1-carboxamide;

N-(4-fluoro-3-(2-morpholinoimidazo[1,2-b][1,2,4]triazin-6-yl)phenyl)pyrrolidine-1-sulfonamide;

N-(3-(imidazo[1,2-b][1,2,4]triazin-6-yl)phenyl)furan-2-carboxamide;

N-(3-(2-(1,4-oxazepan-4-yl)imidazo[1,2-b][1,2,4]triazin-6-yl)-4-fluorophenyl)pyrrolidine-1-carboxamide;

N-(3-(2-(3,6-dihydro-2H-pyran-4-yl)imidazo[1,2-b][1,2,4]triazin-6-yl)-4-fluorophenyl)pyrrolidine-1-carboxamide;

N-(4-fluoro-3-(2-isopropylimidazo[1,2-b][1,2,4]triazin-6-yl)phenyl)pyrrolidine-1-carboxamide;

N-(4-fluoro-3-(2-(prop-1-en-2-yl)imidazo[1,2-b][1,2,4]triazin-6-yl)phenyl)pyrrolidine-1-carboxamide;

N-(4-fluoro-3-(2-(tetrahydro-2H-pyran-4-yl)imidazo[1,2-b][1,2,4]triazin-6-yl)phenyl)pyrrolidine-1-carboxamide;

N-(3-(2-(6-(dimethylamino)pyridin-3-yl)imidazo[1,2-b][1,2,4]triazin-6-yl)-4-fluorophenyl)pyrrolidine-1-carboxamide;

N-(4-fluoro-3-(2-(4-(2-morpholinoethoxy)phenyl)imidazo[1,2-b][1,2,4]triazin-6-yl)phenyl)pyrrolidine-1-carboxamide;

N-(4-fluoro-3-(2-(4-(morpholinomethyl)phenyl)imidazo[1,2-b][1,2,4]triazin-6-yl)phenyl)pyrrolidine-1-carboxamide;

N-(4-fluoro-3-(2-(3-(morpholinomethyl)phenyl)imidazo[1,2-b][1,2,4]triazin-6-yl)phenyl)pyrrolidine-1-carboxamide;

N-(4-fluoro-3-(2-(2-(morpholinomethyl)phenyl)imidazo[1,2-b][1,2,4]triazin-6-yl)phenyl)pyrrolidine-1-carboxamide;

N-(4-fluoro-3-(2-(4-(2-methoxyethoxy)phenyl)imidazo[1,2-b][1,2,4]triazin-6-yl)phenyl)pyrrolidine-1-carboxamide;

N-(4-fluoro-3-(2-(4-(2-morpholinoethyl)phenyl)imidazo[1,2-b][1,2,4]triazin-6-yl)phenyl)pyrrolidine-1-carboxamide;

N-(4-fluoro-3-(2-(tetrahydrofuran-3-yl)imidazo[1,2-b][1,2,4]triazin-6-yl)phenyl)pyrrolidine-1-carboxamide;

N-(4-fluoro-3-(2-(1-hydroxyethyl)imidazo[1,2-b][1,2,4]triazin-6-yl)phenyl)pyrrolidine-1-carboxamide;

N-(4-fluoro-3-(2-(3-hydroxypropyl)imidazo[1,2-b][1,2,4]triazin-6-yl)phenyl)pyrrolidine-1-carboxamide;

N-(4-fluoro-3-(2-(2-morpholinopyridin-4-yl)imidazo[1,2-b][1,2,4]triazin-6-yl)phenyl)pyrrolidine-1-carboxamide;

N-(4-fluoro-3-(3-methyl-6-morpholinoimidazo[1,2-a]pyrimidin-2-yl)phenyl)pyrrolidine-1-carboxamide;

N-(3-(3-methyl-6-morpholinoimidazo[1,2-a]pyrimidin-2-yl)phenyl)pyrrolidine-1-carboxamide;

N-(4-fluoro-3-(2-(2-(2-methoxyethoxy)phenyl)imidazo[1,2-b][1,2,4]triazin-6-yl)phenyl)pyrrolidine-1-carboxamide;

N-(4-fluoro-3-(2-(2-methoxyphenyl)imidazo[1,2-b][1,2,4]triazin-6-yl)phenyl)pyrrolidine-1-carboxamide;

N-(4-cyano-3-(2-morpholinoimidazo[1,2-b][1,2,4]triazin-6-yl)phenyl)pyrrolidine-1-carboxamide;

N-(4-fluoro-3-(2-morpholinoimidazo[1,2-b][1,2,4]triazin-6-yl)phenyl)-N',N'-dimethylsulfamide;

N-(4-fluoro-3-(2-morpholinoimidazo[1,2-b][1,2,4]triazin-6-yl)phenyl)cyclopentanesulfonamide;

N-(4-fluoro-3-(2-morpholinoimidazo[1,2-b][1,2,4]triazin-6-yl)phenyl)-1,3-dimethyl-1H-pyrazole-4-sulfonamide;

or a salt thereof.

Compound Preparation

A compound of Formula (I) and salts thereof, may be prepared by the methodology described hereinafter, constituting further aspects of this invention.

The general procedures which can be used to synthesise a compound of Formula (I) are summarised in reaction Schemes 1 and 2 and are illustrated in the Examples.

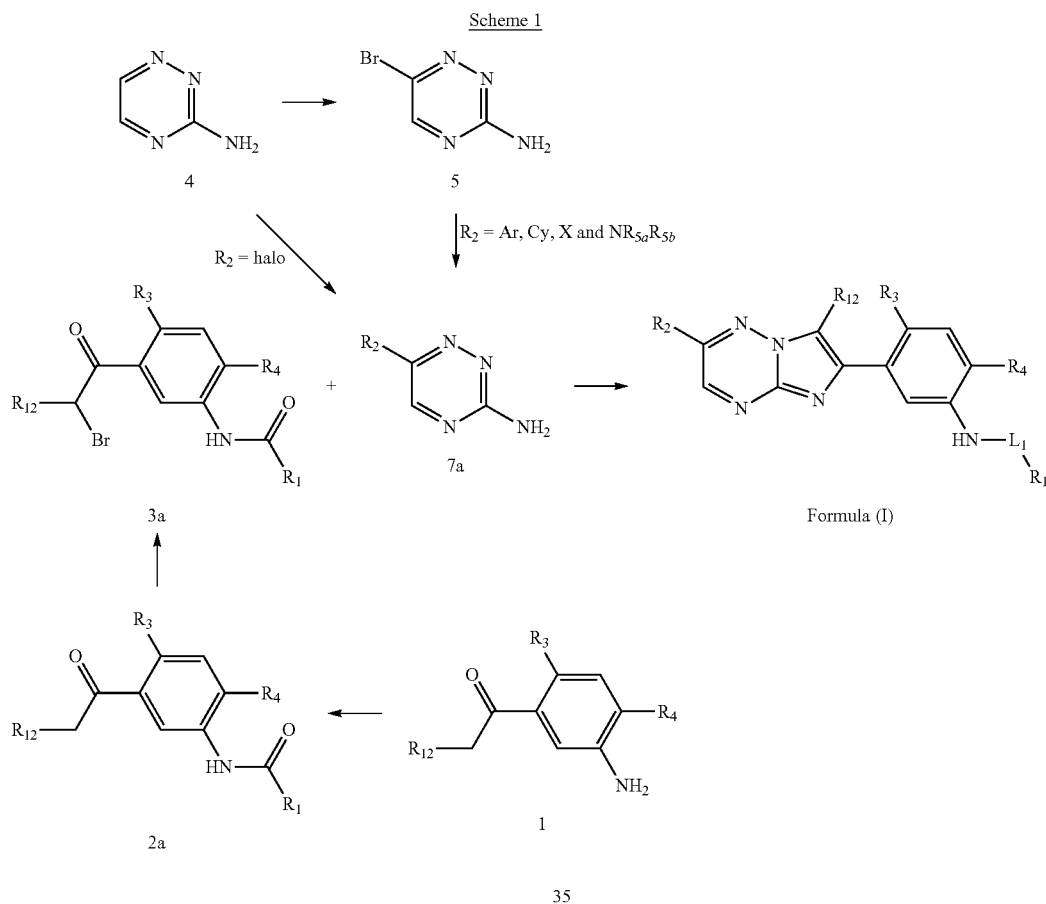

Scheme 1

Compounds of Formula (I), wherein $L_1$ is —C(O)—, $R_{12}$ halo and $R_3$ and $R_4$ are independently hydrogen or halo, can be made from compounds of Formula (I), wherein $L_1$ is —C(O)—, $R_{12}$ is hydrogen and $R_3$ and $R_4$ are independently hydrogen or halo, by a halogenation reaction, for example fluorination using a suitable reagent such as DAST.

Compounds of Formula (I), wherein $L_1$ is —C(O)—, $R_{12}$ is hydrogen or methyl, and $R_3$ and $R_4$ are independently hydrogen or halo, may be obtained by reacting compounds of Formula 3a, wherein $R_1$ is as defined for Formula (I), $R_{12}$ is hydrogen or methyl and $R_3$ and $R_4$ are independently hydrogen or halo, with compounds of Formula 7a, wherein $R_2$ is as defined for Formula (I), in a suitable solvent, such as ethanol, at elevated temperature, such as 60° C., for example over a period of 3-6 days.

Compounds of Formula 3a may be obtained by a bromination reaction of compounds of Formula 2a, wherein $R_1$ is as defined for Formula (I), $R_{12}$ is hydrogen or methyl and $R_3$ and $R_4$ are independently hydrogen or halo. Compounds 2a may be treated with a brominating agent such as trimethyl (phenyl)ammonium tribromide in a suitable solvent such as THF, for example over 24 h.

Compounds of Formula 2a may be obtained by reaction of compound 1, wherein $R_{12}$ is hydrogen or methyl and $R_3$ and $R_4$ are independently hydrogen or halo, with $R_1C(O)Cl$, wherein $R_1$ is as defined for Formula (I), in a suitable solvent such as DCM:pyridine, wherein pyridine is both a co-solvent and a base, or using a base such as DMAP in a suitable solvent, such as DCM or acetonitrile, over a period of several days, for example 3 days.

The compound of Formula 1, wherein $R_3$ is fluoro and $R_{12}$ and $R_4$ are hydrogen, is available for purchase from APOLLO. Other compounds of Formula 1 are either commercially available or made according to standard procedures.

$R_1C(O)Cl$ may either be commercially available or can be made using standard procedures, for example from $R_1C(O)OH$, which may be commercially available.

Compounds of Formula 7a, wherein $R_2$ is hydrogen, is a compound of Formula 4 which is available for purchase from APOLLO.

Compounds of Formula 7a, wherein $R_2$ is halo, are either commercially available or may be obtained by a halogenation reaction of compound 4, for example: bromination using a suitable agent such as N-bromosuccinimide; chlorination using a suitable agent such as N-chlorosuccinimide; in a suitable solvent such as dioxane.

Compounds of Formula 7a, wherein $R_2$ is Ar, $C_4$-$C_7$heterocycloalkyl, $C_5$-$C_7$heterocycloalkenyl, may be obtained by reaction of compound 7a, wherein halo is bromo (shown as compound 5 in Scheme 1), with $R_2$—Y, wherein $R_2$ is Ar, $C_4$-$C_7$heterocycloalkyl, $C_5$-$C_7$heterocycloalkenyl, and Y is hydrogen or a boronic acid or ester, for example tetrafluoroborate.

For example, when $R_2$—Y is morpholine, pyrrolidine or piperidine (Y is hydrogen), reaction with compound 5 may be carried out by means of sonication.

For example, when $R_2$—Y is $HNR_{51}R_{5b}$, reaction with compound 5 may be carried out using a coupling reaction in the presence of a palladium agent such as Tris(dibenzylideneacetone)dipalladium(0) and a suitable base, such as lithium bis(trimethylsilyl)amide and a suitable ligand, for example palladium(ii) phenethylamine chloride, in a solvent such as THF.

For example, when $R_2$—Y is X—H, reaction with compound 5 may be carried out by means of a coupling reaction, in the presence of a suitable palladium agent, such as palladium acetate.

Compounds of Formula 7a, wherein $R_2$ is Ar or Cy, may alternatively be obtained by a coupling reaction of compound 5 with $R_2$—Z, wherein $R_2$ is Ar or Cy, and Z is a suitable leaving group, for example when $R_2$ is Ar, Z may be the leaving group tetramethyl-dioxaborolane, in the presence of a suitable coupling reagent, for example Pd(dppf)Cl$_2$.DCM or [1,1'-Bis(diphenylphosphino)ferrocene]dichloro-palladium(II) under elevated temperature (e.g. 80° C.).

Compounds $R_2$—Y and $R_2$—Z may either be purchased, for example from ALDRICH or can be made using standard procedures. For example when Z is a leaving group such as a borolane, $R_2$—Z can be made via $R_2$—Li, which in turn can be made from $R_2$—Br or $R_2$—Cl which may be commercially available.

As noted above, compound 5 is commercially available (e.g. from ENAMINE) or it may be obtained by a bromination reaction of compound 4 using a suitable brominating agent such as N-bromosuccinimide in a suitable solvent such as dioxane.

Compound 4 is available for purchase from APOLLO.

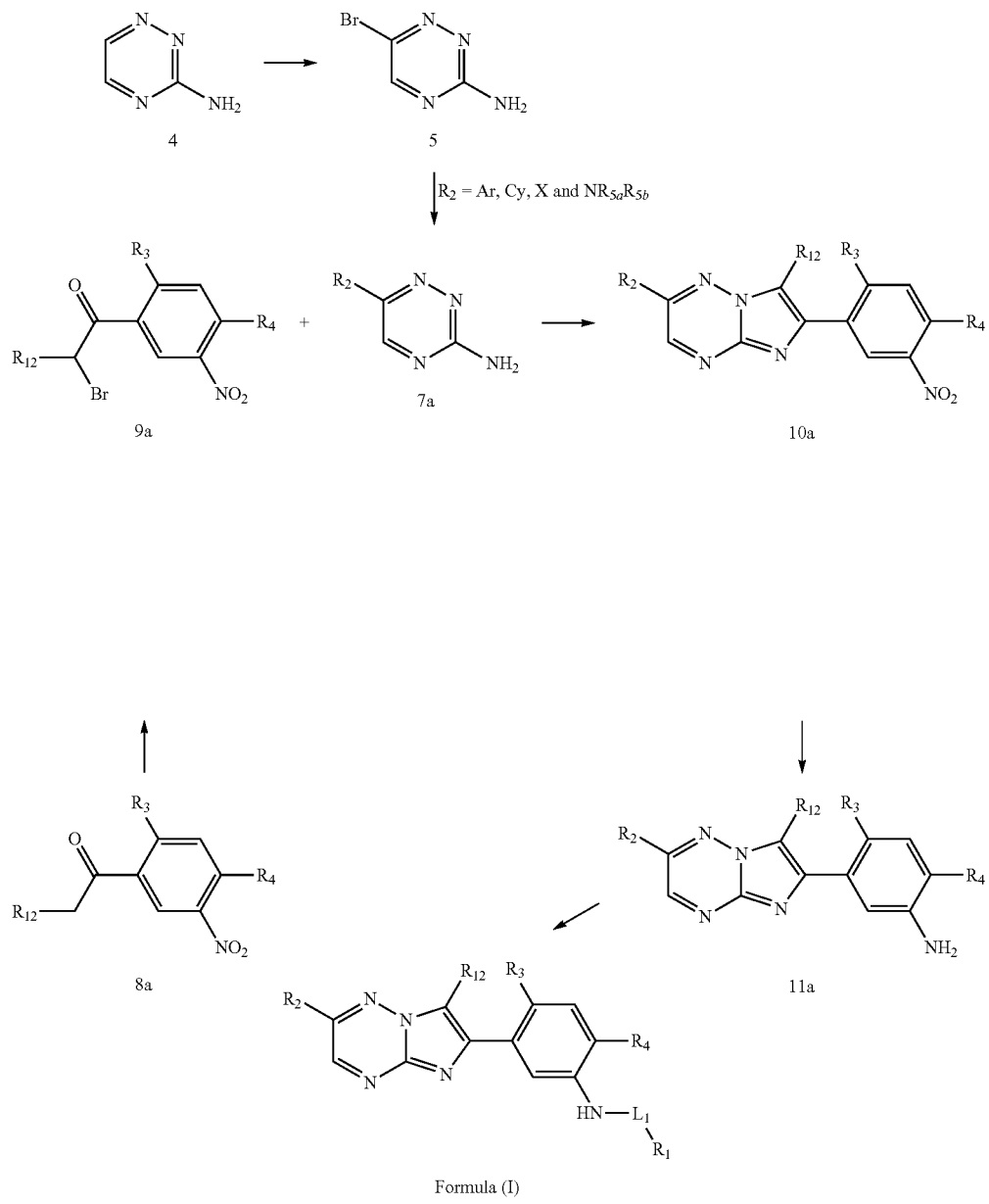

Compounds of Formula (I), wherein $R_{12}$ is halo, can be made from compounds of Formula (I), wherein $R_{12}$ is hydrogen, by a halogenation reaction, for example fluorination using a suitable reagent such as DAST.

Compounds of Formula (I), wherein $R_{12}$ is hydrogen or methyl, may be obtained by reacting compounds of Formula 11a, wherein $R_{12}$ is hydrogen or methyl and $R_2$, $R_3$ and $R_4$ are as defined for Formula (I), with $R_1(L_1)Cl$, wherein $L_1$ is as defined for Formula (I), in a suitable solvent such as DCM:pyridine, wherein pyridine is both a co-solvent and a base, or using a base such as DMAP in a suitable solvent, such as DCM or acetonitrile, over a period of several days, for example 3 days.

$R_1(L_1)Cl$ may either be commercially available or can be made using standard procedures, for example from $R_1C(O)OH$, which in turn is either commercially available or can be made using standard procedures.

Compounds of Formula 11a may be prepared by the hydrogenation of compounds of Formula 10a, wherein $R_2$ is other than halo, $R_{12}$ is hydrogen or methyl and $R_2$, $R_3$ and $R_4$ are as defined for Formula (I). For compounds of Formula 10a wherein $R_2$ is other than halo (i.e. $R_2$ is selected from hydrogen, Ar, Cy, X and $NR_{5a}R_{5b}$), hydrogenation may be carried out with hydrogen gas under pressure in the presence of a suitable catalyst e.g. a raney nickel catalyst or a palladium catalyst such as palladium on activated charcoal. For compounds of Formula 10a wherein $R_2$ is halo, hydrogenation may be carried out in the presence of hydrogen gas, in the presence of a suitable catalyst such as Fe/NH$_4$Cl.

Compounds of Formula 10a may be obtained by reacting compounds of Formula 9a, wherein $R_{12}$ is hydrogen or methyl and $R_3$ and $R_4$ are as defined for Formula (I), with compounds of Formula 7a, wherein $R_2$ is other than halo, in a suitable solvent, such as ethanol or acetonitrile, at elevated temperature, such as 60° C., for example over a period of 3-6 days.

Compounds of Formula 9a may be obtained by a bromination reaction of compounds of Formula 8a, wherein $R_{12}$ is hydrogen or methyl and $R_3$ and $R_4$ are as defined for Formula (I). Compounds of Formula 8a may be treated with a brominating agent such as trimethyl(phenyl)ammonium tribromide or N-bromosuccinimide in a suitable solvent such as THF or acetonitrile, for example over 24 h.

Compounds of Formula 8a may either be commercially available or can be made using standard procedures. For example, the compound of Formula 8a, wherein $R_3$ is fluoro and $R_4$ and $R_{12}$ are hydrogen, may be purchased from ENAMINE.

Examples of protecting groups that may be employed in the synthetic routes described herein and the means for their removal can be found in T. W. Greene *'Protective Groups in Organic Synthesis'*, 4th Edition, J. Wiley and Sons, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulphate, or anhydrous sodium sulphate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times temperatures may typically be determined by reaction-monitoring techniques, for example thin-layer chromatography and LC-MS.

Individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

METHODS OF USE

It will be appreciated by those skilled in the art that references herein to treatment refer to the treatment of established conditions. However, the compounds of Formula (I) and pharmaceutically acceptable salts thereof may, depending on the condition, also be useful in the prevention of certain diseases. Thus, in one embodiment, there is provided the treatment or prevention of a disease. In another embodiment, there is provided the treatment of a disease. In a further embodiment, there is provided the prevention of a disease.

There is thus provided as a further aspect of the invention a compound of Formula (I), or a pharmaceutically acceptable salt thereof, for use in therapy.

It will be appreciated that, when a compound of Formula (I) or a pharmaceutically acceptable salt thereof is used in therapy, it is used as an active therapeutic agent.

There is also therefore provided a compound of Formula (I), or a pharmaceutically acceptable salt thereof, for use in the treatment or prevention of a parasitic disease, for example Chagas disease, Human African Trypanosomiasis or leishmaniasis, particularly visceral leishmaniasis. There is further provided a compound of Formula (I), or a pharmaceutically acceptable salt thereof, for use in the treatment or prevention of Chagas disease. There is also provided a compound of Formula (I), or a pharmaceutically acceptable salt thereof, for use in the treatment or prevention visceral leishmaniasis. There is further provided a compound of Formula (I), or a pharmaceutically acceptable salt thereof, for use in the treatment or prevention of Chagas disease. There is also provided a compound of Formula (I), or a pharmaceutically acceptable salt thereof, for use in the treatment or prevention of Human African Trypanosomiasis. There is further provided the use of a compound of Formula (I), or a pharmaceutically acceptable salt thereof, in the manufacture of a medicament for the treatment or prevention of a parasitic disease, for example Chagas disease, Human African Trypanosomiasis or leishmaniasis, particularly visceral leishmaniasis. There is also provided the use of a compound of Formula (I), or a pharmaceutically acceptable salt thereof, in the manufacture of a medicament for the treatment or prevention of leishmaniasis. There is further provided the use of a compound of Formula (I), or a pharmaceutically acceptable salt thereof, in the manufacture of a medicament for the treatment or prevention of visceral leishmaniasis. There is also provided the use of a compound of Formula (I), or a pharmaceutically acceptable salt thereof, in the manufacture of a medicament for the treatment or prevention of Chagas disease. There is further provided the use of a compound of Formula (I), or a pharmaceutically acceptable salt thereof, in the manufacture of a medicament for the treatment or prevention of Human African Trypanosomiasis. There is further provided a method of treatment or prevention of a parasitic disease, for example Chagas disease, Human African Trypanosomiasis or leishmaniasis, particularly visceral leishmaniasis, which method comprises administering to a human subject in need thereof, a therapeutically effective amount of a compound of Formula (I), or a pharmaceutically acceptable salt thereof. There is also provided a method of treatment or prevention of leishmaniasis, which method comprises administering to a human subject in need thereof, a therapeutically effective amount of a compound of Formula (I), or a pharmaceutically acceptable salt thereof. There is further provided a method of treatment or prevention of visceral leishmaniasis, which method comprises administering to a human subject in need thereof, a therapeutically effective amount of a compound of Formula (I), or a pharmaceutically acceptable salt thereof. There is also provided a method of treatment or prevention of Chagas disease, which method comprises administering to a human subject in need thereof, a therapeutically effective amount of a compound of Formula (I), or a pharmaceutically acceptable salt thereof. There is further provided a method of treatment or prevention of a Human African Trypanosomiasis, which method comprises administering to a human subject in need thereof, a therapeutically effective amount of a compound of Formula (I), or a pharmaceutically acceptable salt thereof.

There is also therefore provided N-(4-fluoro-3-(2-morpholinoimidazo[1,2-b][1,2,4]triazin-6-yl)phenyl)pyrrolidine-1-carboxamide, or a pharmaceutically acceptable salt thereof, for use in the treatment or prevention of a parasitic disease, for example Chagas disease, Human African Trypanosomiasis or leishmaniasis, particularly visceral leishmaniasis.

There is further provided the use of N-(4-fluoro-3-(2-morpholinoimidazo[1,2-b][1,2,4]triazin-6-yl)phenyl)pyrrolidine-1-carboxamide, or a pharmaceutically acceptable salt thereof, in the manufacture of a medicament for the treatment or prevention of a parasitic disease, for example Chagas disease, Human African Trypanosomiasis or leishmaniasis, particularly visceral leishmaniasis.

There is further provided a method of treatment or prevention of a parasitic disease, for example Chagas disease, Human African Trypanosomiasis or leishmaniasis, particularly visceral leishmaniasis, which method comprises administering to a human subject in need thereof, a therapeutically effective amount of N-(4-fluoro-3-(2-morpholinoimidazo[1,2-b][1,2,4]triazin-6-yl)phenyl)pyrrolidine-1-carboxamide, or a pharmaceutically acceptable salt thereof.

COMPOSITIONS AND FORMULATIONS

While it is possible that, for use in the methods of the invention, a compound of Formula (I) or a pharmaceutically acceptable salt thereof may be administered as the bulk substance, it is usually preferable to present the active ingredient in a pharmaceutical formulation, for example, wherein the agent is in admixture with at least one pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise, in addition to the carrier, any suitable binder(s), lubricant(s), suspending agent(s), coating agent(s), and/or solubilizing agent(s).

The phrase "pharmaceutically acceptable", as used herein, refers to salts, molecular entities and other ingredients of compositions that are generally physiologically tolerable and do not typically produce untoward reactions when administered to a mammal (e.g., human). Suitably, as used herein, the term "pharmaceutically acceptable" means approved by a regulatory agency of the Federal or a state government for use in mammals, and more particularly in humans, or listed in the U.S. Pharmacopoeia or other generally recognized texts, for example the International Union of Pure and Applied Chemistry (IUPAC) Handbook of Pharmaceutical Salts, 2011 Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine, by analogy with formulation of antibacterials, such as anti-tubercular agents, or formulation of antimalarial agents.

The compounds of the invention will normally, but not necessarily, be formulated into pharmaceutical compositions prior to administration to a patient. In one aspect, the invention is directed to a pharmaceutical composition comprising a compound of Formula (I), or a pharmaceutically acceptable salt thereof. In another aspect the invention is directed to a pharmaceutical composition comprising a compound of Formula (I), or a pharmaceutically acceptable salt thereof, together with at least one pharmaceutically acceptable carrier. The carrier must be "acceptable" in the sense of being compatible with the other ingredients of the formulation and not deleterious to the recipient thereof.

A therapeutically effective amount of the compound of the present invention can be determined by methods known in the art. The therapeutically effective quantities will depend on the age and on the general physiological condition of the subject, the route of administration and the pharmaceutical formulation used. The therapeutic doses will generally be between about 1 and 2000 mg/day, for example between about 500 and 2000 mg/day. The daily dose as employed for human treatment will range from 1 to 2000 mg, which may be administered in one or two daily doses, for example, depending on the route of administration and the condition of the subject. When the composition comprises dosage units, each unit will contain 1 mg to 2 g of active ingredient. When the dosage form is a tablet, the total weight of the tablet is suitably 1000 mg or lower.

The present invention is further related to a pharmaceutical composition comprising a compound of Formula (I), or a pharmaceutically acceptable salt thereof.

The present invention is further related to a pharmaceutical composition for the treatment of a parasitic disease, for example Chagas disease, Human African Trypanosomiasis or leishmaniasis, particularly visceral leishmaniasis, comprising a compound of Formula (I) or a pharmaceutically acceptable salt thereof.

The present invention is yet further related to a pharmaceutical composition comprising a compound of Formula (I), or a pharmaceutically acceptable salt thereof together with at least one pharmaceutically acceptable carrier.

The present invention is even further related to a pharmaceutical composition comprising a) a compound of Formula (I) or a pharmaceutically acceptable salt thereof, and b) a pharmaceutically acceptable carrier or excipient.

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more (at least one) pharmaceutically acceptable carriers or excipients. In one aspect, the pharmaceutical composition is formulated for oral administration.

The pharmaceutical compositions of the invention include those in a form adapted for oral use in mammals including humans.

The pharmaceutical compositions of the invention include those in a form adapted for oral use and may be used for the treatment of a parasitic disease, for example Chagas disease, Human African Trypanosomiasis or leishmaniasis, particularly visceral leishmaniasis, in mammals including humans.

The compound of the invention can be administered for immediate-, delayed-, modified-, sustained-, pulsed- or controlled-release applications.

The composition may be formulated for administration by any convenient route. For the treatment of a parasitic disease, for example Chagas disease, Human African Trypanosomiasis or leishmaniasis, particularly visceral leishmaniasis, the compositions may be in the form of tablets, capsules, powders, granules, lozenges, aerosols or liquid preparations, for oral use.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

A compound of Formula (I), or a pharmaceutically acceptable salt thereof, may be the sole therapeutic agent in the compositions of the invention, or it may be present in the formulation in combination with one or more (at least one) additional therapeutic agents.

The invention thus provides in a further aspect, a combination comprising (a) a compound of Formula (I), or a pharmaceutically acceptable salt thereof, and (b) at least one additional therapeutic agent. The combination optionally further comprises at least one pharmaceutically acceptable carrier. In one aspect of the invention there is provided a pharmaceutical composition comprising a compound of Formula (I), or a pharmaceutically acceptable salt thereof, together with at least one pharmaceutically acceptable carrier and one or more (at least one) additional therapeutic agents.

Examples of such one or more (at least one) additional therapeutic agents are anti-*leishmania* agents, including, but not limited to, miltefosine, paromomycin, sodium stibugluconate, meglumine antimoniate, amphotericin B deoxycholate or liposomal amphotericin B. In one aspect of the invention for oral treatment the additional therapeutic agent is miltefosine. Such chemotherapy is determined by the judgment of the treating physician using preferred drug combinations. In addition to the aforementioned, future anti-*leishmania* therapeutic agents emerging from clinical studies may also be employed as the one or more (at least one) additional therapeutic agents in a combination with a compound of Formula (I).

In another aspect, the invention provides a combination comprising a compound of Formula (I) or a pharmaceutically acceptable salt thereof, together with one or more (at least one) additional therapeutic agents, such as an antiparasitic agent, an anti-AIDS or anti-HIV agent, or an anti-TB agent.

In a further aspect, the one or more (at least one) additional therapeutic agent is, for example, an agent useful for the treatment of a parasitic disease in a mammal, a therapeutic vaccine, an anti-TB agent or an agent for the treatment of HIV/AIDS.

The compounds of Formula (I), or a pharmaceutically acceptable salt thereof, and further therapeutic agent(s) may be employed in combination by administration simultaneously in a unitary pharmaceutical composition including both agents. Alternatively, the combination may be administered separately in separate pharmaceutical compositions, each including one of the agents in a sequential manner wherein, for example, a compound of Formula (I) or a pharmaceutically acceptable salt thereof is administered first and the other agent second and vice versa. Such sequential administration may be close in time (e.g. simultaneously) or remote in time. For example, administration of the other agent several minutes to several dozen minutes after the administration of the first agent, and administration of the other agent several hours to several days after the administration of the first agent are within the scope of the invention, wherein the lapse of time is not limited. For example, one agent may be administered once a day, and the other agent may be administered 2 or 3 times a day, or one agent may be administered once a week, and the other agent may be administered once a day.

When administration is sequential, either the compound of the present invention or one or more (at least one) additional therapeutic agent may be administered first.

When administration is simultaneous, the combination may be administered either in the same or different pharmaceutical composition. When combined in the same formulation it will be appreciated that the compound and agents must be stable and compatible with each other and the other components of the formulation. When formulated separately they may be provided in any convenient formulation, conveniently in such manner as are known for such compounds in the art.

During a treatment regime, it will be appreciated that administration of each agent of the combination may be repeated one or more (at least one) times.

Furthermore, the agents may be administered in the same or different dosage forms, e.g. one agent may be administered topically and the other compound may be administered orally. Suitably, both agents are administered orally.

The combinations may be presented as a combination kit. By the term "combination kit" "or kit of parts" as used herein is meant the pharmaceutical composition or compositions that are used to administer the combination according to the invention. When the agents of the combination are administered simultaneously, the combination kit can contain the agents in a single pharmaceutical composition, such as a tablet, or in separate pharmaceutical compositions. When the agents are not administered simultaneously, the combination kit will contain each agent in separate pharmaceutical compositions either in a single package or in separate pharmaceutical compositions in separate packages. The combination kit can also be provided with instructions, such as dosage and administration instructions. Such dosage and administration instructions can be of the kind that are provided to a doctor, for example by a drug product label, or they can be of the kind that are provided by a doctor, such as instructions to a patient.

In one aspect, the one or more (at least one) additional therapeutic agents is a therapeutic vaccine. A compound of Formula (I), or a pharmaceutically acceptable salt thereof, may thus be administered in conjunction with vaccination against parasitic infection. Existing veterinary vaccines for leishmaniasis include CaniLeish and Leishmune.

A compound of Formula (I), or a pharmaceutically acceptable salt thereof, may be either i) administered to an individual who has previously been vaccinated against parasitic infection; ii) administered to an individual who is subsequently vaccinated against parasitic infection; or iii) may be co-administered with a vaccine against parasitic infection, either by administering the compound of the invention and the vaccine together in the same dosage form or co-administering the compound of the invention and the vaccine in separate dosage forms.

When a compound of Formula (I), or a pharmaceutically acceptable salt thereof is used in combination with one or more (at least one) additional therapeutic agents, the dose of the compound or agent may differ from that when the compound or agent is used alone. Appropriate doses will be readily appreciated by those skilled in the art. It will be appreciated that the amount of a compound of the invention and the one or more (at least one) additional therapeutic agents required for use in treatment will vary with the nature of the condition being treated and the age and the condition of the patient and will be ultimately at the discretion of the attendant physician or veterinarian.

ABBREVIATIONS

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:

AIDS Acquired Immune Deficiency Syndrome
approx. Approximately
$CDCl_3$ Deuterated chloroform
CLND ChemiLuminescent Nitrogen Detection
$CO_2$ Carbon dioxide
DAPI 4',6-Diamidino-2-phenylindole
DAST Diethylaminosulfur trifluoride
DCM Dichloromethane
DIPEA Diisopropylethylamine
DMAP 4-Dimethylaminopyridine
DMEM Dulbecco's Modified Eagle Medium
DMF N,N-Dimethylformamide
DMSO Dimethylsulfoxide
DMSO-$d_6$ Deuterated dimethylsulfoxide
$Et_2O$ Diethyl ether
EtOAc Ethyl acetate
EtOH Ethanol
FBS Fetal bovine serum
g grams
GFP Green Fluorescent Protein
h hours
$H_2O$ Water
HCl hydrochloric acid
HEPES 4-(2-hydroxyethyl)-1-piperazineethanesulfonic acid
HIV Human Immunodeficiency Virus
HPLC high performance liquid chromatography
Hz hertz
L liters
LCMS liquid chromatography/mass spectrometry
M Molar
MeCN acetonitrile
MeOH Methanol
min Minutes
mL Milliliter
mmol Millimole
nM Millimolar
µM Micromolar
MEM 2-methoxyethoxy methyl
MS Mass spectrum
N Normal concentration
NaOH Sodium hydroxide
NMR Nuclear Magnetic Resonance spectroscopy
PBS Phosphate buffered saline
PBS-A Bovine serum albumin
Pd(dppf)$Cl_2$.DCM [1,1T-Bis(diphenylphosphino)ferrocene]dichloropalladium(II), complex with dichloromethane
PMA Phorbol 12-myristate 13-acetate
RB Round-bottomed
RPMI Roswell Park Memorial Institute
RT/rt Room Temperature
THF Tetrahydrofuran
THP Tetrahydropyranyl
THP-1 human acute monocytic leukemia cell line
TLC Thin layer chromatography

EXAMPLES

The following Examples illustrate the invention, as guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance ($^1$H NMR) spectra were recorded, and chemical shifts are reported in parts per million (ppm) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Reactions involving metal hydrides (including sodium hydride) and organo-metallic reagents are carried out under argon or nitrogen unless otherwise specified.

In the following Intermediates and Examples, where the relative stereochemistry of the compound has been identified, this is indicated both in the name and structure of the compound.

In certain of the following Intermediates and Examples, starting materials are identified by reference to other Intermediate or Example numbers. This does not signify that the actual material (or "batch") obtained from any particular Intermediate or Example was necessarily used in a subsequent step exemplified herein, but is used as a short-hand means of denoting the relevant compound name.

The names of the intermediates and examples have been obtained using the compound naming program within "ChemBioDraw Ultra v12" or "ACD Name Pro 6.02".

Intermediate 2. N-(3-acetyl-4-fluorophenyl)pyrrolidine-1-carboxamide

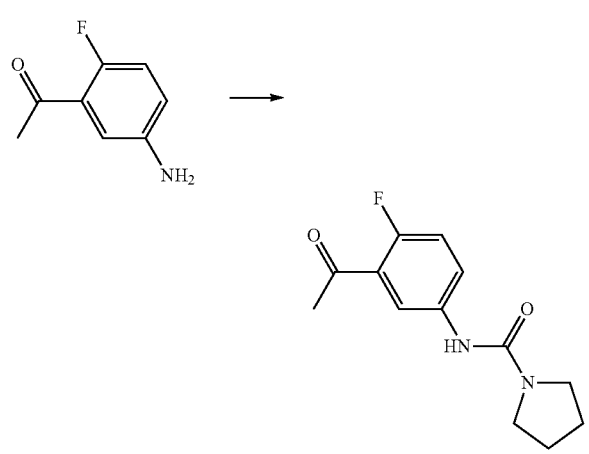

A stirred solution of 1-(5-amino-2-fluoro-phenyl)ethanone (Intermediate 1, purchased for example from APOLLO) (10.0 g, 65.3 mmol) and DMAP (400 mg, 3.3 mmol) in pyridine (100 mL) and DCM (400 mL) at rt was treated with pyrrolidine-1-carbonyl chloride (purchased from ALDRICH) (13.08 g, 97.9 mmol). The reaction was stirred at 50° C. for 16-72 hours until TLC (hexane/EtOAc 1:1) revealed reaction had gone to completion. The reaction was then concentrated in vacuo at 60° C., the residual dark syrup diluted with DCM (400 mL), washed with brine (200 mL) and the organic phase dried (MgSO$_4$), concentrated in vacuo to give a powder which was triturated with 1:1 EtOAc:Et$_2$O, stirred at rt for 12 h then collected by filtration and dried to give N-(3-acetyl-4-fluoro-phenyl)pyrrolidine-1-carboxamide (13.55 g, 53.6 mmol, 82% yield) as a faintly lilac powder.

$^1$H NMR (500 MHz, DMSO-d$_6$): δ 8.37 (1H, s), 7.94 (1H, dd, J=6.7 Hz, 2.8 Hz), 7.85-7.81 (1H, m), 7.23 (1H, dd, J=10.9 Hz, 9.0 Hz), 3.38-3.34 (4H, m), 2.56 (3H, d, J=4.6 Hz), 1.88-1.83 (4H, m).

Intermediate 3. N-(3-(2-bromoacetyl)-4-fluorophenyl)pyrrolidine-1-carboxamide

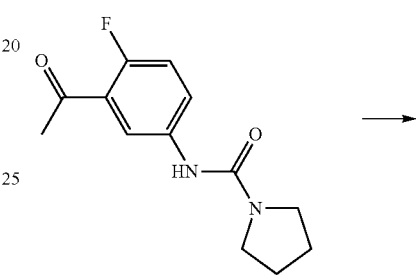

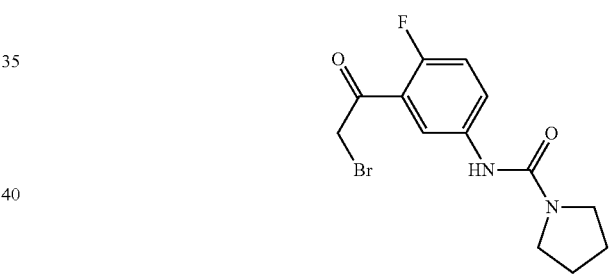

N-(3-acetyl-4-fluoro-phenyl)pyrrolidine-1-carboxamide (Intermediate 2) (11.7 g, 46.8 mmol) was dissolved in THF (400 mL), cooled at 0° C. and treated portion-wise with trimethyl(phenyl)ammonium tribromide (purchased from ALDRICH) (17.58 g, 46.8 mmol). The reaction was allowed to warm to rt then stirred overnight prior to concentration in vacuo. The residual solid was dissolved in DCM (500 mL), washed with water (2×200 mL), brine (200 mL) and saturated aqueous sodium hydrogencarbonate solution (200 mL), then dried (MgSO$_4$), filtered and concentrated. The residual solid was then triturated with EtOAc/Et$_2$O (1:1) first, then with EtOAc (200 mL), collected by filtration and dried under vacuum to give N-[3-(2-bromoacetyl)-4-fluoro-phenyl]pyrrolidine-1-carboxamide (12.47 g, 34.1 mmol, 73% yield) which contained approx. 5% N-(3-acetyl-4-fluoro-phenyl)pyrrolidine-1-carboxamide and 5% N-(3-(2,2-dibromoacetyl)-4-fluorophenyl)pyrrolidine-1-carboxamide.

$^1$H NMR (500 MHz, DMSO-d$_6$): δ 8.40 (1H, s), 8.02 (1H, dd, J=6.6 Hz, 2.9 Hz), 7.90-7.85 (1H, m), 7.27 (1H, dd, J=10.9 Hz, 9.0 Hz), 4.78 (2H, d, J=2.4 Hz), 3.39-3.33 (4H, m), 1.88-1.84 (4H, m).

Intermediate 5. 6-Bromo-1,2,4-triazin-3-amine

Intermediate 5 Method A (modified from U.S. Pat. Appl. Publ. 2011/0212967), 1 Sep. 2011)

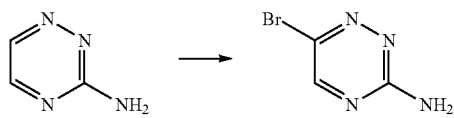

1,2,4-triazin-3-amine (Intermediate 4, purchased from ALDRICH) (22.47 g, 233.8 mmol) was dissolved in dioxane (400 mL) at rt then water added (400 mL) to give a solution which was cooled to 0° C. The reaction was then treated with 1-bromopyrrolidine-2,5-dione (N-bromosuccinimide) (42.45 g, 238.5 mmol), stirred at 0° C. for 10 min and then allowed to warm to RT and stirred for 4 h until TLC indicated complete consumption of starting material TLC (hexane/EtOAc 1:1). The reaction mixture was then cooled to 0° C., diluted with EtOAc (500 mL) and powdered $K_2CO_3$ (33 g) added. The resulting biphase was separated. The aqueous phase was set aside and the organic phase washed with brine (1×200 mL), dried ($MgSO_4$) and concentrated in vacuo. The resulting slurry was triturated in 250 mL of $Et_2O$ with overnight stirring, to give a free-flowing powder which was collected by filtration, washed with ice-cold $Et_2O$ and dried under vacuum to give 6-bromo-1,2,4-triazin-3-amine (13.9 g, 77.5 mmol, 33% yield) as a tan powder. Additional material was recovered from the first aqueous phase: To the initial dark coloured aqueous layer was added EtOAc (200 mL) resulting in an emulsion which was filtered through a course sinter and the resulting biphase separated. The aqueous phase was extracted with EtOAc exhaustively, all organic extracts combined, washed with brine, dried ($MgSO_4$) and concentrated to give a further 7.5 g of product (90% pure by LCMS).

$^1$H NMR (500 MHz, DMSO-$d_6$): δ 8.41 (1H, s), 7.50 (2H, br m).

Intermediate 5 Method B

A solution of 1,2,4-triazin-3-amine (Intermediate 4, purchased from ALDRICH) (3.0 g, 31.2 mmol) in water (200+100 mL) was cooled to 0-5° C. Bromine (4 mL, 78 mmol) was added drop-wise over 45 min, then the reaction mixture was stirred overnight at room temperature. When all starting material had been consumed according to TLC (50% EtAcO:EtOH (3:1)/cyclohexane), a saturated aqueous $Na_2SO_3$ solution (100 mL) was added to the reaction mixture and then the mixture was basified to pH 12 by addition of 2 N aqueous NaOH solution. The mixture was extracted with ethyl acetate (2×200 mL). The combined organic layers were dried over sodium sulfate, filtered and concentrated under reduced pressure to afford 6-bromo-1,2,4-triazin-3-amine (pale yellow solid, 2.51 g).

$^1$H NMR (400 MHz, DMSO-$d_6$): δ 8.40 (1H, s), 7.47 (2H, br m).

Intermediate 6. 6-Morpholino-1,2,4-triazin-3-amine

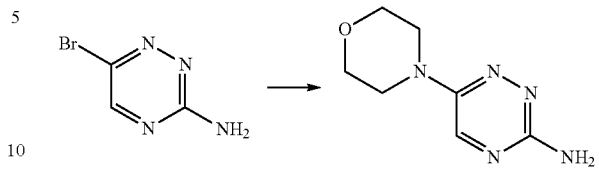

6-Bromo-1,2,4-triazin-3-amine (Intermediate 5) (4.5 g, 25.7 mmol) was loaded in equal portions into three 20 mL microwave vials fitted with stirrer bars, then morpholine (8.0 mL) added to each. The sealed vials were sonicated for 5 min at 60° C. to ensure a complete solution was obtained prior to heating to 120° C. for 1 h after which time TLC (100% EtOAc) indicated complete consumption of starting material. The reactions were combined, concentrated in vacuo to a brown gum which was azeotroped with EtOAc (20 mL×3), DCM (20 mL) then MeOH (20 mL) until a hard gum was obtained. This was then diluted with 10 mL of MeOH and the solution treated with 7N ammonia in MeOH (50 mL) stirred for 30 min and the solution concentrated in vacuo to give a thick gum. Purification by chromatography (100% EtOAc to 15% 7M methanolic ammonia in EtOAc) gave 6-morpholino-1,2,4-triazin-3-amine (1.75 g, 9.66 mmol, 38% yield) as an off-white powder.

$^1$H NMR (500 MHz, DMSO-$d_6$): δ 8.30 (1H, s), 6.39 (2H, br m), 3.72 (4H, m), 3.31 (4H, m).

Intermediate 7. 6-Phenyl-1,2,4-triazin-3-amine

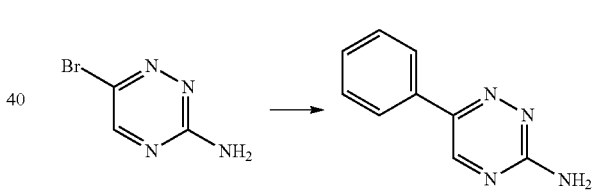

To a solution of 6-bromo-1,2,4-triazin-3-amine (Intermediate 5) (3.0 g, 17.1 mmol) and 4,4,5,5-tetramethyl-2-phenyl-1,3,2-dioxaborolane (purchased from MAYBRIDGE) (5.25 g, 25.7 mmol) in 1,4-Dioxane (100 mL) in a 250 mL RB flask was added a solution of potassium carbonate (7.1 g, 51.4 mmol) in water (20 mL). The resulting solution was deoxygenated by bubbling through a stream of nitrogen for 10 min prior to the addition of Pd(dppf)$Cl_2$.DCM (650 mg, 0.8 mmol). The reaction was then fitted with a reflux condenser under a nitrogen balloon and heated to 90° C. After 4 h TLC (1:1 EtOAc/Hexanes) indicated clean product formation with complete consumption of starting material. The reaction mixture was cooled, diluted with EtOAc (200 mL) and water (200 mL), interfacial precipitate removed by filtration through a sinter funnel and the biphase separated. The aqueous layer was extracted with EtOAc (3×50 mL) and the organics combined, washed with brine and dried with $MgSO_4$ and concentrated in vacuo. The resulting slurry was triturated with 5:1 $Et_2O$:EtOAc and collected by filtration, washed with ice-cold EtOAc and dried in vacuo. The filtrate was cooled to 0° C., triturated and a further batch of product isolated by filtration, which when combined with the initial batch gave 6-phenyl-1,2,4-triazin-3-amine as a tan free-flowing solid (2.06 g, 11.3 mmol, 66% yield).

$^1$H NMR (500 MHz, DMSO-d$_6$): δ 8.81 (1H, s), 8.01-7.98 (2H, m), 7.53-7.48 (2H, m), 7.44 (1H, m), 7.34 (2H, br s).

Intermediate 9.
2-Bromo-1-(2-fluoro-5-nitrophenyl)ethanone

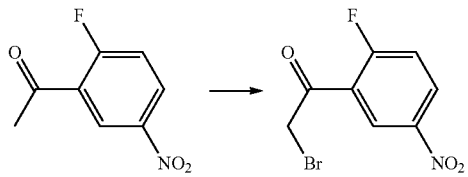

To 1-(2-fluoro-5-nitro-phenyl)ethanone (Intermediate 8, purchased from ENAMINE) (5.52 g, 30.1 mmol) in THF (100 ml) was added a solution of trimethyl(phenyl)ammonium tribromide (10.3 g, 27.4 mmol) in THF (50 ml) drop-wise, and stirred overnight at rt. The reaction mixture was filtered to remove solid, the solvent removed in vacuo and the crude material chromatographed (0-60% EtOAc/heptane). Fractions containing product were combined and solvent removed in vacuo to give 2-bromo-1-(2-fluoro-5-nitro-phenyl)ethanone (6.50 g, 22.3 mmol, 82% yield). Contained some impurities, relating to starting material/overbrominated material but was considered pure enough for use in subsequent steps $^1$H NMR (500 MHz, CDCl$_3$): δ 8.83 (1H, m), 8.48 (1H, m), 7.41 (1H, m), 4.52 (2H, d, J=4.8 Hz)

Intermediate 10. 4-(6-(2-Fluoro-5-nitrophenyl)imidazo[1,2-b][1,2,4]triazin-2-yl)morpholine

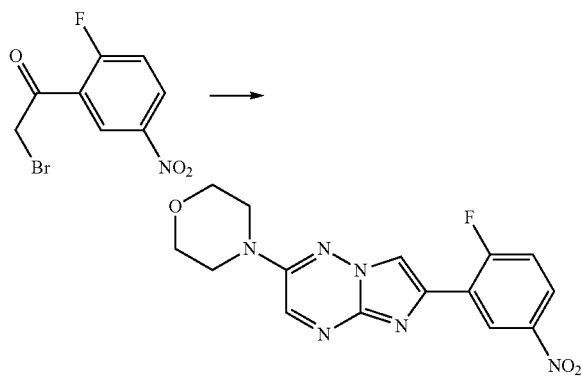

6-Morpholino-1,2,4-triazin-3-amine (Intermediate 9) (260 mg, 1.36 mmol) and 2-bromo-1-(2-fluoro-5-nitro-phenyl)ethanone (purchased from ENAMINE, 476 mg, 1.64 mmol) in MeCN (10 mL) were stirred at 60° C. overnight. The reaction mixture was cooled, partitioned between 2M NaOH/EtOAc, the organics separated, washed with water, brine, dried and the solvent removed in vacuo. Crude material was chromatographed (10-100% EtOAc/heptane) to yield 4-[6-(2-fluoro-5-nitro-phenyl)imidazo[1,2-b][1,2,4]triazin-2-yl]morpholine (140 mg, 0.36 mmol, 27% yield)

$^1$H NMR (500 MHz, DMSO-d$_6$): δ 8.99 (1H, m), 8.35 (1H, d, J=4.2 Hz), 8.27 (1H, m), 7.66 (1H, dd, J=9.1, 10.3 Hz), 3.78 (4H, m), 3.59 (4H, m).

Intermediate 11. 4-Fluoro-3-(2-morpholinoimidazo[1,2-b][1,2,4]triazin-6-yl)aniline

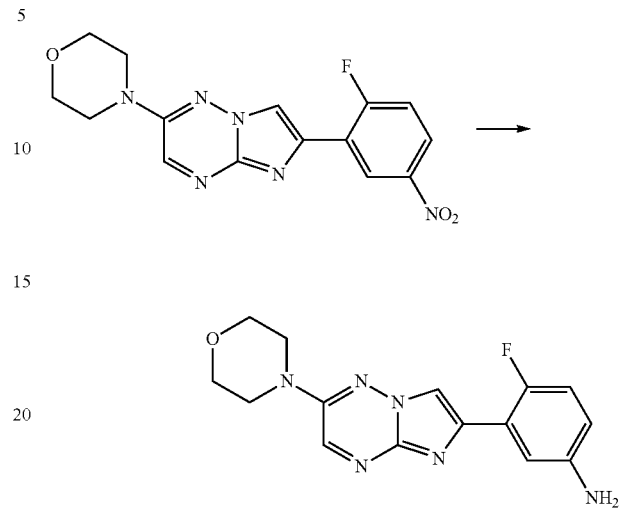

To 4-[6-(2-fluoro-5-nitro-phenyl)imidazo[1,2-b][1,2,4]triazin-2-yl]morpholine (Intermediate 10) (140 mg, 0.40 mmol) in ethanol (8 mL) was added iron (182 mg, 3.25 mmol) then ammonium chloride (87 mg, 1.63 mmol) n water (2 mL) and the mixture stirred at 80° C. for 3 hours. The reaction mixture was filtered hot through celite, washing through with hot MeOH. The solvent was removed in vacuo, and the crude material partitioned between water/EtOAc. The organics were separated, washed with brine, dried and solvent removed in vacuo. MeCN was added and the resulting solid collected, washed with MeCN and dried in vacuo to give 4-fluoro-3-(2-morpholinoimidazo[1,2-b][1,2,4]triazin-6-yl)aniline (120 mg, 0.36 mmol, 89% yield).

$^1$H NMR (500 MHz, DMSO-d$_6$): δ 8.68 (1H, s), 8.04 (1H, d, J=4.1 Hz), 7.43 (1H, m), 6.95 (1H, dd, J=8.7, 11.1 Hz), 6.53 (1H, m), 5.09 (2H, s), 3.77 (4H, m), 3.55 (4H, m).

Example 1. N-(4-fluoro-3-(2-morpholinoimidazo[1,2-b][1,2,4]triazin-6-yl)phenyl)pyrrolidine-1-carboxamide

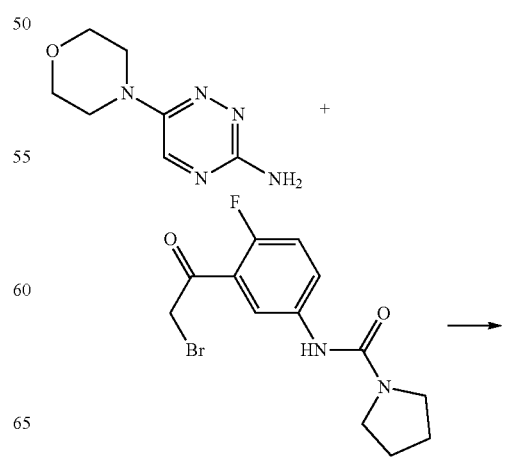

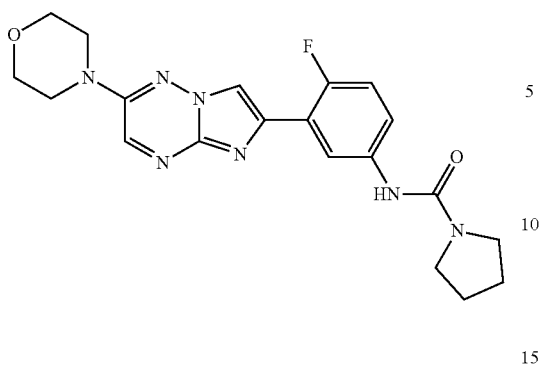

6-Morpholino-1,2,4-triazin-3-amine (Intermediate 6) (1.26 g, 6.9 mmol) in dry EtOH (80 mL) was warmed to 60° C. to give a solution, which was then treated portion-wise with stirring with N-[3-(2-bromoacetyl)-4-fluoro-phenyl]pyrrolidine-1-carboxamide (Intermediate 3) (90% purity containing non-brominated and dibrominated impurities, 2.30 g, 6.9 mmol) to give a solution. The reaction was stirred at 60° C. for 72 h by which time all bromoketone had been consumed. The reaction was allowed to cool to rt with stirring overnight resulting in formation of a precipitate, which was recovered by filtration onto a sintered funnel. The off-white solid was quickly washed with ice-cold EtOH and dried to give N-[4-fluoro-3-(2-morpholinoimidazo[1,2-b][1,2,4]triazin-6-yl)phenyl]pyrrolidine-1-carboxamide (1.28 g, 3.1 mmol, 44% yield) as a pale yellow crystalline solid.

The filtrate was concentrated in vacuo, then diluted with DCM (100 mL), washed with saturated aqueous sodium hydrogencarbonate (100 mL) and brine (100 mL), dried (MgSO$_4$) and concentrated. Chromatography (100% EtOAc moving to 10% 7M methanolic ammonia in EtOAc) and collection of clean fractions gave a solid which after trituration from ice cold EtOH and collection by filtration gave an additional 850 mg of product (approx. 90% purity). This material was recrystallised from hot EtOH and fine crystals isolated by filtration and shown to be >99% by high res LCMS.

Both crops were combined, redissolved in EtOH (100 mL) and concentrated slowly in vacuo. The precipitate was cooled with stirring and collected by filtration to give a total weight of 1.91 g (66% yield).

$^1$H NMR (500 MHz, DMSO-d$_6$): δ 8.70 (1H, s), 8.35-8.30 (2H, m), 8.12 (1H, d, J=4.1 Hz), 7.62 (1H, ddd, J=8.9 Hz, 4.5 Hz, 2.9 Hz), 7.18 (1H, dd, J=10.9 Hz, 8.9 Hz), 3.77 (4H, m), 3.56 (4H, m), 3.39 (4H, m), 1.87 (4H, m).

Example 2. N-(4-fluoro-3-(2-phenylimidazo[1,2-b][1,2,4]triazin-6-yl)phenyl)pyrrolidine-1-carboxamide

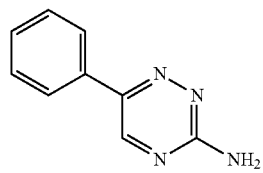

A slurry of 6-phenyl-1,2,4-triazin-3-amine (Intermediate 7) (777 mg, 4.47 mmol) in EtOH (50.0 mL) was heated to 50° C. to form a solution which was treated portion-wise with N-[3-(2-bromoacetyl)-4-fluoro-phenyl]pyrrolidine-1-carboxamide (Intermediate 3) (1.44 g, 4.38 mmol). After heating at 60° C. for 3 d a precipitate was formed. The cooled reaction was filtered through a sintered funnel, the residue washed with ice cold EtOH (10 mL) and dried under vacuum to give N-[4-fluoro-3-(2-phenylimidazo[1,2-b][1,2,4]triazin-6-yl)phenyl]pyrrolidine-1-carboxamide (1.09 g, 2.68 mmol, 60% yield) as a yellow powder.

$^1$H NMR (500 MHz, DMSO-d$_6$): δ 9.25 (1H, s), 8.60 (1H, d, J=4.0 Hz), 8.47 (1H, dd, J=6.8 Hz, 2.8 Hz), 8.40 (1H, s), 8.18-8.15 (2H, m), 7.71 (1H, ddd, J=8.9 Hz, 4.5 Hz, 2.8 Hz), 7.64-7.61 (3H, m), 7.26 (1H, dd, J=10.8 Hz, 9.0 Hz), 3.41 (4H, m), 1.88 (4H, m).

Example 3. N-(4-fluoro-3-(2-(pyrrolidin-1-yl)imidazo[1,2-b][1,2,4]triazin-6-yl)phenyl)pyrrolidine-1-carboxamide

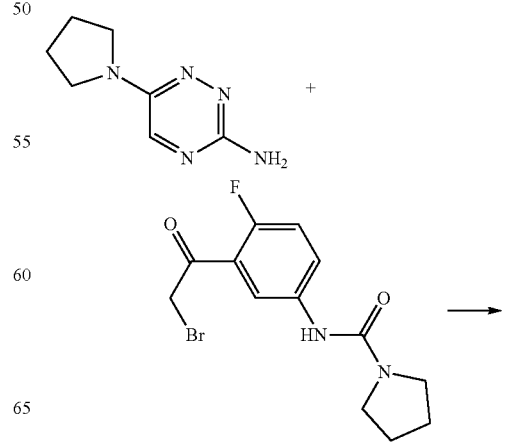

-continued

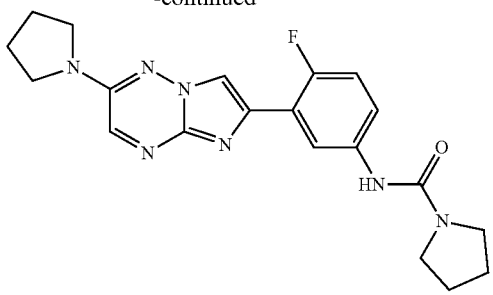

Example 3 was prepared according to a procedure similar to that of Example 1 from 6-pyrrolidin-1-yl-1,2,4-triazin-3-amine (in turn made according to a similar procedure to that of Intermediate 6) (250 mg, 1.52 mmol) and N-[3-(2-bromoacetyl)-4-fluoro-phenyl]pyrrolidine-1-carboxamide (Intermediate 3) (491 mg, 1.49 mmol) in EtOH (10 mL) to give N-[4-fluoro-3-(2-pyrrolidin-1-ylimidazo[1,2-b][1,2,4]triazin-6-yl)phenyl]pyrrolidine-1-carboxamide (234 mg, 0.57 mmol, 37% yield) as a yellow powder.

$^1$H NMR (500 MHz, DMSO-d$_6$): δ 8.38 (1H, s), 8.32 (1H, dd, J=6.9 Hz, 2.9 Hz), 8.30 (1H, s), 8.05 (1H, d, J=4.2 Hz), 7.62-7.57 (1H, m), 7.16 (1H, dd, J=11.0 Hz, 9.1 Hz), 3.55-3.49 (4H, m), 3.42-3.37 (4H, m), 2.01-1.96 (4H, m), 1.89-1.84 (4H, m).

Example 4. N-(4-fluoro-3-(2-(piperidin-1-yl)imidazo[1,2-b][1,2,4]triazin-6-yl)phenyl)pyrrolidine-1-carboxamide

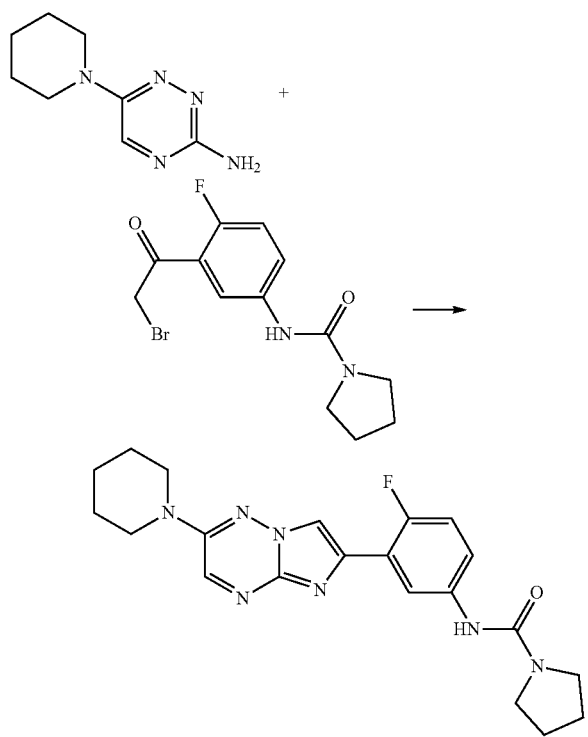

Example 4 was prepared according to a procedure similar to that of Example 1 from 6-piperidin-1-yl-1,2,4-triazin-3-amine (in turn made according to a similar procedure to that of Intermediate 6) (150 mg, 0.84 mmol) and N-[3-(2-bromoacetyl)-4-fluoro-phenyl]pyrrolidine-1-carboxamide (Intermediate 3) (270 mg, 0.82 mmol) in EtOH (10 mL) to give N-[4-fluoro-3-(2-pyrrolidin-1-ylimidazo[1,2-b][1,2,4]triazin-6-yl)phenyl]piperidine-1-carboxamide (56 mg, 0.12 mmol, 14% yield) as an off-white powder.

$^1$H NMR (500 MHz, DMSO-d$_6$): δ 8.71 (1H, s), 8.34-8.32 (2H, m), 8.08 (1H, d, J=4.1 Hz), 7.63-7.59 (1H, m), 7.20-7.15 (1H, m), 3.58 (4H, m), 3.39 (4H, m), 1.87 (4H, m), 1.64 (6H, m).

Example 5. (+,−)-N-(4-fluoro-3-(2-(2-methylmorpholino)imidazo[1,2-b][1,2,4]triazin-6-yl)phenyl)pyrrolidine-1-carboxamide. (+,−) denotes a racemate

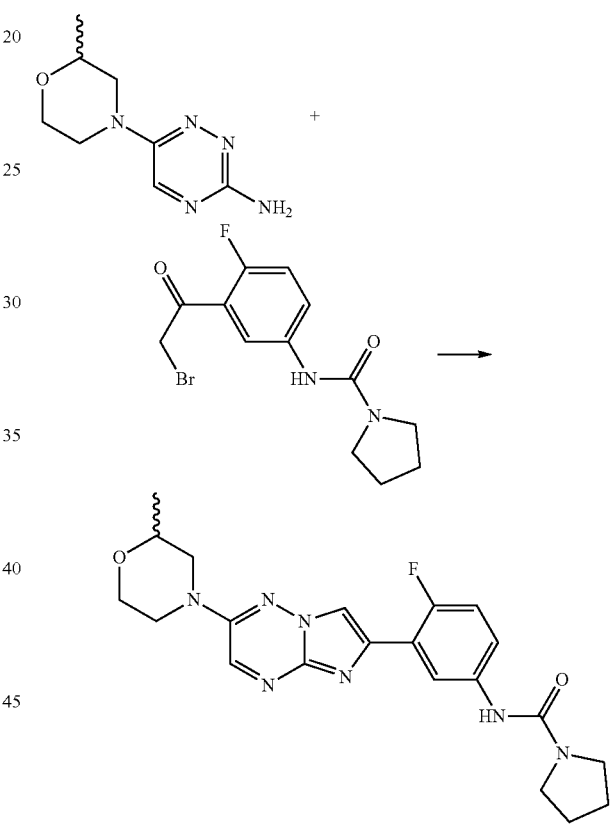

Example 5 was prepared according to a procedure similar to that of Example 1 from 6-(2-methylmorpholin-4-yl)-1,2,4-triazin-3-amine (in turn made according to a similar procedure to that of Intermediate 6) (240 mg, 1.23 mmol) and N-[3-(2-bromoacetyl)-4-fluoro-phenyl]pyrrolidine-1-carboxamide (Intermediate 3) (350 mg, 1.06 mmol) in EtOH (10 mL) to give N-(4-fluoro-3-(2-(2-methylmorpholino)imidazo[1,2-b][1,2,4]triazin-6-yl)phenyl)pyrrolidine-1-carboxamide (203 mg, 0.47 mmol, 38% yield) as a yellow powder.

$^1$H NMR (500 MHz, DMSO-d$_6$): δ 8.70 (1H, s), 8.34 (1H, dd, J=6.9 Hz, 2.7 Hz), 8.31 (1H, s), 8.11 (1H, d, J=4.1 Hz), 7.64-7.58 (1H, m), 7.17 (1H, dd, J=10.8 Hz, 9.2 Hz), 4.1 (1H, d, J=12.8 Hz), 4.03 (1H, d, J=13.1 Hz), 3.96 (1H, dd, J=3.5 Hz, 11.6 Hz), 3.71-3.60 (2H, m), 3.39 (4H, m), 3.02 (1H, td, J=12.7 Hz, 3.5 Hz), 2.70 (1H, dd, J=12.8 Hz, 10.6 Hz), 1.87 (4H, m), 1.18 (3H, d, J=6.2 Hz).

Example 6. N-(3-(2-((2S,6R)-2,6-dimethylmorpholino)imidazo[1,2-b][1,2,4]triazin-6-yl)-4-fluorophenyl)pyrrolidine-1-carboxamide (single enantiomer)

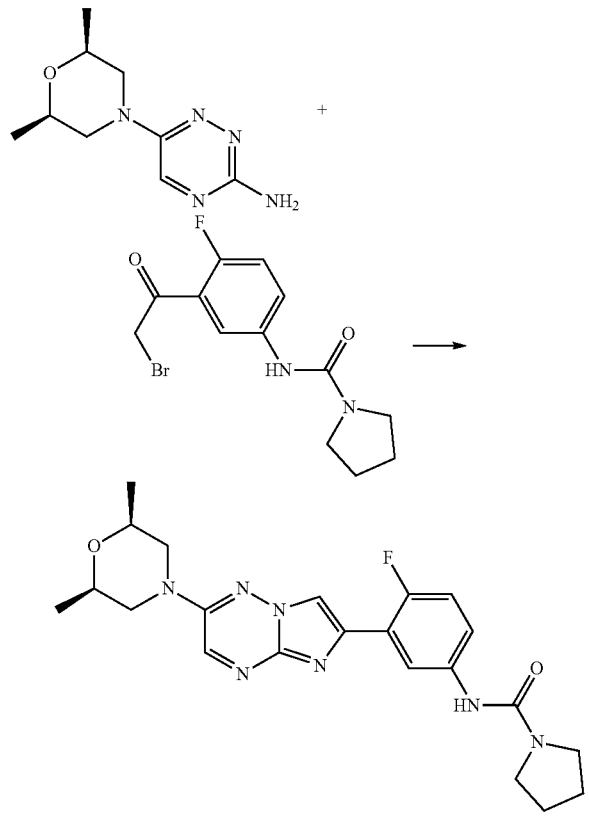

Example 6 was prepared according to a procedure similar to that of Example 1 from 6-[(2S,6R)-2,6-dimethylmorpholin-4-yl]-1,2,4-triazin-3-amine (in turn made according to a similar procedure to that of Intermediate 6) (128 mg, 0.61 mmol) and N-[3-(2-bromoacetyl)-4-fluoro-phenyl]pyrrolidine-1-carboxamide (Intermediate 3) (211 mg, 0.64 mmol) in EtOH (10 mL) to give N-[3-[2-[(2S,6R)-2,6-dimethyl-morpholin-4-yl]imidazo[1,2-b][1,2,4]triazin-6-yl]-4-fluoro-phenyl]pyrrolidine-1-carboxamide (130 mg, 0.29 mmol, 47% yield) as a yellow powder.

$^1$H NMR (500 MHz, DMSO-$d_6$): δ 8.71 (1H, s), 8.33 (1H, dd, J=6.9 Hz, 2.8 Hz), 8.31 (1H, s), 8.12 (1H, d, J=4.1 Hz), 7.63-7.58 (1H, m), 7.17 (1H, dd, J=11.0 Hz, 9.0 Hz), 4.14-4.09 (2H, m), 3.76-3.67 (2H, m), 3.40 (4H, m), 2.62 (2H, dd, J=13.0 Hz, 10.7 Hz), 1.87 (4H, m), 1.18 (6H, d, J=6.2 Hz).

Example 7. N-(4-fluoro-3-(2-(isopropylamino)imidazo[1,2-b][1,2,4]triazin-6-yl)phenyl)pyrrolidine-1-carboxamide

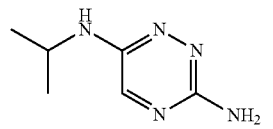

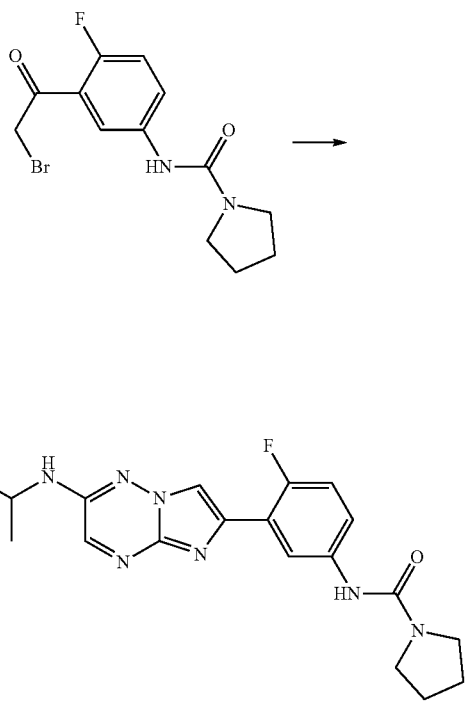

Example 7 was prepared according to a procedure similar to that of Example 1 from N$^6$-isopropyl-1,2,4-triazine-3,6-diamine (in turn made according to a similar procedure to that of Intermediate 6) (200 mg, 1.31 mmol) and N-[3-(2-bromoacetyl)-4-fluoro-phenyl]pyrrolidine-1-carboxamide (Intermediate 3) (408 mg, 1.24 mmol) in EtOH (10 mL) to give N-(4-fluoro-3-(2-(isopropylamino)imidazo[1,2-b][1,2,4]triazin-6-yl)phenyl)pyrrolidine-1-carboxamide (203 mg, 0.5 mmol, 38% yield) as a pink powder.

$^1$H NMR (500 MHz, DMSO-$d_6$): δ 8.31 (1H, s), 8.28 (1H, dd, J=6.8 Hz, 2.6 Hz), 8.08 (1H, s), 8.00 (1H, d, J=4.1 Hz), 7.61-7.57 (1H, m), 7.52 (1H, d, J=7.1 Hz), 7.18-7.12 (1H, m), 3.87 (1H, hp, J=6.7 Hz), 3.40-3.36 (4H, m), 1.89-1.84 (4H, m), 1.23 (6H, d, J=6.7 Hz).

Example 8. N-(4-fluoro-3-(imidazo[1,2-b][1,2,4]triazin-6-yl)phenyl)pyrrolidine-1-carboxamide

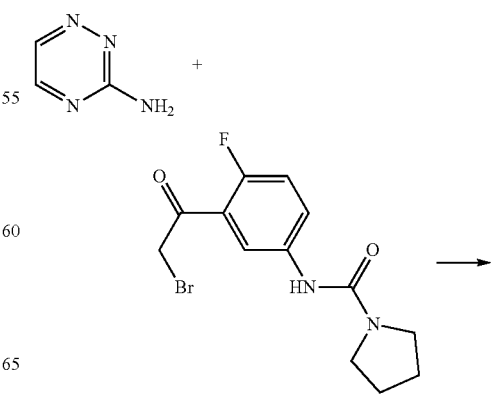

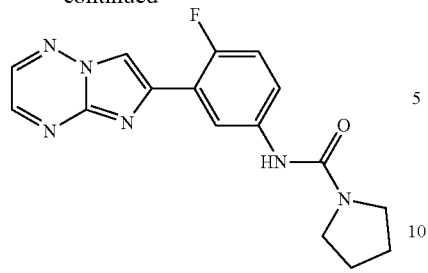

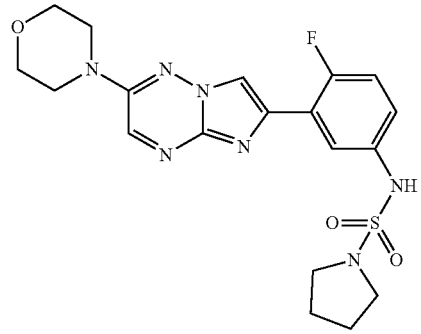

Example 8 was prepared according to a procedure similar to that of Example 1 from 1,2,4-triazine-3,6-diamine (in turn made according to a similar procedure to that of Intermediate 6) (58.3 mg, 0.61 mmol) and N-[3-(2-bromoacetyl)-4-fluoro-phenyl]pyrrolidine-1-carboxamide (200 mg, 0.61 mmol) in DMF (2.0 mL) to give N-(4-fluoro-3-(imidazo[1,2-b][1,2,4]triazin-6-yl)phenyl)pyrrolidine-1-carboxamide (20.0 mg, 0.06 mmol, 10% yield) as a white powder.

$^1$H NMR (500 MHz, DMSO-d$_6$): δ 8.70 (1H, d, J=2.0 Hz), 8.63 (1H, d, J=2.0 Hz), 8.57 (1H, d, J=4.0 Hz), 8.45 (1H, dd, J=6.8 Hz, 2.8 Hz), 8.37 (1H, s), 7.72-7.68 (1H, m), 7.24 (1H, dd, J=10.8 Hz, 9.0 Hz), 3.42-3.38 (4H, m), 1.89-1.86 (4H, m).

Example 10. N-(4-fluoro-3-(2-morpholinoimidazo[1,2-b][1,2,4]triazin-6-yl)phenyl)pyrrolidine-1-sulfonamide

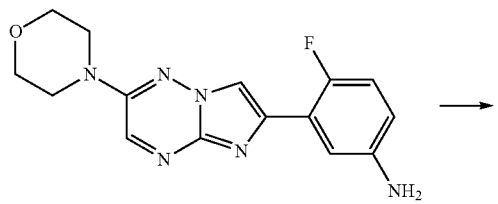

To 4-fluoro-3-(2-morpholinoimidazo[1,2-b][1,2,4]triazin-6-yl)aniline (Intermediate 11) (40 mg, 0.127 mmol) in DCM (1 mL)/pyridine (1.5 ml) was added DMAP (1.5 mg, 0.013 mmol), stirred for 5 minutes and pyrrolidine-1-sulfonyl chloride (26 mg, 0.153 mmol) in pyridine (0.5 ml) added. The reaction mixture was heated in a sealed tube at 50° C. for 4 hours. Further pyrrolidine-1-sulfonyl chloride (26 mg, 0.153 mmol) was added and stirring continued overnight. The reaction mixture was cooled, Further DCM (5 ml) added and washed with water, 1M HCl, and brine. The organic layer was collected via a phase separator and the solvent removed in vacuo. Crude material was purified by prep. LCMS (0-95% Acidic) to give N-[4-fluoro-3-(2-morpholinoimidazo[1,2-b][1,2,4]triazin-6-yl)phenyl]pyrrolidine-1-sulfonamide (10 mg, 0.021 mmol, 16% yield).

$^1$H NMR (500 MHz, DMSO-d$_6$): δ 9.91 (1H, s), 8.72 (1H, s), 8.14 (1H, d, J=4.2 Hz), 8.10 (1H, dd, J=2.8, 6.6 Hz), 7.30-7.19 (2H, m), 3.77 (4H, m), 3.57 (4H, m), 3.20 (4H, m), 1.74 (4H, m).

The following Examples were made according to analogous procedures to those described above.

| Example | Structure | Chemical name | Physical data ($^1$H NMR, MS) |
|---|---|---|---|
| Example 9 | 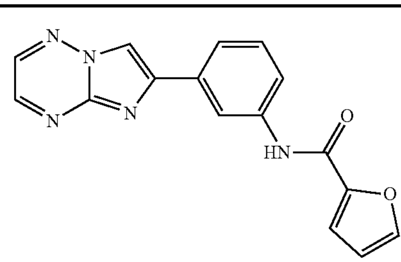 | N-(3-(imidazo[1,2-b][1,2,4]triazin-6-yl)phenyl)furan-2-carboxamide | $^1$H NMR (500 MHz, DMSO-d$_6$): δ 10.31 (1H, s), 8.90 (1H, s), 8.67 (1H, d, J = 2.0 Hz), 8.58 (1H, d, J = 2.0 Hz), 8.51 (1H, m), 7.97 (1H, m), 7.86-7.81 (2H, m), 7.47 (1H, t, J = 8.0 Hz), 7.41 (1H, d, J = 3.5 Hz), 6.73-6.71 (1H, m). MS: m/z: 306 [M + H] |

| Example | Structure | Chemical name | Physical data (¹H NMR, MS) |
|---|---|---|---|
| Example 11 | 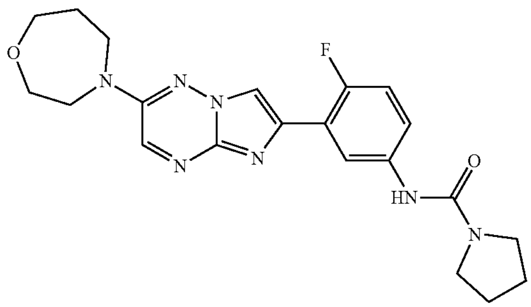 [SMILES: O=C(Nc1ccc(F)c(-c2cn3nc(N4CCCOCC4)cnc3n2)c1)N1CCCC1] | N-(3-(2-(1,4-oxazepan-4-yl)imidazo[1,2-b][1,2,4]triazin-6-yl)-4-fluorophenyl)pyrrolidine-1-carboxamide | ¹H NMR (500 MHz, DMSO-d₆): δ 8.62 (1H, s), 8.33 (1H, dd, J = 5.4 Hz), 8.30 (1H, s), 8.06 (1H, d, J = 3.4 Hz), 7.61 (1H, m), 7.14 (1H, t, J = 9.7 Hz), 3.85-3.76 (6H, m), 3.71-3.65 (2H, m), 3.42-3.35 (4H, m), 1.97-1.91 (2H, m), 1.89-1.83 (4H, m). MS: m/z: 426 [M + H] |
| Example 12 | 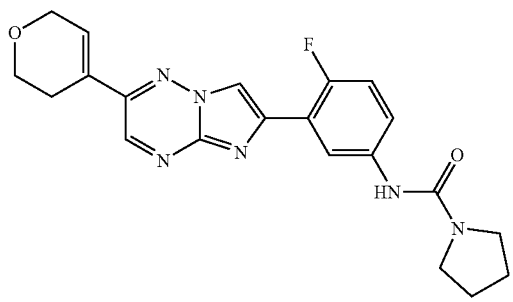 | N-(3-(2-(3,6-dihydro-2H-pyran-4-yl)imidazo[1,2-b][1,2,4]triazin-6-yl)-4-fluorophenyl)pyrrolidine-1-carboxamide | ¹H NMR (400 MHz, DMSO-d₆): δ 9.06 (1H, s), 8.45 (1H, d, J = 4), 8.42 (1H, dd, J = 6.8; 2.8), 8.35 (1H, s), 7.67 (1H, m), 7.22 (1H, dd, J = 10.9; 9.1), 7.12 (1H, m), 4.36 (2H, m), 3.87 (2H, t, J = 5.4), 3.39 (4H, m), 2.58 (2H, m), 1.86 (4H, m) MS: m/z: 409 [M + H] |
| Example 13 | 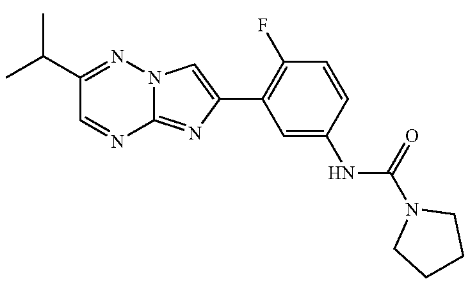 [SMILES: CC(C)c1cnc2nc(-c3cc(NC(=O)N4CCCC4)ccc3F)cn2n1] | N-(4-fluoro-3-(2-isopropylimidazo[1,2-b][1,2,4]triazin-6-yl)phenyl)pyrrolidine-1-carboxamide | ¹H NMR (400 MHz, CDCl₃): δ 8.39 (1H, s), 8.35 (1H, d, J = 4), 8.03 (1H, m), 7.98 (1H, d, J = 6.3), 7.13 (1H, dd, J = 10.9; 9.0), 6.33 (1H, br s), 3.48 (4H, m), 3.48 (1H, m), 2.00 (4H, m), 1.43 (6H, d, J = 6.8) MS: m/z: 369 [M + H] |
| Example 14 | 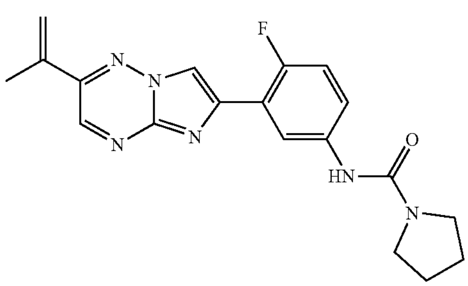 [SMILES: C=C(C)c1cnc2nc(-c3cc(NC(=O)N4CCCC4)ccc3F)cn2n1] | N-(4-fluoro-3-(2-(prop-1-en-2-yl)imidazo[1,2-b][1,2,4]triazin-6-yl)phenyl)pyrrolidine-1-carboxamide | ¹H NMR (400 MHz, CDCl₃): δ 9.12 (1H, s), 8.49 (1H, d, J = 4.0), 8.43 (1H, dd, J = 6.6, 2.9), 8.36 (1H, br s), 7.68 (1H, m), 7.23 (1H, dd, J = 10.8, 9.0), 6.25 (1H, s), 5.74 (1H, s), 3.40 (4H, m), 2.21 (3H, s), 1.87 (4H, m) MS: m/z: 367 [M + H] |
| Example 15 | 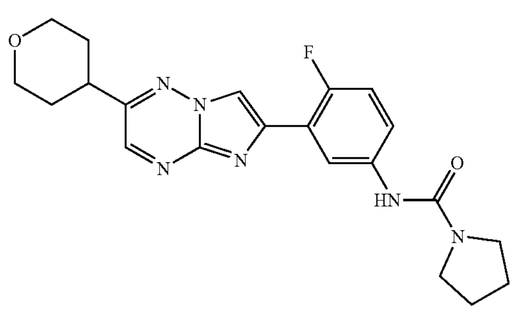 | N-(4-fluoro-3-(2-(tetrahydro-2H-pyran-4-yl)imidazo[1,2-b][1,2,4]triazin-6-yl)phenyl)pyrrolidine-1-carboxamide | ¹H NMR (400 MHz, CDCl₃): δ 8.39 (1H, s), 8.37 (1H, d, J = 4.0), 8.00 (2H, m), 7.14 (1H, dd, J = 10.9, 8.8), 6.33 (1H, s), 4.16 (2H, m), 3.61 (2H, dt, J = 11.4, 2.7), 3.48 (4H, m), 3.14 (1H, m), 2.09-1.91 (8H, m) MS: m/z: 411 [M + H] |

-continued

| Example | Structure | Chemical name | Physical data (¹H NMR, MS) |
|---|---|---|---|
| Example 16 | 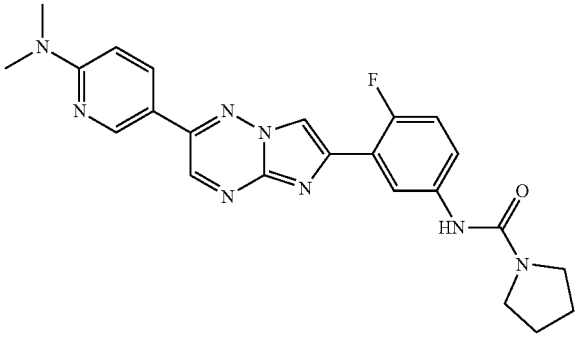 [SMILES: CN(C)c1ccc(-c2cnc3nc(-c4cc(NC(=O)N5CCCC5)ccc4F)cn3n2)cn1] | N-(3-(2-(6-(dimethyl-amino)pyridin-3-yl)imidazo[1,2-b][1,2,4]triazin-6-yl)-4-fluorophenyl)pyrrolidine-1-carboxamide | ¹H NMR (400 MHz, CDCl₃): δ 8.86 (1H, s), 8.83 (1H, d), 8.40 (1H, d), 8.14 (1H, dd), 8.02 (2H, m), 7.16 (1H, t), 6.68 (1H, d), 6.37 (1H, s), 3.51 (4H, m), 3.24 (6H, s), 2.03 (4H, m). MS: m/z: 447 [M + H] |
| Example 17 | 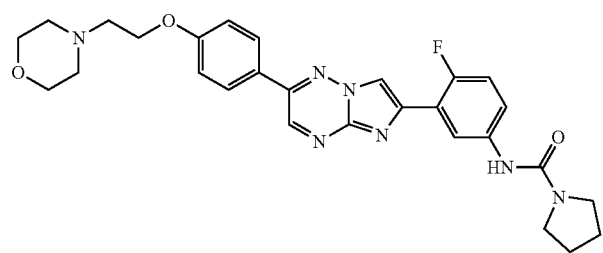 [SMILES: O=C(Nc1ccc(F)c(-c2cn3nc(-c4ccc(OCCN5CCOCC5)cc4)cnc3n2)c1)N1CCCC1] | N-(4-fluoro-3-(2-(4-(2-morpholinoethoxy)phenyl)imidazo[1,2-b][1,2,4]triazin-6-yl)phenyl)pyrrolidine-1-carboxamide | ¹H NMR (400 MHz, CDCl₃): δ 8.88 (1H, s), 8.44 (1H, s), 8.03 (2H, m), 8.0 (2H, d), 7.16 (1H, t), 7.11 (2H, d), 6.38 (1H, s, b), 4.24 (2H, m), 3.78 (4H, m), 3.51 (4H, m), 2.88 (2H, m), 2.64 (4H, m), 2.03 (4H, m). MS: m/z: 532 [M + H] |
| Example 18 | 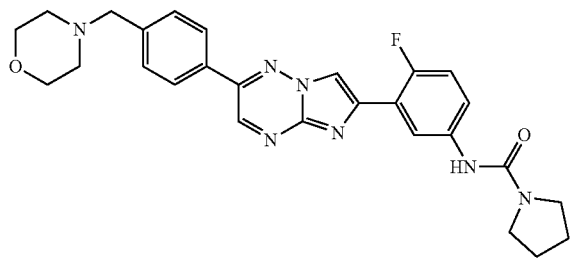 [SMILES: O=C(Nc1ccc(F)c(-c2cn3nc(-c4ccc(CN5CCOCC5)cc4)cnc3n2)c1)N1CCCC1] | N-(4-fluoro-3-(2-(4-(morpholinomethyl)phenyl)imidazo[1,2-b][1,2,4]triazin-6-yl)phenyl)pyrrolidine-1-carboxamide | ¹H NMR (400 MHz, CDCl₃): δ 8.92 (1H, s), 8.48 (1H, d), 8.05 (2H, m), 8.0 (2H, d), 7.59 (2H, d), 7.17 (1H, t), 6.37 (1H, br s), 3.77 (4H, m), 3.63 (2H, s), 3.51 (4H, m), 2.52 (4H, m), 2.03 (4H, m). MS: m/z: 502 [M + H] |
| Example 19 | 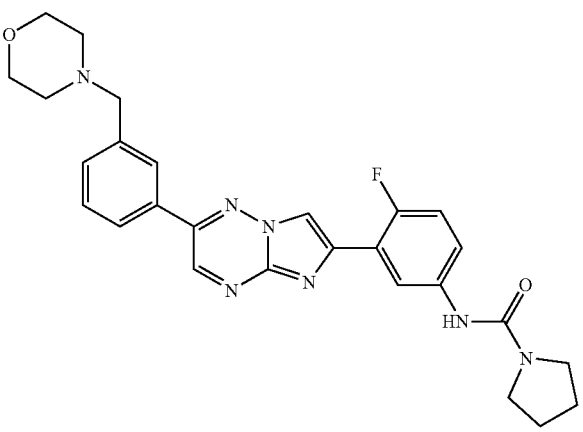 [SMILES: O=C(Nc1ccc(F)c(-c2cn3nc(-c4cccc(CN5CCOCC5)c4)cnc3n2)c1)N1CCCC1] | N-(4-fluoro-3-(2-(3-(morpholinomethyl)phenyl)imidazo[1,2-b][1,2,4]triazin-6-yl)phenyl)pyrrolidine-1-carboxamide | ¹H NMR (400 MHz, CDCl₃): δ 8.94 (1H, s), 8.49 (1H, d), 8.04 (3H, m), 7.92 (1H, m), 7.56 (2H, dd), 7.17 (1H, m), 6.37 (1H, br s), 3.77 (4H, m), 3.64 (2H, s, b), 3.50 (4H, m), 2.52 (4H, m), 2.02 (4H, m). MS: m/z: 502 [M + H] |

-continued

| Example | Structure | Chemical name | Physical data (¹H NMR, MS) |
|---|---|---|---|
| Example 20 | 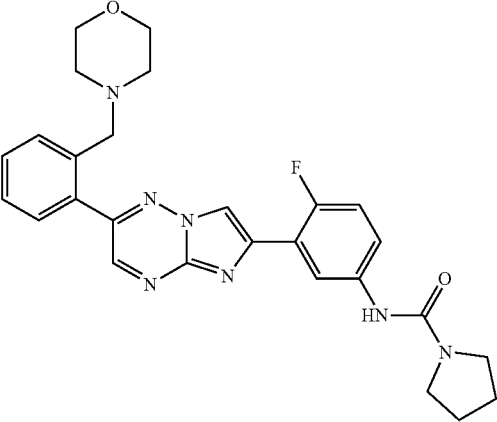 [SMILES: O=C(Nc1ccc(F)c(-c2cn3nc(-c4ccccc4CN4CCOCC4)cnc3n2)c1)N1CCCC1] | N-(4-fluoro-3-(2-(2-(morpholinomethyl)phenyl)imidazo[1,2-b][1,2,4]triazin-6-yl)phenyl)pyrrolidine-1-carboxamide | ¹H NMR (400 MHz, CDCl₃): δ 8.65 (1H, s), 8.40 (1H, d), 8.03 (2H, m), 7.50 (4H, m), 7.15 (1H, m), 6.37 (1H, br s), 3.67 (2H, s, b) 3.50 (4H, m), 3.33 (4H, m), 2.28 (4H, m), 2.02 (4H, m). MS: m/z: 502 [M + H] |
| Example 21 | 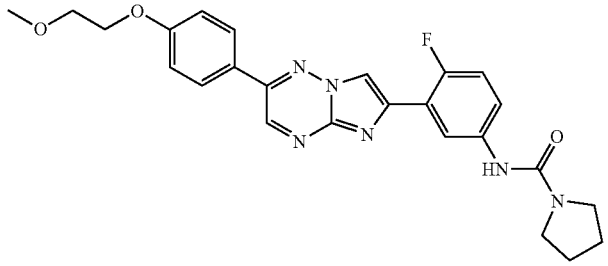 [SMILES: COCCOc1ccc(-c2cnc3nc(-c4cc(NC(=O)N5CCCC5)ccc4F)cn3n2)cc1] | N-(4-fluoro-3-(2-(4-(2-methoxyethoxy)phenyl)imidazo[1,2-b][1,2,4]triazin-6-yl)phenyl)pyrrolidine-1-carboxamide | ¹H NMR (400 MHz, CDCl₃): δ 8.89 (1H, s), 8.44 (1H, s), 8.03 (2H, m), 8.0 (2H, d), 7.15 (3H, m), 6.38 (1H, s, b), 4.26 (2H, m), 3.83 (2H, m), 3.51 (7H, m), 2.03 (4H, m). MS: m/z: 477 [M + H] |
| Example 22 | 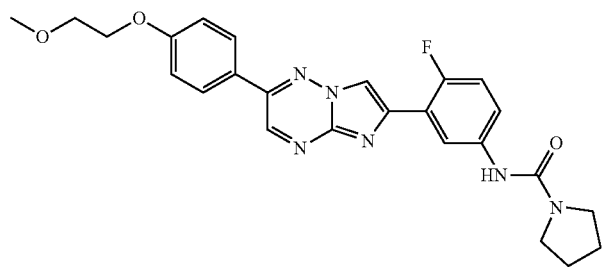 [SMILES: COCCOc1ccc(-c2cnc3nc(-c4cc(NC(=O)N5CCCC5)ccc4F)cn3n2)cc1] | N-(4-fluoro-3-(2-(4-(2-methoxyethoxy)phenyl)imidazo[1,2-b][1,2,4]triazin-6-yl)phenyl)pyrrolidine-1-carboxamide | ¹H NMR (400 MHz, CDCl₃): δ 8.89 (1H, s), 8.44 (1H, s), 8.03 (2H, m), 8.0 (2H, d), 7.15 (3H, m), 6.38 (1H, br s), 4.26 (2H, m), 3.83 (2H, m), 3.51 (7H, m), 2.03 (4H, m). MS: m/z: 477 [M + H] |
| Example 24 | 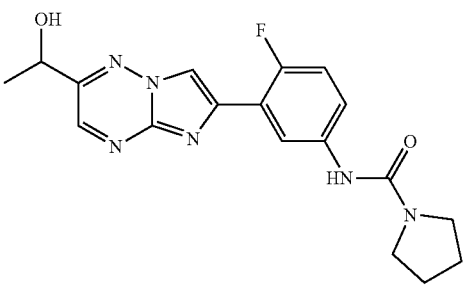 [SMILES: CC(O)c1cnc2nc(-c3cc(NC(=O)N4CCCC4)ccc3F)cn2n1] | (+,−)-N-(4-fluoro-3-(2-(1-hydroxyethyl)imidazo[1,2-b][1,2,4]triazin-6-yl)phenyl)pyrrolidine-1-carboxamide | ¹H NMR (400 MHz, DMSO-d₆) 8.75 (1H, s), 8.49 (1H, d, J = 4.0), 8.41 (1H, dd, J = 6.8, 2.8), 8.36 (1H, s), 7.70-7.66 (1H, m), 7.25-7.20 (1H, m), 5.9 (1H, d, J = 4.8), 4.95-4.89 (1H, m), 3.42-3.36 (4H, m), 1.88-1.85 (4H, m), 1.51 (3H, d, J = 6.6) MS: m/z: 371 [M + H] |
| Example 25 | 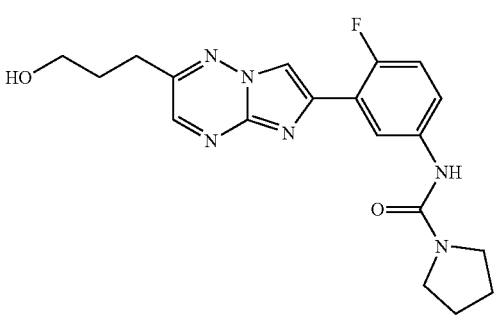 [SMILES: O=C(Nc1ccc(F)c(-c2cn3nc(CCCO)cnc3n2)c1)N1CCCC1] | N-(4-fluoro-3-(2-(3-hydroxypropyl)imidazo[1,2-b][1,2,4]triazin-6-yl)phenyl)pyrrolidine-1-carboxamide | ¹H NMR (400 MHz, DMSO-d₆): δ 8.59 (1H, s), 8.44 (1H, d, J = 3.8), 8.41-8.39 (1H, m), 8.35 (1H, s), 7.69-7.65 (1H, m), 7.24-7.19 (1H, m), 4.59 (1H, br m), 3.53-3.50 (2H, br m), 3.41-3.38 (4H, br m), 2.96-2.92 (2H, m), 1.93-1.86 (6H, m) MS: m/z: 385 [M + H] |

-continued

| Example | Structure | Chemical name | Physical data (¹H NMR, MS) |
|---|---|---|---|
| Example 26 | 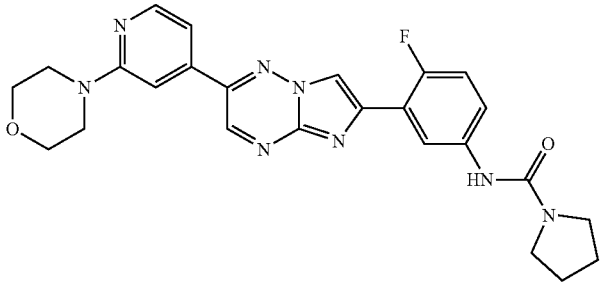 [SMILES: O=C(Nc1ccc(F)c(-c2cn3nc(-c4ccnc(N5CCOCC5)c4)cnc3n2)c1)N1CCCC1] | N-(4-fluoro-3-(2-(2-morpholinopyridin-4-yl)imidazo[1,2-b][1,2,4]triazin-6-yl)phenyl)pyrrolidine-1-carboxamide | ¹H NMR (400 MHz, CDCl$_3$): δ 8.87 (1H, s), 8.50 (1H, d, J = 3.5), 8.40 (1H, d, J = 5.3), 8.05-8.02 (2H, m), 7.25 (1H, s), 7.20-7.13 (2H, m), 6.36 (1H, s), 3.90-3.88 (4H, m), 3.67-3.65 (4H, m), 3.51-3.48 (4H, m), 2.03-2.00 (4H, m) MS: m/z: 489 [M + H] |
| Example 27 | 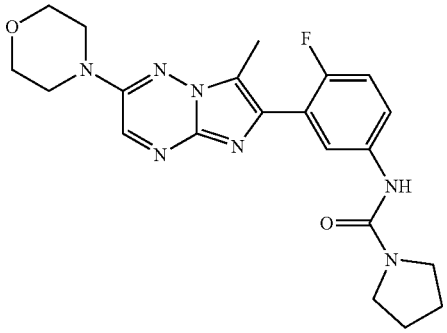 [SMILES: Cc1c(-c2cc(NC(=O)N3CCCC3)ccc2F)nc2ncc(N3CCOCC3)nn12] | N-(4-fluoro-3-(7-methyl-2-morpholinoimidazo[1,2-b][1,2,4]triazin-6-yl)phenyl)pyrrolidine-1-carboxamide | ¹H NMR (400 MHz, DMSO-d$_6$): δ 8.63 (1H, s), 8.26 (1H, s), 7.83 (1H, dd, J = 6.8, 2.8), 7.63-7.59 (1H, m), 7.18 (1H, dd, J = 10.1, 9.1), 3.79-3.76 (4H, m), 3.60-3.57 (4H, m), 3.39-3.35 (4H, m), 2.42 (3H, d, J = 3.0), 1.87-1.84 (4H, m) MS: m/z: 426 [M + H] |
| Example 28 | 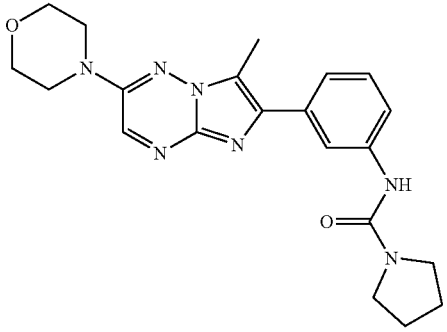 [SMILES: Cc1c(-c2cccc(NC(=O)N3CCCC3)c2)nc2ncc(N3CCOCC3)nn12] | N-(3-(7-methyl-2-morpholinoimidazo[1,2-b][1,2,4]triazin-6-yl)phenyl)pyrrolidine-1-carboxamide | ¹H NMR (400 MHz, DMSO-d$_6$): δ 8.58 (1H, s), 8.23 (1H, s), 8.07 (1H, t, J = 1.8), 7.55-7.53 (1H, m), 7.44-7.42 (1H, m), 7.31 (1H, t, J = 7.8), 3.79-3.77 (4H, m), 3.59-3.57 (4H, m), 3.41-3.36 (4H, s), 2.65 (3H, s), 1.88-1.85 (4H, m) MS: m/z: 408 [M + H] |
| Example 29 | 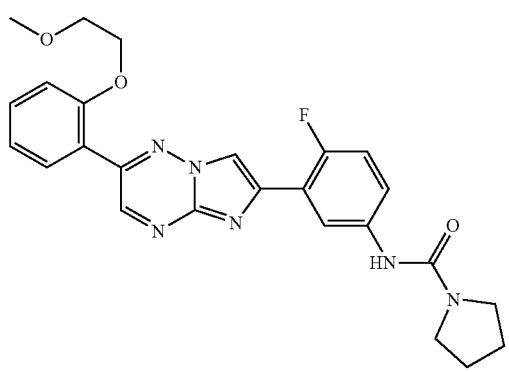 [SMILES: COCCOc1ccccc1-c1cnc2nc(-c3cc(NC(=O)N4CCCC4)ccc3F)cn2n1] | N-(4-fluoro-3-(2-(2-(2-methoxyethoxy)phenyl)imidazo[1,2-b][1,2,4]triazin-6-yl)phenyl)pyrrolidine-1-carboxamide | ¹H NMR (400 MHz, CDCl$_3$): δ 9.04 (1H, s), 8.41 (1H, d, J = 3.8), 8.03-7.99 (2H, m), 7.77-7.74 (1H, m), 7.53-7.49 (1H, m), 7.18-7.07 (3H, m), 6.38 (1H, s), 4.26 (2H, t, J = 4.5), 3.75 (2H, t, J = 4.5), 3.51-3.47 (4H, m), 3.43 (3H, s), 2.02-1.99 (4H, m) MS: m/z: 477 [M + H] |

-continued

| Example | Structure | Chemical name | Physical data ($^1$H NMR, MS) |
|---|---|---|---|
| Example 30 | 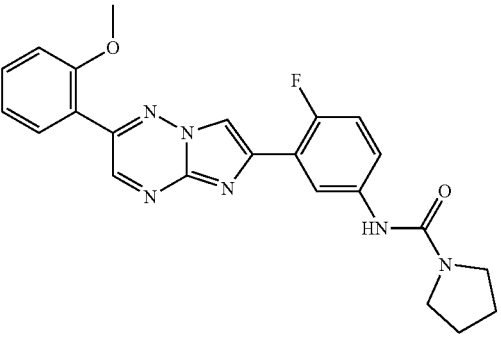 [SMILES: COc1ccccc1-c1cnc2nc(-c3cc(NC(=O)N4CCCC4)ccc3F)cn2n1] | N-(4-fluoro-3-(2-(2-methoxyphenyl)imidazo[1,2-b][1,2,4]triazin-6-yl)phenyl)pyrrolidine-1-carboxamide | $^1$H NMR (400 MHz, CDCl$_3$): δ 9.92 (1H, s), 8.42 (1H, d, J = 4.0), 8.04-8.00 (2H, m), 7.75-7.72 (1H, m), 7.55-7.51 (1H, m), 7.18-7.08 (3H, m), 6.38 (1H, s), 3.94 (3H, s), 3.49 (4H, t, J = 6.5), 2.01 (4H, t, J = 6.5) MS: m/z: 433 [M + H] |
| Example 32 | 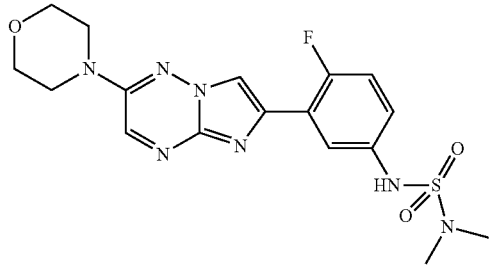 [SMILES: CN(C)S(=O)(=O)Nc1ccc(F)c(-c2cn3nc(N4CCOCC4)cnc3n2)c1] | N-(4-fluoro-3-(2-morpholinoimidazo[1,2-b][1,2,4]triazin-6-yl)phenyl)-N',N'-dimethylsulfamide | $^1$H NMR (400 MHz, DMSO-d$_6$): δ 9.99 (1H, s), 8.71 (1H, s), 8.15 (1H, d, J = 4.2 Hz), 8.09 (1H, dd, J = 3, 6.4 Hz), 7.31-7.19 (2H, m), 3.77 (4H, m), 3.58 (4H, m), 2.73 (6H, s) MS: m/z: 422 [M + H] |
| Example 33 | 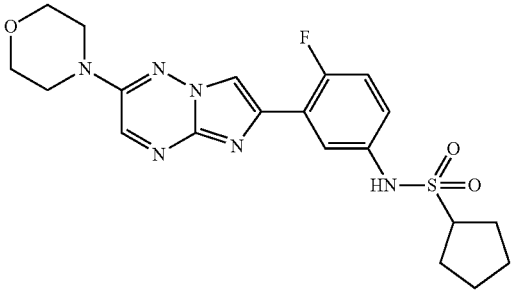 [SMILES: O=S(=O)(Nc1ccc(F)c(-c2cn3nc(N4CCOCC4)cnc3n2)c1)C1CCCC1] | N-(4-fluoro-3-(2-morpholinoimidazo[1,2-b][1,2,4]triazin-6-yl)phenyl)cyclopentanesulfonamide | $^1$H NMR (400 MHz, CD3OD): δ 8.59 (1H, s), 8.12 (1H, d, J = 4.2 Hz), 7.93 (1H, m), 7.34 (1H, m), 7.20 (1H, m), 3.87 (4H, m), 3.63 (4H, m), 2.05 (5H, m), 1.80 (2H, m), 1.64 (2H, m)) MS: m/z: 447 [M + H] |
| Example 34 | 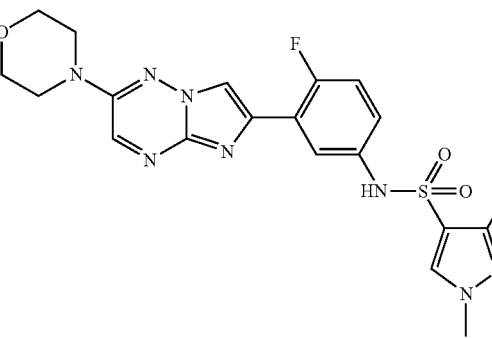 | N-(4-fluoro-3-(2-morpholinoimidazo[1,2-b][1,2,4]triazin-6-yl)phenyl)-1,3-dimethyl-1H-pyrazole-4-sulfonamide | $^1$H NMR (400 MHz, DMSO-d$_6$): δ 10.17 (1H, s), 8.73 (1H, s), 8.13 (2H, m), 7.99 (1H, m), 7.25 (1H, m), 7.13 (1H, m), 3.77 (4H, m), 3.73 (3H, m), 3.57 (4H, m), 2.19 (3H, s) MS: m/z: 473 [M + H] |

| Example | Structure | Chemical name | Physical data (¹H NMR, MS) |
|---|---|---|---|
| Example 35 | 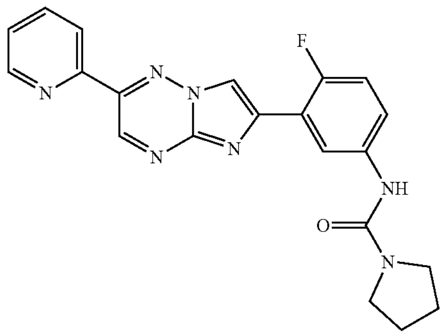 [SMILES: O=C(Nc1ccc(F)c(-c2cn3nc(-c4ccccn4)cnc3n2)c1)N1CCCC1] | N-(4-fluoro-3-(2-(pyridin-2-yl)imidazo[1,2-b][1,2,4]triazin-6-yl)phenyl)pyrrolidine-1-carboxamide | ¹H NMR (400 MHz, DMSO-d$_6$): δ 9.44 (1H, s), 8.82-8.81 (1H, m), 8.61 (1H, d, J = 3.8), 8.44 (1H, dd, J = 6.8, 2.8), 8.40 (1H, s), 8.32-8.30 (1H, m), 8.11-8.06 (1H, m), 7.74-7.70 (1H, m), 7.64-7.61 (1H, m), 7.28-7.23 (1H, m), 3.42-3.38 (4H, m), 1.89-1.85 (4H, m)<br>MS: m/z: 404 [M + H] |
| Example 36 | 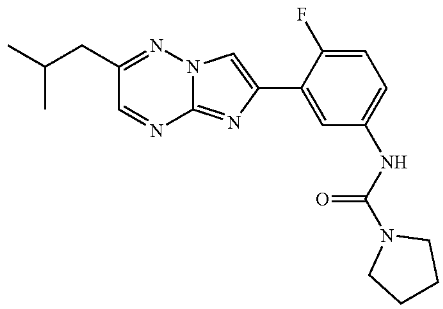 [SMILES: CC(C)Cc1cnc2nc(-c3cc(NC(=O)N4CCCC4)ccc3F)cn2n1] | N-(4-fluoro-3-(2-isobutyl-imidazo[1,2-b][1,2,4]triazin-6-yl)phenyl)pyrrolidine-1-carboxamide | ¹H NMR (400 MHz, DMSO-d$_6$): δ 8.59 (1H, s), 8.46 (1H, d, J = 4.0), 8.40 (1H, dd, J = 6.8, 2.8), 8.35 (1H, s), 7.69-7.65 (1H, m), 7.24-7.19 (1H, m), 3.41-3.36 (4H, m), 2.76 (2H, d, J = 7.1), 2.20-2.09 (1H, m), 1.88-1.85 (4H, m), 0.97 (6H, d, J = 6.6)<br>MS: m/z: 383 [M + H] |
| Example 37 | 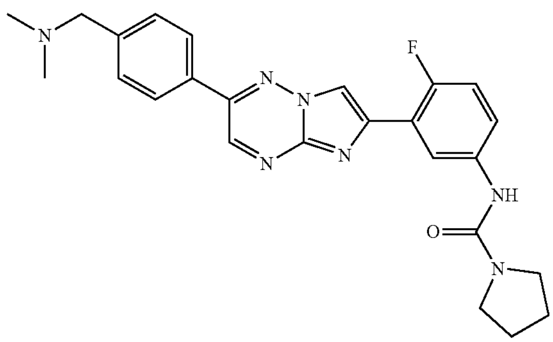 [SMILES: CN(C)Cc1ccc(-c2cnc3nc(-c4cc(NC(=O)N5CCCC5)ccc4F)cn3n2)cc1] | N-(3-(2-(4-((dimethyl-amino)methyl)phenyl)imidazo[1,2-b][1,2,4]triazin-6-yl)-4-fluoro-phenyl)pyrrolidine-1-carboxamide | ¹H NMR (400 MHz, DMSO-d$_6$): δ 9.22 (1H, s), 8.56 (1H, d, J = 4.0), 8.44 (1H, dd, J = 6.8, 2.8), 8.37 (1H, s), 8.12-8.10 (2H, m), 7.72-7.68 (1H, m), 7.53 (2H, d, J = 8.3), 7.27-7.22 (1H, m), 3.49 (2H, s), 3.42-3.38 (4H, m), 2.19 (6H, s), 1.89-1.85 (4H, m)<br>MS: m/z: 460 [M + H] |
| Example 38 | 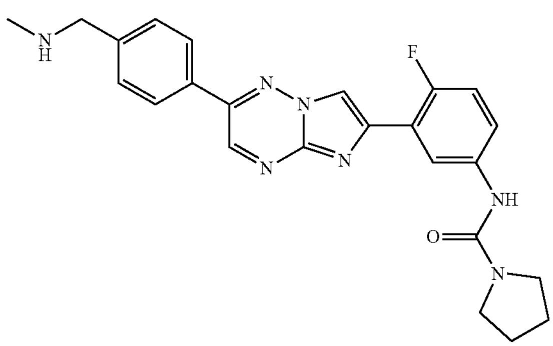 [SMILES: CNCc1ccc(-c2cnc3nc(-c4cc(NC(=O)N5CCCC5)ccc4F)cn3n2)cc1] | N-(4-fluoro-3-(2-(4-((methylamino)methyl)phenyl)imidazo[1,2-b][1,2,4]triazin-6-yl)phenyl)pyrrolidine-1-carboxamide | ¹H NMR (400 MHz, DMSO-d$_6$): δ 9.24 (1H, s), 8.57 (1H, d, J = 4.0), 8.46 (1H, dd, J = 6.8, 2.8), 8.37 (1H, s), 8.20 (1H, br s), 8.15-8.13 (2H, m), 7.17-7.67 (1H, m), 7.59 (2H, d, J = 8.3), 7.24 (1H, dd, J = 10.9, 9.1), 3.88 (2H, s), 3.42-3.39 (4H, m), 2.38 (3H, s), 1.89-1.85 (4H, m)<br>MS: m/z: 446 [M + H] |

-continued

| Example | Structure | Chemical name | Physical data (¹H NMR, MS) |
|---|---|---|---|
| Example 39 | 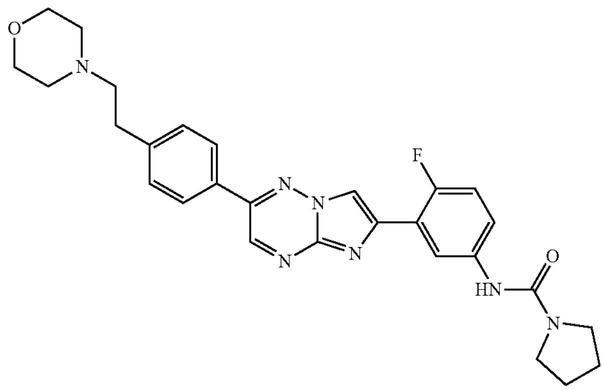 [SMILES: O=C(Nc1ccc(F)c(-c2cn3nc(-c4ccc(CCN5CCOCC5)cc4)cnc3n2)c1)N1CCCC1] | N-(4-fluoro-3-(2-(4-(2-morpholinoethyl)phenyl)imidazo[1,2-b][1,2,4]triazin-6-yl)phenyl)pyrrolidine-1-carboxamide | ¹H NMR (400 MHz, CDCl$_3$): δ 8.89 (1H, s), 8.44 (1H, d, J = 3.8), 8.05-8.01 (2H, m), 7.94 (2H, d, J = 8.3), 7.43 (2H, d, J = 8.3), 7.17-7.12 (1H, m), 6.36 (1H, s), 3.78-3.75 (4H, m), 3.49 (4H, t, J = 6.5), 2.93-2.90 (2H, m), 2.69-2.65 (2H, m), 2.57-2.55 (4H, m), 2.02-1.99 (4H, m) MS: m/z: 516 [M + H] |
| Example 40 | 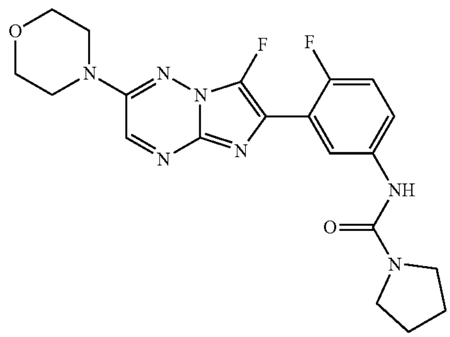 [SMILES: O=C(Nc1ccc(F)c(-c2nc3ncc(N4CCOCC4)nn3c2F)c1)N1CCCC1] | N-(4-fluoro-3-(7-fluoro-2-morpholinoimidazo[1,2-b][1,2,4]triazin-6-yl)phenyl)pyrrolidine-1-carboxamide | ¹H NMR (400 MHz, DMSO-d$_6$): δ 8.71 (1H, s), 8.32 (1H, s), 8.08 (1H, dd, J = 6.6, 2.8), 7.66-7.62 (1H, m), 7.19 (1H, dd, J = 10.1, 9.1), 3.78-3.75 (4H, m), 3.61-3.58 (4H, m), 3.39-3.36 (4H, m), 1.87-1.84 (4H, m) MS: m/z: 430 [M + H] |
| Example 41 | 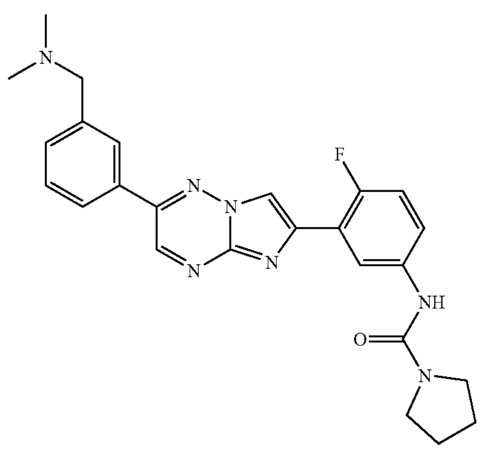 [SMILES: CN(C)Cc1cccc(-c2cnc3nc(-c4cc(NC(=O)N5CCCC5)ccc4F)cn3n2)c1] | N-(3-(2-(3-((dimethylamino)methyl)phenyl)imidazo[1,2-b][1,2,4]triazin-6-yl)-4-fluorophenyl)pyrrolidine-1-carboxamide | ¹H NMR (400 MHz, DMSO-d$_6$): δ 9.22 (1H, s), 8.61 (1H, d, J = 3.8), 8.45 (1H, dd, J = 6.8, 2.8), 8.37 (1H, m), 8.08 (1H, s), 8.05 (1H, d, J = 7.8), 7.71-7.67 (1H, m), 7.57 (1H, t, J = 7.6), 7.51 (1H, d, J = 7.6), 7.24 (1H, dd, J = 10.9, 9.1), 3.51 (2H, s), 3.42-3.39 (4H, m), 2.20 (6H, s), 1.89-1.86 (4H, m) MS: m/z: 460 [M + H] |
| Example 42 | 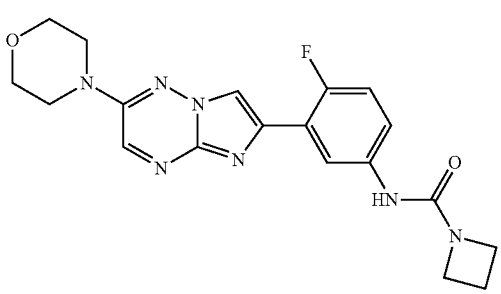 [SMILES: O=C(Nc1ccc(F)c(-c2cn3nc(N4CCOCC4)cnc3n2)c1)N1CCC1] | N-(4-fluoro-3-(2-morpholinoimidazo[1,2-b][1,2,4]triazin-6-yl)phenyl)azetidine-1-carboxamide | ¹H NMR (400 MHz, DMSO-d$_6$): δ 8.7 (1H, s), 8.55 (1H, s), 8.3 (1H, s), 8.15 (1H, s), 7.6 (1H, s), 7.25-7.1 (1H, m), 4.1-3.9 (4H, m), 3.8-3.7 (4H, br m), 3.65-3.45 (4H, br m), 2.25-2.1 (2H, m) MS: m/z: 398 [M + H] |

-continued

| Example | Structure | Chemical name | Physical data ($^1$H NMR, MS) |
|---|---|---|---|
| Example 43 | 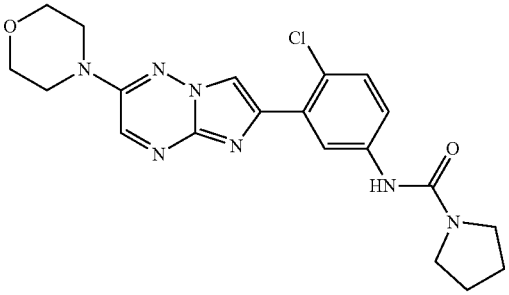 [SMILES: O=C(Nc1ccc(Cl)c(-c2cn3nc(N4CCOCC4)cnc3n2)c1)N1CCCC1] | N-(4-chloro-3-(2-morpholinoimidazo[1,2-b][1,2,4]triazin-6-yl)phenyl)pyrrolidine-1-carboxamide | $^1$H NMR (400 MHz, MeOD): δ 8.60 (1H, s), 8.33 (1H, s), 7.96 (1H, d, J = 2.6), 7.59 (1H, dd, J = 8.8, 2.7), 7.42 (1H, d, J = 8.7), 3.96-3.81 (4H, m), 3.72-3.57 (4H, m), 3.50 (4H, t, J = 6.7), 2.00 (4H, s) MS: m/z: 428 [M + H] |
| Example 44 | 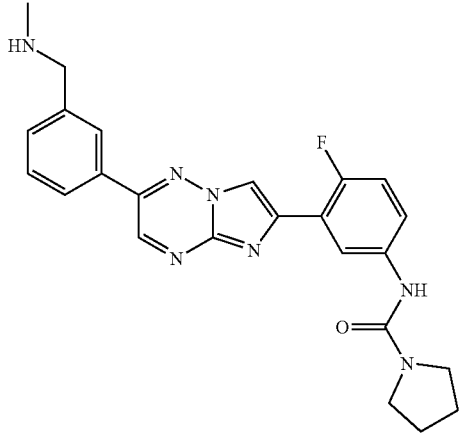 [SMILES: CNCc1cccc(-c2cnc3nc(-c4cc(NC(=O)N5CCCC5)ccc4F)cn3n2)c1] | N-(4-fluoro-3-(2-(3-((methylamino)methyl)phenyl)imidazo[1,2-b][1,2,4]triazin-6-yl)phenyl)pyrrolidine-1-carboxamide | $^1$H NMR (400 MHz, DMSO-d$_6$): δ 9.22 (1H, s), 8.58 (1H, d, J = 4.0), 8.45 (1H, dd, J = 6.8, 2.8), 8.37 (1H, s), 8.13 (1H, s), 8.05-8.02 (1H, m), 7.71-7.67 (1H, m), 7.59-7.55 (2H, m), 7.27-7.22 (1H, m), 3.81 (2H, s), 3.42-3.39 (5H, m), 2.34 (3H, s), 1.91-1.86 (4H, m) MS: m/z: 446 [M + H] |
| Example 45 | 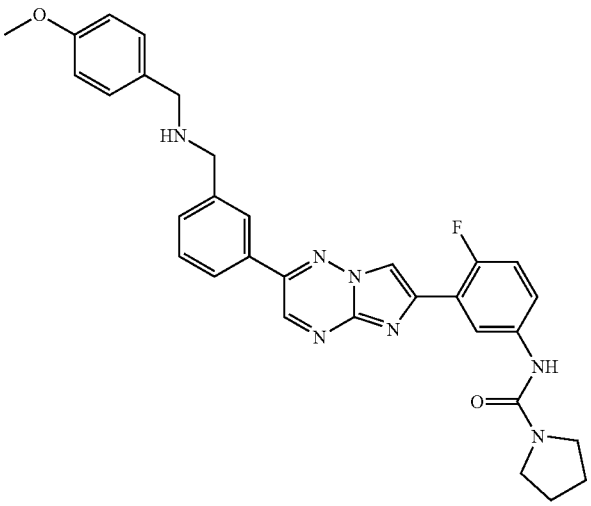 [SMILES: COc1ccc(CNCc2cccc(-c3cnc4nc(-c5cc(NC(=O)N6CCCC6)ccc5F)cn4n3)c2)cc1] | N-(4-fluoro-3-(2-(3-(((4-methoxybenzyl)amino)methyl)phenyl)imidazo[1,2-b][1,2,4]triazin-6-yl)phenyl)pyrrolidine-1-carboxamide | $^1$H NMR (400 MHz, DMSO-d$_6$): δ 9.22 (1H, s), 8.59 (1H, d, J = 3.8), 8.45 (1H, dd, J = 6.8, 2.8), 8.37 (1H, s), 8.12 (1H, s), 8.03-8.00 (1H, m), 7.71-7.67 (1H, m), 7.57-7.55 (2H, m), 7.29-7.22 (3H, m), 6.90-6.87 (2H, m), 3.79 (2H, s), 3.73 (3H, s), 3.66 (2H, s), 3.42-3.36 (5H, m), 1.89-1.85 (4H, m) MS: m/z: 552 [M + H] |
| Example 46 | 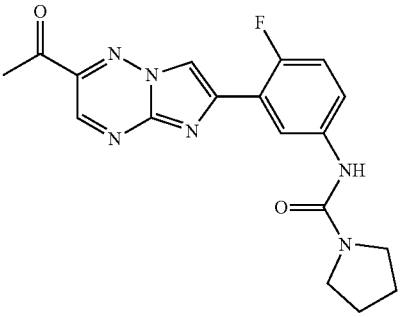 [SMILES: CC(=O)c1cnc2nc(-c3cc(NC(=O)N4CCCC4)ccc3F)cn2n1] | N-(3-(2-acetylimidazo[1,2-b][1,2,4]triazin-6-yl)-4-fluorophenyl)pyrrolidine-1-carboxamide | $^1$H NMR (400 MHz, DMSO-d$_6$): δ 9.00 (1H, s), 8.72 (1H, d, J = 3.8), 8.46 (1H, dd, J = 6.6, 2.8), 8.40 (1H, s), 7.75-7.71 (1H, m), 7.29-7.24 (1H, m), 3.41-3.38 (4H, m), 2.69 (3H, s), 1.88-1.85 (4H, m) MS: m/z: 369 [M + H] |

-continued

| Example | Structure | Chemical name | Physical data (¹H NMR, MS) |
|---|---|---|---|
| Example 47 | 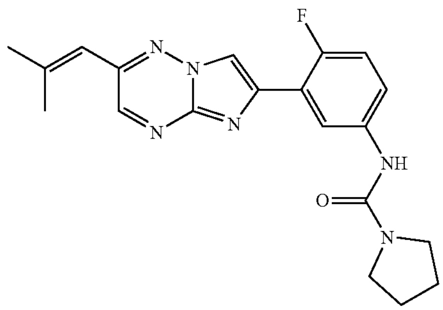 [SMILES: CC(C)=Cc1cnc2nc(-c3cc(NC(=O)N4CCCC4)ccc3F)cn2n1] | N-(4-fluoro-3-(2-(2-methylprop-1-en-1-yl) imidazo[1,2-b][1,2,4] triazin-6-yl)phenyl) pyrrolidine-1-carboxamide | ¹H NMR (400 MHz, DMSO-d$_6$): δ 8.54 (1H, s), 8.43-8.40 (2H, m), 8.35 (1H, s), 7.69-7.65 (1H, m), 7.22 (1H, dd, J = 10.9, 8.8), 6.42 (1H, s), 3.41-3.37 (4H, m), 2.17 (3H, s), 2.03 (3H, s), 1.88-1.85 (4H, m) MS: m/z: 381 [M + H] |
| Example 48 | 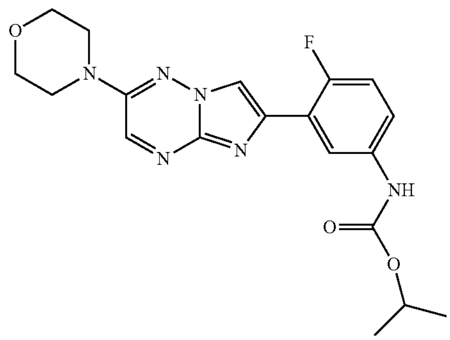 [SMILES: CC(C)OC(=O)Nc1ccc(F)c(-c2cn3nc(N4CCOCC4)cnc3n2)c1] | isopropyl (4-fluoro-3-(2-morpholinoimidazo[1,2-b][1,2,4]triazin-6-yl) phenyl)carbamate | ¹H NMR (400 MHz, DMSO-d$_6$): δ 9.69 (1H, s), 8.71 (1H, s), 8.35 (1H, dd, J = 6.6, 2.5), 8.12 (1H, d, J = 4.3), 7.45-7.41 (1H, m), 7.22 (1H, dd, J = 10.9, 9.1), 4.94-4.88 (1H, m), 3.77-3.75 (4H, m), 3.57-3.55 (4H, m), 1.26 (6H, d, J = 6.3) MS: m/z: 401 [M + H] |
| Example 49 | 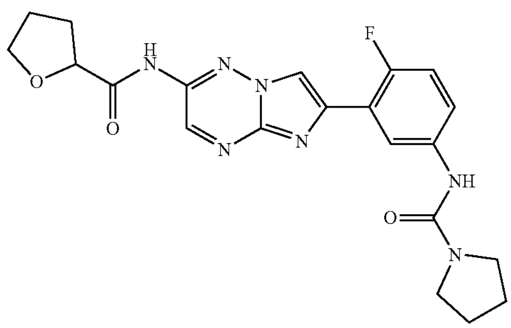 [SMILES: O=C(Nc1cnc2nc(-c3cc(NC(=O)N4CCCC4)ccc3F)cn2n1)C1CCCO1] | N-(4-fluoro-3-(2-(tetra-hydrofuran-2-carboxamido)imidazo [1,2-b][1,2,4]triazin-6-yl)phenyl)pyrrolidine-1-carboxamide | ¹H NMR (400 MHz, DMSO-d$_6$): δ 10.87 (1H, br s), 9.07 (1H, s), 8.40-8.36 (3H, m), 7.70-7.66 (1H, m), 7.22 (1H, dd, J = 10.9, 9.1), 4.57-4.53 (1H, m), 4.03-3.97 (1H, m), 3.88-3.83 (1H, m), 3.41-3.36 (4H, m), 2.27-2.20 (1H, m), 2.08-2.00 (1H, m), 1.96-1.85 (6H, m) MS: m/z: 440 [M + H] |
| Example 50 | 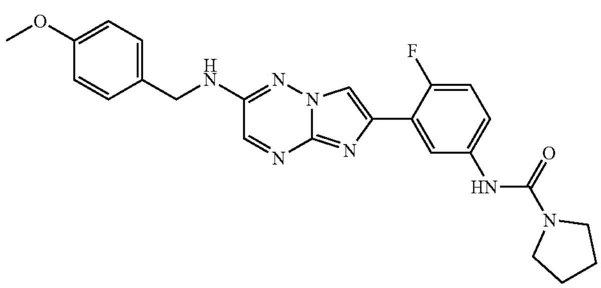 [SMILES: COc1ccc(CNc2cnc3nc(-c4cc(NC(=O)N5CCCC5)ccc4F)cn3n2)cc1] | N-(4-fluoro-3-(2-((4-methoxybenzyl)amino) imidazo[1,2-b][1,2,4] triazin-6-yl)phenyl) pyrrolidine-1-carboxamide | ¹H NMR (400 MHz, DMSO-d$_6$): δ 8.29-8.27 (2H, m), 8.18 (1H, s), 8.01-7.98 (2H, m), 7.61-7.57 (1H, m), 7.34 (2H, d, J = 8.6), 7.17-7.12 (1H, m), 6.92 (2H, d, J = 8.6), 4.37 (2H, d, J = 5.3), 3.74 (3H, s), 3.40-3.36 (4H, m), 1.87-1.84 (4H, m) MS: m/z: 462 [M + H] |
| Example 51 | 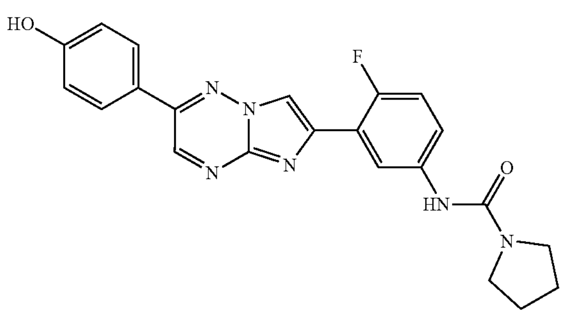 [SMILES: O=C(Nc1ccc(F)c(-c2cn3nc(-c4ccc(O)cc4)cnc3n2)c1)N1CCCC1] | N-(4-fluoro-3-(2-(4-hydroxyphenyl)imidazo [1,2-b][1,2,4]triazin-6-yl)phenyl)pyrrolidine-1-carboxamide | ¹H NMR (400 MHz, DMSO-d$_6$): δ 10.14 (1H, s), 9.16 (1H, s), 8.50 (1H, d, J = 3.8 Hz), 8.44 (1H, d, J = 6.7 Hz), 8.37 (1H, s), 8.02 (2H, d, J = 8.3 Hz), 7.69 (1H, t, J = 4.4 Hz), 7.24 (1H, t, J = 9.8 Hz), 6.98 (2H, d, J = 8.3 Hz), 3.42-3.35 (4H, m), 1.87 (4H, s) MS: m/z: 419 [M + H] |

-continued

| Example | Structure | Chemical name | Physical data (¹H NMR, MS) |
|---|---|---|---|
| Example 52 | 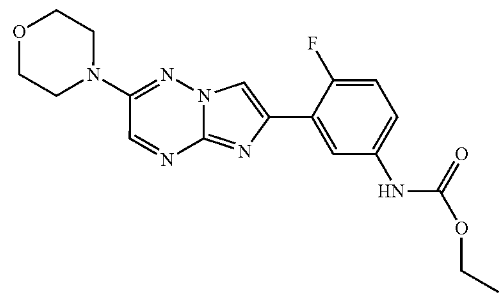 [SMILES: CCOC(=O)Nc1ccc(F)c(-c2cn3nc(N4CCOCC4)cnc3n2)c1] | ethyl (4-fluoro-3-(2-morpholinoimidazo[1,2-b][1,2,4]triazin-6-yl)phenyl)carbamate | ¹H NMR (400 MHz, DMSO-$d_6$): δ 9.74 (1H, bs), 8.72 (1H, s), 8.35, (1H, m), 8.13 (1H, d, J = 4.1 Hz), 7.46 (1H, m), 7.24 (1H, m), 4.16 (2H, q, J = 7.1 Hz), 3.77 (4H, m), 3.56 (4H, m), 1.27 (3H, t, J = 7.1 Hz) MS: m/z: 387 [M + H] |
| Example 53 | 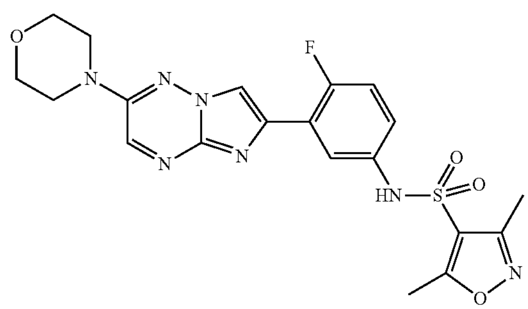 [SMILES: Cc1noc(C)c1S(=O)(=O)Nc1ccc(F)c(-c2cn3nc(N4CCOCC4)cnc3n2)c1] | N-(4-fluoro-3-(2-morpholinoimidazo[1,2-b][1,2,4]triazin-6-yl)phenyl)-3,5-dimethyl-isoxazole-4-sulfonamide | ¹H NMR (400 MHz, DMSO-$d_6$): δ 10.60 (1H, bs), 8.73 (1H, s), 8.15 (1H, d, J = 4.2 Hz), 7.99 (1H, dd, J = 6.6, 2.8 Hz), 7.30 (1H, dd, J = 10.8, 8.8 Hz), 7.10 (1H, m), 3.77 (4H, m), 3.57 (4H, m), 2.53 (3H, s), 2.27 (3H, s) MS: m/z: 474 [M + H] |
| Example 54 | 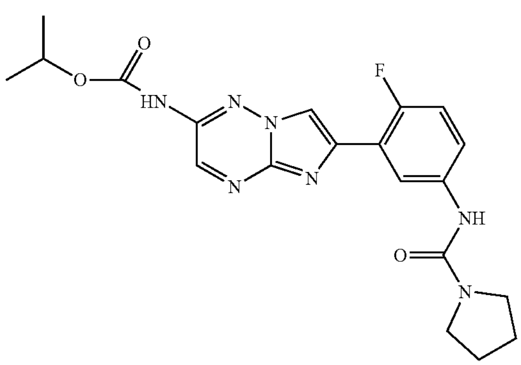 [SMILES: CC(C)OC(=O)Nc1cnc2nc(-c3cc(NC(=O)N4CCCC4)ccc3F)cn2n1] | isopropyl (6-(2-fluoro-5-(pyrrolidine-1-carboxamido)phenyl) imidazo[1,2-b][1,2,4]triazin-2-yl)carbamate | ¹H NMR (400 MHz, DMSO-$d_6$): δ 10.87 (1H, s), 8.94-8.95 (1H, m), 8.38-8.28 (3H, m), 7.70-7.64 (1H, m), 7.23-7.18 (1H, m), 5.01-4.92 (1H, m), 3.42-3.35 (4H, m), 1.90-1.79 (4H, m), 1.31-1.28 (6H, m) MS: m/z: 428 [M + H] |
| Example 55 | 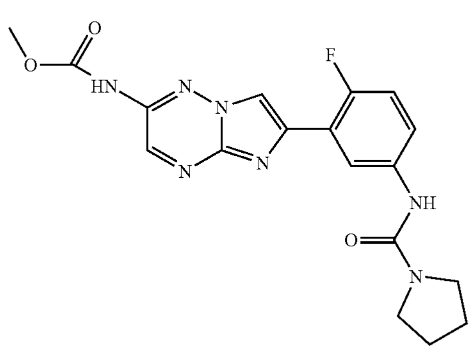 [SMILES: COC(=O)Nc1cnc2nc(-c3cc(NC(=O)N4CCCC4)ccc3F)cn2n1] | methyl (6-(2-fluoro-5-(pyrrolidine-1-carboxamido)phenyl) imidazo[1,2-b][1,2,4]triazin-2-yl)carbamate | ¹H NMR (400 MHz, DMSO-$d_6$): δ 11.01 (1H, s), 8.98 (1H, m), 8.38-8.30 (3H, m), 7.68-7.65 (1H, m), 7.23-7.18 (1H, m), 3.76 (3H, s), 3.44-3.35 (4H, m), 1.93-1.80 (4H, m), MS: m/z: 400 [M + H] |

-continued

| Example | Structure | Chemical name | Physical data (¹H NMR, MS) |
|---|---|---|---|
| Example 56 | 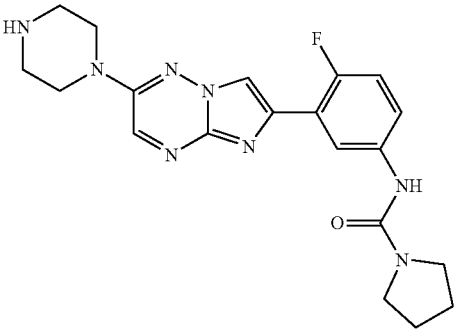 [SMILES: O=C(Nc1ccc(F)c(-c2cn3nc(N4CCNCC4)cnc3n2)c1)N1CCCC1] | N-(4-fluoro-3-(2-(piperazin-1-yl)imidazo[1,2-b][1,2,4]triazin-6-yl)phenyl)pyrrolidine-1-carboxamide | ¹H NMR (400 MHz, DMSO-$d_6$): δ 8.72 (1H, s), 8.35 (1H, dd, J = 6.8, 2.8), 8.31 (1H, s), 8.13 (1H, d, J = 4.0), 7.62-7.58 (1H, m), 7.18 (1H, dd, J = 10.9, 8.8) 3.76-3.73 (4H, m), 3.40-3.37 (5H, m), 3.22-3.19 (4H, m), 1.88-1.84 (4H, m) MS: m/z: 411 [M + H] |
| Example 57 | 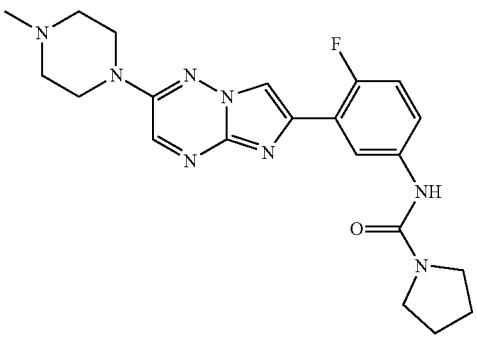 [SMILES: CN1CCN(c2cnc3nc(-c4cc(NC(=O)N5CCCC5)ccc4F)cn3n2)CC1] | N-(4-fluoro-3-(2-(4-methylpiperazin-1-yl)imidazo[1,2-b][1,2,4]triazin-6-yl)phenyl)pyrrolidine-1-carboxamide | ¹H NMR (400 MHz, DMSO-$d_6$): δ 8.70 (1H, s), 8.34-8.30 (2H, m), 8.09 (1H, d, J = 8.11), 7.63-7.59 (1H, m), 7.16 (1H, dd, J = 10.9, 9.1), 3.61-3.52 (4H, m), 3.43-3.22 (8H, m), 2.24 (3H, s), 1.87-1.84 (4H, m) MS: m/z: 425 [M + H] |
| Example 58 | 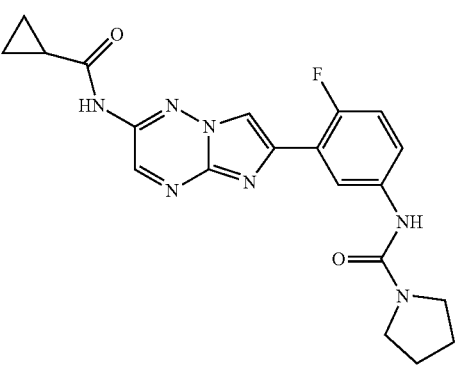 [SMILES: O=C(Nc1cnc2nc(-c3cc(NC(=O)N4CCCC4)ccc3F)cn2n1)C1CC1] | N-(3-(2-(cyclopropane-carboxamido)imidazo[1,2-b][1,2,4]triazin-6-yl)-4-fluorophenyl)pyrrolidine-1-carboxamide | ¹H NMR (400 MHz, DMSO-$d_6$) 11.50 (1H, s), 9.18 (1H, s), 8.39-8.34 (3H, m), 7.70-7.66 (1H, m), 7.24-7.19 (1H, m), 3.41-3.34 (4H, m), 2.05-1.99 (1H, m), 1.89-1.81 (4H, m), 0.94-0.89 (4H, m) MS: m/z: 410 [M + H] |
| Example 59 | 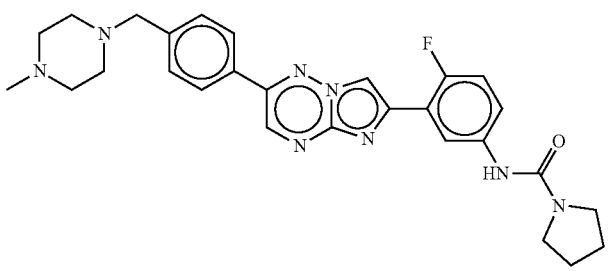 | N-(4-fluoro-3-(2-(4-((4-methylpiperazin-1-yl)methyl)phenyl)imidazo[1,2-b][1,2,4]triazin-6-yl)phenyl)pyrrolidine-1-carboxamide | ¹H NMR (400 MHz, DMSO-$d_6$) 9.22 (1H, s), 8.56 (1H, d, J = 3.5), 8.46-8.44 (1H, m), 8.37 (1H, s), 8.09 (2H, d, J = 8.1), 7.74-7.64 (1H, m), 7.52 (2H, d, J = 8.1), 7.27-7.22 (1H, m), 3.55 (2H, br s), 3.44-3.36 (4H, m), 2.46-2.26 (8H, m), 2.16 (3H, s), 1.93-1.80 (4H, m) MS: m/z: 515 [M + H] |

The following Examples can be made according to analogous procedures to those described above.

| Example | Structure | Chemical name |
|---------|-----------|---------------|
| Example 23 | 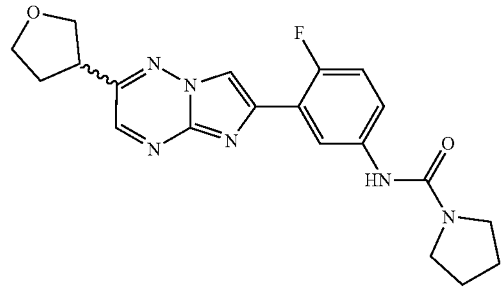 [SMILES: O=C(Nc1ccc(F)c(-c2cn3nc(C4CCOC4)cnc3n2)c1)N1CCCC1] | (+,−)-N-(4-fluoro-3-(2-(tetrahydrofuran-3-yl)imidazo[1,2-b][1,2,4]triazin-6-yl)phenyl)pyrrolidine-1-carboxamide |
| Example 31 | 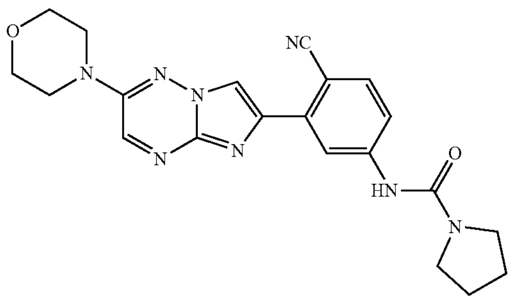 | N-(4-cyano-3-(2-morpholinoimidazo[1,2-b][1,2,4]triazin-6-yl)phenyl)pyrrrolidine-1-carboxamide |

Biological Activity

Assay 1. Intramacrophage *Leishmania donovani* Assay

The intramacrophage *Leishmania* assay was performed using a modified version of the method described in De Rycker et al. (Antimicrob Agents Chemother. 2013 July; 57(7):2913-22. Comparison of a high-throughput high-content intracellular *Leishmania donovani* assay with an axenic amastigote assay. De Rycker M, Hallyburton I, Thomas J, Campbell L, Wyllie S, Joshi D, Cameron S, Gilbert I H, Wyatt P G, Frearson J A, Fairlamb A H, Gray D W.). Procedure: 350 nl of compound was pre-dispensed into 384 well sterile intermediary plates. For single point screening, amphotericin B was added to all wells of column 24 as a positive control (final concentration 2 µM) and DMSO to column 23. For potency determinations, ten-point, one in three dilution curves were created with the highest concentration being 50 µM and on each plate a control curve of amphotericin B was included. Controls were as follows: columns 11 and 12: DMSO, columns 23 and 24: amphotericin B (final concentration 2 µM). To the intermediary plates, 35 µl of THP-1 media was added and plates were shaken for >5 min to ensure complete mixing. THP-1 cells (8,000 per well, 50 µl) were plated into black clear-bottom 384 well plates (Corning) in presence of 20 nM PMA. After 20 min at RT, the plates were incubated at 37° C. under 5% $CO_2$ in a humidified incubator for 75 h. The cells were then washed with 450 µl sterile phosphate buffered saline (PBS) supplemented with 1 mM $CaCl_2$, 0.5 mM $MgCl_2$, 0.1% (w/v) bovine serum albumin (PBS-A) and amastigotes were added to all wells at a multiplicity of infection of 5 (40,000 amastigotes per well). After 40 min at RT, plates were returned to the incubator. Amastigotes were incubated in the presence of THP-1 macrophages for 16 h. Any remaining extracellular amastigotes were subsequently removed with an overflow wash of 1 mL PBS-A per well (wash buffer is being aspirated from the top of the well as it is being dispensed) followed by addition of 25 µl of the compound pre-dilutions using a Fluidx Ipette-pro pipetting station. The final dilution of each compound was 200-fold. Plates were incubated for 96 h and then washed (250 µl PBS-A) and fixed (4% (v/v) formaldehyde-PBS, 30 min, RT). After fixation, the wells were washed with 250 µl PBS, stained (10 µg/mL DAPI, 0.4 µg mL-1 HCS Cellmask Deep Red in PBS+0.1% (v/v) Triton X-100, 30 min, RT) and washed with 250 µl PBS. Finally, PBS+0.05% (v/v) thimerosal was added to the wells, the plates were sealed and imaged on a high-content microscope (GE IN Cell 2000) using a 10× objective. Image analysis was carried out with GE IN Cell Analyzer 1000 Workstation using the "Multi Target Analysis" module. Settings for segmentation were as follows: nuclei: minimum area: 142.384 µm2, sensitivity: 81, method: top-hat; cells: characteristic area: 2500 µm2, sensitivity: 60, method: multiscale top-hat; organelles (amastigotes): granule size 1-3, 3 scales, sensitivity: 90, detection in entire cell. For each well, i) THP-1 cell count (cytotoxicity readout) and ii) average number of amastigotes per cell (potency readout) were calculated, both in terms of $pEC_{50}$ values.

Results of the Intramacrophage *Leishmania donovani* Assay (Assay 1)

All Examples (other than Examples 23 and 31) were tested in the Intramacrophage *Leishmania donovani* assay.

All Examples tested were found to have a $pEC_{50}$ value from 4.6 to 6.7 against *Leishmania donovani* except Examples 16, 32, 33, 34, 39, 52 and 53 which were found to have a $pEC_{50}$ value of less than 4.3 (the minimum threshold of the assay). Example 1 was found to have a $pEC_{50}$ value of 6.2 against *Leishmania donovani*.

All Examples tested were found to show cytotoxicity against THP-1 cells with a $pEC_{50}$ value of 4.4 or lower, except Examples 18, 19, 38, 45, 50, 51 and 59 which showed $pEC_{50}$ values from 5.4 to 4.8. Example 1 showed cytotoxicity against THP-1 cells with a $pEC_{50}$ value of less than 4.3 (the minimum threshold of the assay).

Assay 2. *Trypanosoma cruzi* Intracellular Assay

Compounds were dispensed into black 384-well assay plates (Corning) by acoustic dispensing (LabCyte ECHO). For potency determinations, ten-point one in three dilution curves were generated, with a top concentration of 50 μM. Vero cells were infected overnight with *T. cruzi* trypomastigotes in T225 tissue culture flasks at a multiplicity of infection of 5. Next, any remaining free trypomastigotes were washed away with serum free MEM media and the infected Vero cells were harvested by trypsinisation. The infected Vero cells were then plated into 384-well plates containing the compounds to be tested, at 4000 cells per well in MEM media with 1% FCS. After 72 h incubation at 37° C. in presence of 5% $CO_2$, the plates were fixed with 4% formaldehyde for 20 minutes at room temperature and stained with 5 μg/ml Hoechst 33342. The plates were imaged on a Perkin Elmer Operetta high-content imaging system using a 20× objective. Images were analysed using the Columbus system (Perkin Elmer). The image analysis algorithm first identified the Vero nuclei followed by demarcation of the cytoplasm and identification of intracellular amastigotes. This algorithm reported mean number of parasites per Vero cell and total number of Vero cells.

Results of the *Trypanosoma cruzi* Intracellular Assay (Assay2)

Examples 1-6, 8, 10 and 34 were tested in the *Trypanosoma cruzi* intracellular assay.

Examples 1-6, and 8 were found to have a $pEC_{50}$ value from 6.6 to 7.7; Example 10 was found to have a $pEC_{50}$ value of 4.7 and Example 34 was found to have a $pEC_{50}$ value of 4.6, against *Trypanosoma cruzi*. Example 1 was found to have a $pEC_{50}$ value of 7.0 against *Trypanosoma cruzi*. All Examples tested showed cytotoxicity against VERO cells with a $pEC_{50}$ of 4.5 or lower. Example 1 showed cytotoxicity against VERO cells with a $pEC_{50}$ of less than 4.3 (the minimum threshold of the assay).

Assay 3. *Trypanosoma brucei* Cell Growth Inhibition Assay

Measurement of the ability of the compounds to inhibit trypanosome (*T. b. brucei*, BSF427, VSG118) cell growth was performed using a modification of the cell viability assay previously described by Raz et al. (Raz B.; Iten M.; Grether-Buhler Y.; Kaminski R.; Brun R. The Alamar Blue assay to determine drug sensitivity of African trypanosomes (*T. b. rhodesiense* and *T. b. gambiense*) in vitro. Acta Trop. 1997, 68, 139-147). Compounds were dissolved in DMSO at a top concentration of 10 mM and serially diluted in half log steps to achieve a range of final assay concentrations of 50 μM to 0.5 nM. Compound at each concentration (200-fold final) was added to clear 96-well tissue culture plates in a volume of 1 μL. Then 2000 cells per well in relevant growth medium (HMI-9T for *T. brucei*, a modification of HMI-9 as described by Hurumi et al. (Hirumi H.; Hirumi K. Continuous cultivation of *Trypanosoma brucei* blood stream forms in a medium containing a low concentration of serum-protein without feeder cell-layers. J. Parasitol. 1989, 75, 985-989.) where 0.2 mM 2-mercaptoethanol was replaced with 0.056 mM thiolglycerol, and MEM with 10% FBS for MRC5) were then added to columns 1-11 of the plates in a volume of 199 μL. To column 12, 200 μL of medium was added to provide a no cells control. Plates were then incubated at 37° C. in an atmosphere of 5% $CO_2$ for 69 h, before the addition of 20 μL of 500 μM rezasurin solution, and a further incubation period of 4 h. Plates were then read on a BioTek flx800 fluorescent plate reader, and percentage inhibition was compared to the maximum and minimum assay controls. Concentration effect curves were fitted using nonlinear regression using XLFit 4.2 and $EC_{50}$ values determined.

Results of the *Trypanosoma brucei* Cell Growth Inhibition Assay (Assay 3)

Examples 1-4, 8-18, 20-22, 26-32, 39, 42, 48, 52 and 53 were tested in the *Trypanosoma brucei* cell growth inhibition assay.

All Examples tested were found to have a $pEC_{50}$ value of 6.2 or higher against *Trypanosoma brucei*, except Examples 10, 16, 32, 39, 53, which were found to have a $pEC_{50}$ value of 4.7 or lower. Example 1 was found to have a $pEC_{50}$ value of greater than 8.0 against *Trypanosoma brucei* (the maximum threshold of the assay).

Assay 4. Solubility Assay—ChemiLuminescent Nitrogen Detection (CLND)

I. Compounds

A 10 mM DMSO stock solution of the compound was prepared.

Solvents and Buffers

Organic solvents of HPLC grade were used. Ultra pure water (Milli-Q grade) was used. Buffers were prepared with ultra pure water and filtered using 0.45μ cameo filters.

Aqueous Buffer Solution: Phosphate Buffer Saline (PBS) @ pH 7.4 was prepared from Sigma dry powder packs, P-3813. Each one was diluted to 1 liter with deionised water. The pH was checked before the solution was used II. Procedures.

a) DMSO concentration was measured. DMSO blanks and ondansetron and caffeine standards were added to the plate (column 12, A, B, C, & D for the blanks and E, F, G, & H for the standards). Plates were covered with foil. When the UV and CLND detectors baselines appeared to be stable, the CLND was zeroed.

b) Once DMSO concentration measurements were complete, a filtration plate was prepared from each parent plate by diluting 5 μl of the 10 mM DMSO stock solution to 100 L with pH7.4 PBS.

c) After the plates were prepared, they were covered with a plate lid and left to incubate for 1 h at room temperature.

d) Sample was filtered using MILLIPORE MultiScreen Solubility (MSSLBPC10) Filtration Plates, to NUNC V well plates. The filter plate was removed and the NUNC plate was sealed with a power seal plate seal.

e) HPLC/CLND instruments were set up and left to equilibrate. Mobile phases (MeOH:$H_2O$ 1:1, flow rate: 0.2 ml/min, sensitivity z10, Gain High). The samples were run.

f) The assay curve fit was done by linear regression and solubility values were reported in μM.

Results of the Solubility Assay (CLND) (Assay 4)

Examples 1-6, 12-25, 27-30, 35-38, 40-49 and 54-58, were tested in the solubility assay (CLND).

Examples 1, 13, 15, 24, 25, 27, 28, 40-42, 44, 46, 56 and 57 were found to have an average solubility value from 416 μM to 100 μM in this assay. Examples 2-6, 12, 14, 20, 21, 29, 30, 35-38, 43, 45, 47-49, 54, 55 and 58 were found to have an average solubility value from 83 μM to 10 μM in this assay. Examples 16-19 and 22 were found to have an average solubility value from 6.0 μM to 1.0 μM in this assay. Example 1 was found to have an average solubility value of 100.8 μM in this assay.

Assay 5. *Leishmania donovani* Intracellular Assay

Compounds were dispensed into black 384-well assay plates (Greiner) by acoustic dispensing (LabCyte ECHO). For potency determinations, eleven-point, one in three dilution curves were generated, with a top concentration of 50 µM. THP-1 human monocytes cells were dispensed in T225 tissue culture flasks and differentiated using 30 nM of PMA, after 24 hours they were infected overnight using *Leishmania donovani* expressing Green Fluorescent Protein (eGFP) amastigotes in the same T225 tissue culture flasks at a multiplicity of infection of 10. Next, any remaining free amastigotes were washed away with PBS and the infected THP-1 cells were harvested by trypsinisation. The infected cells were then plated into 384-well plates containing the compounds to be tested, at 3000 cells per well in RPMI media with 2% FBS and 25 mM Sodium bicarbonate. After 96 h incubation at 37° C. in presence of 5% $CO_2$, the plates were fixed with 4% formaldehyde for 30 minutes, washed with PBS and stained with 0.1 mg/mL of DAPI for 30 minutes and washed again with PBS. The plates were imaged on a Perkin Elmer Opera high-content imaging system using a 20× air objective with two expositions, one for DAPI stain and other for eGFP. Images were analysed using the Acapella building blocks system (Perkin Elmer). The image analysis algorithm first identified the THP-1 nuclei followed by demarcation of the cytoplasm and identification of intracellular amastigotes. This algorithm reported mean number of parasites per THP-1 cell, the percentage of infected THP-1 cells and the total number of THP-1 cells.

Results of the *Leishmania donovani* Intracellular Assay (Assay 5)

Examples 1-6, 12-25, 27-30, 35-49 and 58 were tested in the Intramacrophage *Leishmania donovani* assay.

All Examples tested were found to have a $pEC_{50}$ value from 5.8 to 7.2 against *Leishmania donovani*. Example 1 was found to have a $pEC_{50}$ value of 6.8 against *Leishmania donovani*.

All Examples tested were found to show cytotoxicity against THP-1 cells with a $pEC_{50}$ value of 4.7 or lower, except Examples 37, 38, 41, 44, 45 and 48, which showed $pEC_{50}$ values of between 5.6 and 5.0. Example 1 showed cytotoxicity against THP-1 cells with a $pEC_{50}$ value of less than 4.3 (the minimum threshold of the assay).

Assay 6. *Trypanosoma cruzi* Intracellular Assay

Compounds were dispensed into black 384-well assay plates (Greiner) by acoustic dispensing (LabCyte ECHO). For potency determinations, eleven-point, one in three dilution curves were generated, with a top concentration of 50 µM. H9C2 rat cardiomyocytes cells were dispensed in T225 tissue culture flasks and after 4 hours they were infected during 18 hours with *T. cruzi* trypomastigotes in the same T225 tissue culture flasks at a multiplicity of infection of 1. Next, any remaining free trypomastigotes were washed away with PBS and the infected H9C2 cells were harvested by trypsinisation. The infected H9C2 cells were then plated into 384-well plates containing the compounds to be tested, at 2500 cells per well in DMEM media with 2% FBS, 1% Penicillin/Streptomocin, 2 mM L-Glutamine, 1 mM Na Pyruvate and 25 mM HEPES. After 72 h incubation at 37° C. in presence of 5% $CO_2$, the plates were fixed and stained with 4% formaldehyde and 2 µM Draq5 for 3 hours at room temperature. The plates were imaged on a Perkin Elmer Opera high-content imaging system using a 20× air objective. Images were analysed using the Acapella building blocks system (Perkin Elmer). The image analysis algorithm first identified the H9C2 nuclei followed by demarcation of the cytoplasm and identification of intracellular amastigotes. This algorithm reported mean number of parasites per H9C2 cell, the percentage of infected H9C2 cells and the total number of H9C2 cells.

Results of the *Trypanosoma cruzi* Intracellular Assay (Assay 6)

Examples 1-6, 10-25 and 27-58 were tested in the *Trypanosoma cruzi* intracellular assay.

Examples 1-6, 11-25, 27-30, 35-52 and 54-58 were found to have a $pEC_{50}$ value from 6.2 to 8.3 against *Trypanosoma cruzi*. Examples 10, 32-34 and 53 were found to have a $pEC_{50}$ value from 4.4 to 5.0 against *Trypanosoma cruzi*. Example 1 was found to have a $pEC_{50}$ value of 7.4 against *Trypanosoma cruzi*.

All Examples tested showed cytotoxicity against H9c2 cells with a $pEC_{50}$ of 4.9 or lower, except Examples 33, 38 and 45 which showed cytotoxicity against H9c2 cells with a $pEC_{50}$ from 6.1 to 5.5. Example 1 showed cytotoxicity against H9c2 cells with a $pEC_{50}$ of less than 4.3 (the minimum threshold of the assay).

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. A compound of Formula (I), or a salt thereof,

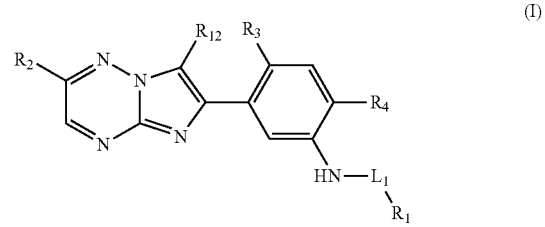

Wherein $R_1$ is selected from $C_1$-$C_6$alkyl, $C_3$-$C_7$cycloalkyl, $C_4$-$C_7$heterocycloalkyl, phenyl, $C_5$-$C_6$heteroaryl, $C_1$-$C_6$alkoxy, —$OC_3$-$C_7$cycloalkyl and $NR_{10a}R_{10b}$, wherein $C_3$-$C_7$cycloalkyl, $C_4$-$C_7$heterocycloalkyl, phenyl, $C_5$-$C_6$heteroaryl and —$OC_3$-$C_7$cycloalkyl are optionally substituted with one to three groups independently selected from hydroxy, methoxy, $C_1$-$C_3$alkyl and halo;

$L_1$ is a linker group selected from —C(O)— and —S(O)$_n$—, wherein n represents 1 to 2;

$R_3$ is selected from hydrogen, halo, methyl, methoxy and cyano;

$R_4$ is selected from hydrogen, halo, methyl, methoxy and cyano;

$R_{12}$ is selected from hydrogen, halo and methyl;

$R_2$ is selected from hydrogen, halo, Ar, Cy, X, $NR_{5a}R_{5b}$ and —C(O)—$R_{15}$;

Ar is selected from phenyl and $C_5$-$C_6$heteroaryl, each of which is optionally substituted with one to three groups independently selected from halo and -$L_2$-$R_7$;

$L_2$ is a linker group selected from a bond, —$(CH_2)_m$—, —$O(CH_2)_m$—, —$C_2$-$C_4$alkenyl- —$OC_2$-$C_4$alkenyl-, —$(CH_2)_p$—NH—$(CH_2)_q$—, and —$(CH_2)_p$C(O)—

(CH$_2$)$_q$—; wherein m represents 1 to 4 and p and q independently represent 0 to 4;

R$_7$ is selected from hydrogen; hydroxy; NR$_{8a}$R$_{8b}$; C$_4$-C$_7$heterocycloalkyl optionally substituted with one or two C$_1$-C$_3$alkyl groups; C$_3$-C$_7$cycloalkyl; C$_1$-C$_6$alkoxy optionally substituted with one NR$_{14a}$R$_{14b}$ group; phenyl optionally substituted with one to three groups independently selected from halo, methoxy and methyl;

Cy is selected from C$_3$-C$_7$cycloalkyl, C$_4$-C$_7$heterocycloalkyl, C$_5$-C$_7$cycloalkenyl and C$_5$-C$_7$heterocycloalkenyl, each of which is optionally substituted with one to three groups independently selected from C$_1$-C$_3$alkyl, C$_4$-C$_7$heterocycloalkyl and NR$_{11a}$R$_{11b}$;

X is selected from C$_1$-C$_6$alkyl, C$_2$-C$_6$alkenyl, C$_1$-C$_6$alkoxy, each of which is optionally substituted with one to three groups independently selected from hydroxy, methoxy, halo, NR$_{13a}$R$_{13b}$ and C$_4$-C$_7$heterocycloalkyl, wherein C$_4$-C$_7$heterocycloalkyl is optionally substituted with one to three C$_1$-C$_3$alkyl groups;

R$_{5a}$ is selected from hydrogen; C$_1$-C$_6$alkyl optionally substituted with one group selected from Ar and Cy; —C(O)—R$_9$; —C(O)—OR$_9$ and —SO$_2$—R$_9$;

R$_{5b}$ is selected from hydrogen and C$_1$-C$_3$alkyl;

R$_{8a}$ and R$_{8b}$ are independently selected from hydrogen and C$_1$-C$_3$alkyl;

R$_9$ is selected from C$_1$-C$_6$alkyl, C$_3$-C$_7$cycloalkyl, C$_4$-C$_7$heterocycloalkyl, phenyl and C$_5$-C$_6$heteroaryl;

R$_{10a}$ and R$_{10b}$ are independently selected from hydrogen and C$_1$-C$_3$alkyl;

R$_{11a}$ and R$_{11b}$ are independently selected from hydrogen and C$_1$-C$_3$alkyl;

R$_{13a}$ and R$_{13b}$ are independently selected from hydrogen and C$_1$-C$_3$alkyl;

R$_{14a}$ and R$_{14b}$ are independently selected from hydrogen and C$_1$-C$_3$alkyl; and R$_{15}$ is selected from C$_1$-C$_6$alkyl, Ar and Cy.

2. A compound of Formula (I) according to claim 1, or a pharmaceutically acceptable salt thereof.

3. A compound according to claim 1, wherein R$_1$ is selected from C$_4$-C$_6$heterocycloalkyl, C$_5$-C$_6$heteroaryl, and C$_1$-C$_6$alkoxy, wherein C$_4$-C$_6$heterocycloalkyl and C$_5$-C$_6$heteroaryl are optionally substituted with one to three groups independently selected from hydroxy, methoxy, C$_1$-C$_3$alkyl and halo.

4. A compound according to claim 1, wherein L$_1$ is selected from —C(O)— and —S(O)$_n$—, wherein n represents 2.

5. A compound according to claim 1, wherein R$_3$ is hydrogen, halo or cyano.

6. A compound according to claim 1, wherein R$_4$ is hydrogen.

7. A compound according to claim 1, wherein R$_{12}$ is selected from hydrogen, fluoro and methyl.

8. A compound according to claim 1, wherein R$_2$ is selected from hydrogen, Ar, Cy, X, NR$_{5a}$R$_{5b}$ and —C(O)—R$_{15}$.

9. A pharmaceutical composition comprising (a) a compound according to claim 1, or a pharmaceutically acceptable salt thereof, and (b) a pharmaceutically acceptable excipient.

10. A combination comprising (a) a compound of Formula (I) according to claim 1, or a pharmaceutically acceptable salt thereof, and (b) at least one additional therapeutic agent.

11. A method of treatment or prevention of a parasitic disease selected from Chagas disease, Human African Trypanosomiasis and leishmaniasis, which method comprises administering to a mammal in need thereof, a therapeutically effective amount of a compound according to claim 1, or a pharmaceutically acceptable salt thereof.

12. A method of treatment or prevention according to claim 11, wherein the mammal is a human.

13. A method of treatment or prevention according to claim 11, wherein the leishmaniasis is visceral leishmaniasis.

14. A method of treatment or prevention according to claim 11, wherein the parasitic disease is Chagas disease.

* * * * *